(12) United States Patent
Chung et al.

(10) Patent No.: US 8,071,544 B2
(45) Date of Patent: Dec. 6, 2011

(54) CRYSTALLIZED RECOMBINANT HUMAN GROWTH FACTOR FORMULATIONS

(75) Inventors: Wen-Li Chung, San Mateo, CA (US);
Lawrence Bush, Seattle, WA (US);
Sergey Pechenov, Lansdale, PA (US);
Sujit K. Basu, Newton, MA (US)

(73) Assignee: Althea Technologies, Inc., San Diego, CA (US)

( * ) Notice: Subject to any disclaimer, the term of this patent is extended or adjusted under 35 U.S.C. 154(b) by 0 days.

(21) Appl. No.: 12/519,720

(22) PCT Filed: Dec. 13, 2007

(86) PCT No.: PCT/US2007/087417
§ 371 (c)(1),
(2), (4) Date: May 4, 2010

(87) PCT Pub. No.: WO2008/076819
PCT Pub. Date: Jun. 26, 2008

(65) Prior Publication Data
US 2010/0216705 A1 Aug. 26, 2010

Related U.S. Application Data

(60) Provisional application No. 60/870,605, filed on Dec. 18, 2006.

(51) Int. Cl.
*A61K 38/27* (2006.01)
*C07K 14/61* (2006.01)
(52) U.S. Cl. ......... 514/11.4; 514/5.1; 530/397; 530/399
(58) Field of Classification Search .................. None
See application file for complete search history.

(56) References Cited

U.S. PATENT DOCUMENTS

| | | | | |
|---|---|---|---|---|
| 5,346,903 A | * | 9/1994 | Ackerman et al. | 514/282 |
| 5,439,643 A | * | 8/1995 | Liebert | 422/25 |
| 5,589,167 A | * | 12/1996 | Cleland et al. | 424/85.7 |
| 7,351,798 B2 | * | 4/2008 | Margolin et al. | 530/350 |

FOREIGN PATENT DOCUMENTS

| | | | |
|---|---|---|---|
| WO | 9200998 A | | 1/1992 |
| WO | 9312812 A | | 7/1993 |
| WO | 2004060310 A | | 7/2004 |
| WO | WO/2004/060310 | * | 7/2004 |

OTHER PUBLICATIONS

Govardhan et al., Novel Long-Acting Crystal Formulation of Human Growth Hormone, Pharm. Res. 22, 1461-1470, 2005.*
Branden et al. Introduction to Protein Structure, Second Edition, Garland Publishing Inc.,pp. 1, 374, 375, 382, New York, 1999.*
Drenth et al., Principles of X-ray Crystallography, Springer, New York, pp. i, ii, iii, 1-21, 1999.*
Kierzek et al., Models of protein crystal growth, Biophys Chem 91:1-20, 2001.*
Buts et al., Impact of natural variation in bacterial F17G adhesin on crystallization behaviour, Acta Cryst D61:1149-1159, 2005.*
Kundrot, Which strategy for a protein crystallization project?, Cell. Mol. Life Sci. 61: 525-536, 2004.*
Weber, Overview of Protein crystallization methods, Methods in Enzymology, vol. 276, pp. 13-22, 1997.*
Cudney, Protein crystallization and dumb luck, Rigaku Journal, vol. 16, No. 1, pp. 1-7, 1999.*
McPherson A., Current approaches to macromolecular crystallization, Eur. J. Biochem. 189:1-23, 1990.*
International Search Report from corresponding International Application Serial No. PCT/2007/087417 dated Feb. 5, 2009.
International Preliminary Report on Patentability including Written Opinion from corresponding International Application Serial No. PCT/2007/087417 issued Jun. 23, 2009.
European Application EP07869230 Office Action Dec. 11, 2009.

* cited by examiner

*Primary Examiner* — Elly-Gerald Stoica
(74) *Attorney, Agent, or Firm* — Wilson, Sonsini, Goodrich & Rosati

(57) ABSTRACT

Formulations containing complexed human growth hormone crystals are described. Also described are needleless injection systems for crystalline proteins.

6 Claims, 19 Drawing Sheets

CRYSTALLIZED RECOMBINANT HUMAN GROWTH FACTOR FORMULATIONS

CROSS-REFERENCE TO RELATED APPLICATIONS

This application is the National Stage application under 35 U.S.C. §371 of International Application No. PCT/US2007/087417, filed Dec. 13, 2007, which claims priority to U.S. Application Ser. No. 60/870,605, filed on Dec. 18, 2006. The contents of both applications are hereby incorporated by reference in their entireties.

TECHNICAL FIELD

This disclosure relates to formulations of protein therapeutics, and more particularly to formulations of human Growth Hormone.

BACKGROUND

Somatotropin or growth hormone ("GH") is a mammalian protein comprising a class of tropic hormones synthesized and secreted in the brain by the major gland of the endocrine system, the adenohypophysis. The secretion of GH and other tropic hormones by the adenohypophysis regulates the activity of cells in other endocrine glands and tissues throughout the body. Specifically, GH is secreted by somatotrophs of the anterior pituitary gland and functions to stimulate the liver and other tissues to synthesize and secrete IGF-1, a protein that controls cell division, regulates metabolic processes and exists in a free state or binds to one of six other proteins designated as IGFBP-1 through 6. The secretion process itself is modulated by opposing actions of somatoliberin (promoting GH release) and somatostatin (inhibiting GH release).

Human growth hormone ("hGH") serves as a critical hormone in the regulation of cell and organ growth and in physiological function upon various stages of aging. For example, overproduction of hGH results in gigantism in children and acromegaly in adults, whereas under-production leads to dwarfism in children [Mauras et al., J. Clin. Endocrinology and Metabolism, 85(10), 3653-3660 (2000); Frindik et al., Hormone Research, 51(1), 15-19 (1999); Leger et al., J. Clin. Endocrinology and Metabolism, 83(10), 3512-3516 (1998)], Turner's Syndrome (females only) [Bramswig, Endocrine, 15(1), 5-13 (2001); Pasquino et al., Hormone Research, 46(6), 269-272 (1996)] and chronic renal insufficiency [Carroll et al., Trends in Endocrinology and Metabolism, 11(6), 231-238 (2000); Ueland et al., J. Clin. Endocrinology and Metabolism, 87(6), 2760-2763 (2002); Simpson et al., Growth Hormone & IGF Research, 12, 1-33 (2002)]. In adults, hGH deficiency can affect metabolic processing of proteins, carbohydrates, lipids, minerals and connective tissue and can result in muscle, bone or skin atrophy [Mehls and Haas, Growth Hormone & IGF Research, Supplement B, S31-S37 (2000); Fine et al., J. Pediatrics, 136(3), 376-382 (2000); Motoyama et al., Clin. Exp. Nephrology, 2(2), 162-165 (1998)]. Other hGH deficiency disorders characterized by growth failure include AIDS wasting syndrome [Hirschfeld, Hormone Research, 46, 215-221 (1996); Tritos et al., Am. J. Medicine, 105(1), 44-57 (1998); Mulligan et al., J. Parenteral and Enteral Nutrition, 23(6), S202-S209 (1999); Torres and Cadman, BioDrugs, 14(2), 83-91 (2000)] and Prader-Willi syndrome [Ritzen, Hormone Research, 56(5-6), 208 (2002); Eiholzer et al., Eur. J. Pediatrics, 157(5), 368-377 (1998)].

To date, treatment regimens for hGH deficiency in humans focus primarily on subcutaneous injection of purified hGH made by recombinant DNA technology. The therapeutic is packaged as either a solution in a cartridge or a lyophilized powder requiring reconstitution at the time of use. The frequency of injection varies depending on the disease being treated and the commercially available product being used.

The use of subcutaneous administration as a rapid delivery route for hGH is necessitated by the inherent instability of the protein in solution. That instability results from cleavage of critical intramolecular crosslinks at specific positions within the amino acid sequence of the protein, which in turn disrupts the essential three-dimensional structure recognized by and associated with cellular surfaces in the patient. The mechanism for hGH cleavage or degradation is orchestrated primarily by oxidation of methionine residues or deamidation of aspartic acid residues upon dissolution, thereby rendering the protein inactive.

SUMMARY

The present disclosure provides formulations of crystalline hGH with improved stability. It further provides methods of preparing and methods of treatment utilizing such formulations.

The disclosure also describes crystalline protein formulations that can be administered to subjects with a needleless (jet) injection system, and methods of using such formulations.

In some aspects, the disclosure provides an hGH preparation including one or more, and preferably all, of: polyelectrolyte (preferably, poly-arginine); complexed recombinant human growth hormone or human growth hormone derivative (hGH) crystals; a buffer (e.g., salt buffer); a sodium salt having a sodium ion concentration range of 60 to 200 mM; and a suspending agent.

In some embodiments, the suspending agent is polyethylene glycol (e.g., PEG 3350, 6000, or 8000).

In some embodiments, the suspending agent is polyethylene glycol from about 2.5 to about 20% w/v.

In some embodiments, the hGH or hGH derivative is stable for a predetermined length of time and/or at a predetermined condition. In some embodiments, the length of time is at least 6, 9, 10, 12, 14, 16, 17, 18, 20, 22, or 24 months.

In some embodiments, the length of time is at least about 12, about 18, about 24, about 30 or about 36 months.

In some embodiments, the pH of the preparation is pH 6 to 7.

In some embodiments, preparation includes a phosphate buffer and the pH of the preparation has a pH of 6 to 7.

In some embodiments, the concentration of the poly-arginine complexed hGH crystal is from about 5 mg/mL to about 50 mg/mL. In some preferred embodiments, the concentration is between about 20 and about 30 mg/ml.

In some embodiments, the poly-arginine complexed hGH crystals have a particle size distribution of about 2 to about 100 µm (e.g., about 5 to about 20 µm, e.g., about 3 to about 15 µm).

In some embodiments, the ratio of hGH to polyarginine is from about 3 to about 15, e.g., from about 5 to about 8.

In some embodiments, the hGH preparation is disposed in a container with no head space or head space of up to 10 mm in a cylinder type siliconized container.

In some embodiments, the hGH preparation is disposed in a container containing multiple doses.

In some embodiments, the hGH preparation is disposed in a container containing a single dose.

In some embodiments, the container comprises a closure of either Teflon coated stoppers or rubber formulation 4432.

In some embodiments, the hGH preparation is disposed in a container with a fill volume of 0.2 mL to 1.0 mL.

In some embodiments, the preparation is disposed in a delivery device, e.g., a syringe suitable for subcutaneous injection, e.g., a pre-filled syringe.

In some embodiments, the preparation is disposed in a syringe having a needle of 29 gauge or finer.

In some embodiments, the preparation is disposed in a needle-free injector.

In some embodiments, the hGH is present at about 5 to about 100 mg/ml, about 10 to about 50 mg/l, or about 20 to about 30 mg/ml.

In some embodiments, the preparation also contains an antimicrobial agent, e.g., phenol or m-cresol.

In some embodiments, the preparation also contains hyaluronic acid.

In some embodiments, the preparation is free of polymers other than a suspension agent.

In some embodiments, the preparation is free of histidine buffer.

In some embodiments, the preparation also contains a preservative. In preferred embodiments, wherein the preservative is phenol or m-cresol. In more preferred embodiments, the preservative is phenol.

In some aspects, the disclosure features an hGH preparation that contains: poly-arginine complexed recombinant human growth hormone or human growth hormone derivative (hGH) crystals at 5-50 mg/ml; phosphate buffer at pH of 6.1-6.8; sodium chloride or sodium acetate at 60-200 mM; 2.5-20% polyethylene glycol, e.g., 6000 or 8000; that is disposed in a siliconized prefiled syringe with no more than 10 mm head space; and a volume of 0.2-1.0 ml.

In some embodiments, the syringe has a needle of 29 gauge or finer.

In some embodiments, the preparation is disposed in a needle-free injector.

In some aspects, the disclosure features an hGH preparation that contains: an hGH preparation containing one or more of, and preferably all, of: a suspension of hGH crystals coated with polyelectrolyte, e.g., polyaginine, wherein the crystalline hGH concentration is at 5-100 mg/mL, 10-50 mg/mL, or 20 to 30 mg/mL; a biologically compatible buffer maintaining crystallinity of the complex, preferably with pH range 5.0 to 8.0; a crystallinity promoting agent which maintains or increases crystallinity of said complex; and a tonicity modifier allowing for total osmolality of said compositions in the range of 250-450 mOsm/kg, 270-350 mOsm/kg, or 280-330 mOsm/kg.

In some embodiments, the hGH preparation includes a preservative, e.g., phenol. In some embodiments, the phenol is at a concentration of about 0.25% or about 0.2 to about 0.3%. w/v.

In some embodiments, the hGH preparation includes a chemical stabilizer, e.g., methionine or EDTA.

In some embodiments, the biologically compatible buffer has a buffer salt concentration in the range of about 1 to about 150 mM, about 2 to about 50 mM, or about 10 mM.

In some embodiments, the buffer salt is selected from the group that includes (consists of) acetate, triethanolamine, imidazole, phosphate, citrate, and Tris-HCl. In other embodiments, the buffer salt is selected from the group that includes phosphate, glycine, histidine, citrate, acetate, and Tris.

In some embodiments, the biologically compatible buffer is sodium phosphate, e.g., in the pH range of 5.8 to 7.0 or 6.0 to 6.5.

In some embodiments, the biologically compatible buffer comprises sodium phosphate and sodium citrate buffers, e.g., 2 mM Na citrate 8 mM Na phosphate. In some embodiments, the crystallinity promoting agent which maintains or increases crystallinity of said complex contains Na acetate, or polyethylene glycol e.g., PEG 3350-PEG 8000.

In some embodiments, the crystallinity promoting agent which maintains or increases crystallinity of said complex comprises PEG at about 1 to about 25 w/v %, e.g., about 2 to about 10 w/v %; or about 4 to about 6 w/v %.

In some embodiments, the crystallinity promoting agent which maintains or increases crystallinity of said complex contains phenol, e.g., at a concentration of about 0.1 to about 0.5% w/v.

In some embodiments, the tonicity modifier is selected from the group consisting of a neutral salt(s), sodium chloride, sodium acetate, Tris-HCl, a buffer salt outside of its working buffering pH range, a salt(s) of an amino acid(s) in the pH range outside its buffering pH range, glycine sodium salt, a polyol (such as mannitol or sorbitol), and a polyethylene glycol.

In some embodiments, the hGH preparation is disposed in a container containing multiple doses.

In some embodiments, the hGH preparation is disposed in a container containing a single dose.

In some embodiments, the container comprises a closure of either Teflon coated stoppers or rubber formulation 4432.

In some embodiments, the hGH preparation is disposed in a container with a fill volume of 0.2 mL to 1.0 mL.

In some embodiments, the hGH preparation is disposed in a delivery device, e.g., a syringe, suitable for subcutaneous injection, e.g., a pre-filled syringe.

In some embodiments, the hGH preparation is disposed in a needle-free injector.

In some embodiments, the hGH preparation contains hyaluronic acid.

In some aspects, the disclosure features a method of making an hGH preparation comprising combining the components of a preparation described herein. For example, combining an hGH preparation including one or more, and preferably all, of: polyelectrolyte (preferably, poly-arginine); complexed recombinant human growth hormone or human growth hormone derivative (hGH) crystals; a buffer (e.g., salt buffer); a sodium salt having a sodium ion concentration range of 60 to 200 mM; and a suspending agent. As another example, combining poly-arginine complexed recombinant human growth hormone or human growth hormone derivative (hGH) crystals at 5-50 mg/ml; phosphate buffer at pH of 6.1-6.8; sodium chloride or sodium acetate at 60-200 mM; 2.5-20% polyethylene glycol, e.g., 6000 or 8000.

In some aspects, the disclosure features a method of packaging a hGH preparation including disposing the components of a preparation described herein in a container to a fill volume of 0.2-1.0 ml wherein said container is a syringe, e.g., with no more than 10 mm head space and is preferably suitable for subcutaneous injection, to the patient.

In some aspects, the disclosure features a method of packaging a hGH preparation including disposing the components of the preparation in a container to a fill volume which includes multiple dosages of 0.2-1.0 ml.

In some aspects, the disclosure features a method of delivering a hGH preparation to a patient. The method includes
providing a hGH preparation described herein and
administering, e.g., by injection, no more than once every 2, 3, 4, 5, 6, 7, 8, 9, or 10 days.

In some aspects, the disclosure features a method of providing a hGH preparation, or information about a hGH preparation, to a party, e.g., a distributor, physician, pharmacy, hospital, HMO, wholesaler, retailer, government, patient or health care provider. The method includes comprising:

instructing the party that a hGH preparation containing the components of a preparation described herein is stable for a predetermined length of time and/or at a predetermined condition.

In some embodiments, the length of time is at least 6, 9, 10, 12, 14, 16, 17, 18, 20, 22, or 24 months.

In some embodiments, the length of time is at least 12, 18, 24, 30 or 36 months.

In some embodiments, the condition is temperature, e.g., 2-8° C. In some embodiments, the condition is room temperature, e.g., about 25° C.

In some aspects, the disclosure features a method of satisfying a standard, e.g., a standard imposed by a government agency, e.g., the FDA, e.g., a release specification or a label specification, or pharmaceutical compendium. The method includes:

providing evidence that, or asserting that, a hGH preparation, e.g., an hGH preparation described herein, is stable for a predetermined length of time and/or at a predetermined condition.

In some embodiments, the length of time is at least 6, 9, 10, 12, 14, 16, 17, 18, 20, 22, or 24 months.

In some embodiments, the length of time is at least 12, 18, 24, 30 or 36 months.

In some embodiments, the condition is temperature, e.g., 2-8° C.

In some embodiments, the condition is room temperature, e.g., about 25° C.

In some aspects, the disclosure features a needle-free injector having disposed therein a preparation of crystallized protein.

In some embodiments, the preparation is a solution of crystals.

In some embodiments, the crystals are cross-linked.

In some embodiments, the crystals are complexed with a polyelectrolyte, e.g., polyarginine.

In some embodiments, the preparation is of hGH or an hGH derivative.

In some embodiments, the preparation is an hGH or an hGH derivative preparation described herein.

In some embodiments, the preparation is not a vaccine.

In some embodiments, the crystals in the preparation have an average largest dimension of 0.5, 0.33, or 0.25 or less than the diameter of the delivery orifice of the injector.

In some embodiments, the preparation further includes hyaluronic acid.

In some embodiments, the concentration of protein in said preparation is less than about 100 mg/ml or is between about 2 and about 50 mg/ml.

In some aspects, the disclosure features a method of delivering a crystallized protein preparation to a subject. The method includes supplying a crystallized protein preparation disposed in a needle-free injector and injecting the preparation into the subject.

In some embodiments, the preparation is a solution of crystals.

In some embodiments, the said crystals are cross-linked.

In some embodiments, the crystals are complexed with a polyelectrolyte, e.g., polyarginine.

In some embodiments, the preparation is of hGH or an hGH derivative. In some embodiments, the preparation is an hGH or an hGH derivative preparation described herein.

In some embodiments, the preparation is not a vaccine.

In some embodiments, the crystals in said preparation have an average largest dimension of 0.5, 0.33, or 0.25 or less than the diameter of the delivery orifice of the injector.

In some embodiments, the preparation further includes hyaluronic acid.

In some embodiments, the concentration of protein in said preparation is less than about 100 mg/ml or is between about 2 and about 50 mg/ml.

In some aspects, the disclosure features a lyophilized preparation of hGH or an hGH derivative, wherein upon resuspension, the preparation provides a suspension that contains: hGH or hGH derivative crystal suspension (e.g., poly-arginine complexed hGH crystal suspension), a buffer, a salt, and polyethylene glycol.

In some embodiments, the crystal suspension is present in an amount between about 20 to about 50 mg/ml.

In some embodiments, the buffer comprises Tris.

In some embodiments, the buffer comprises phosphate. In some embodiments, the buffer further includes Tris or histidine.

In some embodiments, the pH of the suspension is between about 7 and about 9.

In some embodiments, the salt comprises sodium chloride or sodium acetate. In some embodiments, the salt is present in an amount between about 50 mM to about 100 mM.

In some embodiments, the polyethylene glycol comprises polyethylene glycol 3350, 6000 or 8000. In some embodiments, the polyethylene glycol is present in an amount between about 2.5% and about 10%.

In some embodiments, the suspension comprises: about 20 to about 50 mg/mL hGH crystal suspension; Tris or a combination buffer of phosphate with either Tris or histidine; at a pH between about 7 and about 9; sodium chloride or sodium acetate in an amount between about 50 mM to about 100 mM; and polyethylene glycol 3350, 6000 or 8000 in an amount between about 2.5% and about 10%.

In some embodiments, the preparation also contains a preservative. In some embodiments, the preservative is phenol, m-cresol, chlorobutanol, or benzyl alcohol (e.g., preferably phenol, m-cresol, or chlorobutanol, more preferably phenol).

In some embodiments, the suspension is disposed in a siliconized vials or coated surface container closure.

In some aspects, the disclosure features a process for producing lyophilized crystalline hGH. The method includes:

a primary drying cycle of about −30° C. to about 10° C.

In some embodiments, the process further includes a 2nd drying cycle of about 20° C. to about 40° C.

In some embodiments, the disclosure features a lyophilized crystalline hGH product produced by a process described herein.

In some aspects, the disclosure features a lyophilized preparation of hGH containing 25 mg/mL poly-Arg complexed hGH crystals, 25 mM Tris, 100 mM Na Acetate, 5% PEG6000, pH 7.5.

In some aspects, the disclosure features a lyophilized preparation of hGH consisting of 25 mg/mL poly-Arg complexed hGH crystals, 25 mM Tris, 100 mM Na Acetate, 5% PEG6000, pH 7.5.

In some aspects, the disclosure features a lyophilized preparation of hGH containing 25 mg/mL poly-Arg complexed hGH crystals, 25 mM Tris, 0.2% HA, 100 mM Na Acetate, 5% PEG6000, pH 7.5.

In some aspects, the disclosure features a lyophilized preparation of hGH consisting of 25 mg/mL poly-Arg complexed hGH crystals, 25 mM Tris, 0.2% HA, 100 mM Na Acetate, 5% PEG6000, pH 7.5.

In some aspects, the disclosure features a lyophilized preparation of hGH containing 25 mg/mL poly-Arg complexed hGH crystals, 25 mM Tris, 5% PEG6000, pH 7.0.

In some aspects, the disclosure features a lyophilized preparation of hGH consisting of 25 mg/mL poly-Arg complexed hGH crystals, 25 mM Tris, 5% PEG6000, pH 7.0.

In some aspects, the disclosure features a lyophilized preparation of hGH containing 25 mg/mL poly-Arg complexed hGH crystals, 25 mM Tris, 5% PEG6000, pH 7.5.

In some aspects, the disclosure features a lyophilized preparation of hGH consisting of 25 mg/mL poly-Arg complexed hGH crystals, 25 mM Tris, 5% PEG6000, pH 7.5.

In some aspects, the disclosure features a lyophilized preparation of hGH containing 25 mg/mL poly-Arg complexed hGH crystals, 25 mM Tris, 5% PEG8000, pH 7.5.

In some aspects, the disclosure features a lyophilized preparation of hGH consisting of 25 mg/mL poly-Arg complexed hGH crystals, 25 mM Tris, 5% PEG8000, pH 7.5.

In some aspects, the disclosure features a lyophilized preparation of hGH containing 25 mg/mL poly-Arg complexed hGH crystals, 25 mM Tris, 5% PEG3350, pH 7.5.

In some aspects, the disclosure features a lyophilized preparation of hGH consisting of 25 mg/mL poly-Arg complexed hGH crystals, 25 mM Tris, 5% PEG3350, pH 7.5.

In some aspects, the disclosure features a lyophilized preparation of hGH containing 25 mg/mL poly-Arg complexed hGH crystals, 25 mM Tris, 100 mM NaCl, 5% PEG6000, pH 7.5.

In some aspects, the disclosure features a lyophilized preparation of hGH consisting of 25 mg/mL poly-Arg complexed hGH crystals, 25 mM Tris, 100 mM NaCl, 5% PEG6000, pH 7.5.

In some aspects, the disclosure features a lyophilized preparation of hGH containing 25 mg/mL poly-Arg complexed hGH crystals, 25 mM Tris, 100 mM NaCl, 5% PEG8000, pH 7.5.

In some aspects, the disclosure features a lyophilized preparation of hGH consisting of 25 mg/mL poly-Arg complexed hGH crystals, 25 mM Tris, 100 mM NaCl, 5% PEG8000, pH 7.5.

In some aspects, the disclosure features a lyophilized preparation of hGH containing 25 mg/mL poly-Arg complexed hGH crystals, 25 mM Tris, 100 mM NaCl, 5% PEG3350, pH 7.5.

In some aspects, the disclosure features a lyophilized preparation of hGH consisting of 25 mg/mL poly-Arg complexed hGH crystals, 25 mM Tris, 100 mM NaCl, 5% PEG3350, pH 7.5.

In some aspects, the disclosure features a lyophilized preparation of hGH containing 25 mg/mL poly-Arg complexed hGH crystals, 25 mM histidine, 100 mM NaCl, 5% PEG6000, pH 7.0.

In some aspects, the disclosure features a lyophilized preparation of hGH consisting of 25 mg/mL poly-Arg complexed hGH crystals, 25 mM histidine, 100 mM NaCl, 5% PEG6000, pH 7.0.

In some aspects, the disclosure features a lyophilized preparation of hGH containing 25 mg/mL poly-Arg complexed hGH crystals, 25 mM Tris, 1% sucrose, 5% PEG6000, pH 7.5.

In some aspects, the disclosure features a lyophilized preparation of hGH consisting of 25 mg/mL poly-Arg complexed hGH crystals, 25 mM Tris, 1% sucrose, 5% PEG6000, pH 7.5.

In some aspects, the disclosure features a resuspended lyophilate described herein.

In some aspects, the disclosure features a method of delivering a hGH preparation to a patient. The method includes: providing a lyophilized hGH preparation described herein, and administering the preparation (e.g., after resuspending the lyophilate), e.g., by injection, to said patient, e.g., no more than once every 2, 3, 4, 5, 6, 7, 8, 9, or 10 days.

Unless otherwise defined, all technical and scientific terms used herein have the same meaning as commonly understood by one of ordinary skill in the art to which this disclosure belongs. Although methods and materials similar or equivalent to those described herein can be used in the practicing or testing of the present disclosure, suitable materials and methods are described below.

All cited publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

FIG. 7A shows the results obtained with a 1 ml deliver volume subjected to invert treatment; FIG. 7B shows the results obtained with a 1 ml deliver volume subjected to swirl treatment; FIG. 7C shows the results obtained with a 0.2 ml deliver volume subjected to invert treatment; FIG. 7D shows the results obtained with a 0.2 ml deliver volume subjected to swirl treatment.

FIG. 8A shows the results obtained with a 1 ml deliver volume subjected to invert treatment; FIG. 8B shows the results obtained with a 1 ml deliver volume subjected to swirl treatment; FIG. 8C shows the results obtained with a 0.2 ml deliver volume subjected to invert treatment; FIG. 8D shows the results obtained with a 0.2 ml deliver volume subjected to swirl treatment.

DETAILED DESCRIPTION

Overview: Crystalline hGH Stability

Figure 1:
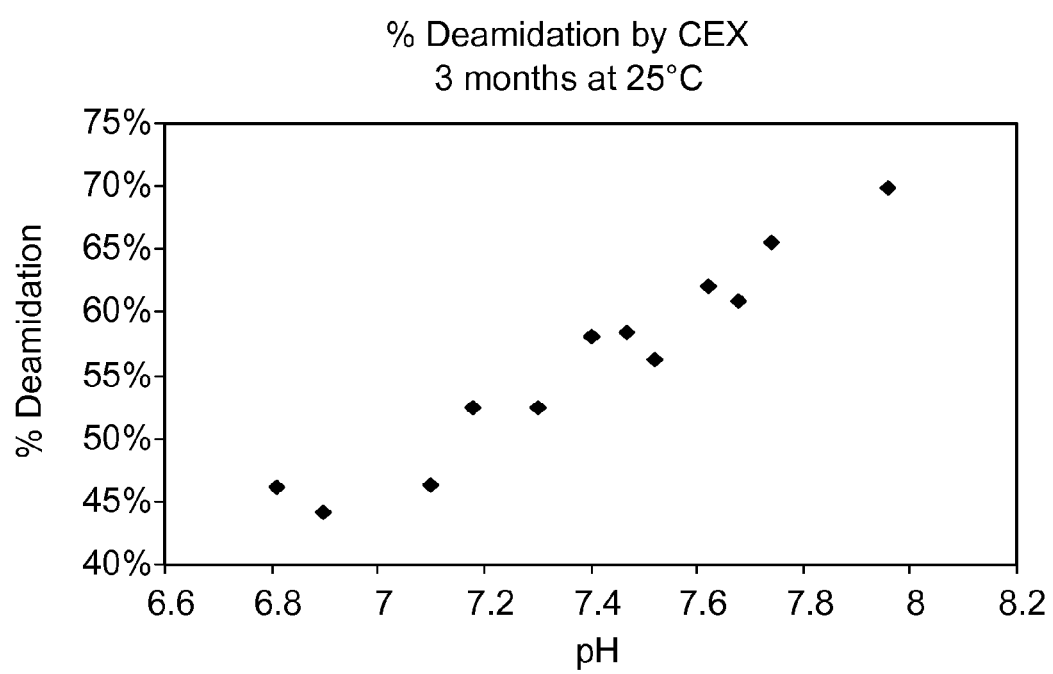
FIG. 1 is a graph showing the correlation of pH with the percentage of degradation by CEX: 3 month 25° C. data was used for the correlation.

Over time, crystalline hGH suspensions can develop soluble protein aggregates, the hGH can undergo oxidation, deamidation, chemical degradation, and crystal form changes, and the hGH can dissolve in solution.

The disclosure provides crystalline hGH suspensions, e.g., poly-arginine complexed hGH crystals suspensions, that have increased stability. Embodiments described herein include one or more measures to address one or more stability issues. As examples, various factors have been addressed to increase the stability of crystalline hGH formulations, e.g., protein concentration, buffer selection, salt selection and concentration, pH, choice and concentration of suspending agents, storage container selection, choice and concentration of preservatives, and fill volume. One, two, three, four, or all of these factors can be altered or controlled to increase the stability of a protein of interest.

As one example of a liquid suspension of crystalline hGH with improved stability, the suspension can have one or more of the following properties: contain about 5-50 mg/ml hGH crystal suspension; contain a phosphate-containing buffer; contained in a pH range of about 6.1 to about 6.8; contain sodium chloride or sodium acetate at a concentration of about 60 mM to about 200 mM; contain polyethylene glycol 6000 or 8000 at about 2.5% to about 20%; be aliquoted at a fill volume of about 0.2 to about 1 ml; be disposed in a siliconized prefilled syringe with limited head space (e.g., no head space to about 10 mm head space) or in another cylinder type of container or device with limited head space.

As one example, the disclosure provides a formulation of crystalline hGH suspension that is stable for 18 to 24 months at 5±3° C. (refrigerated) and at least one month at room temperature 25±2° C. (in use) conditions.

Formulations described herein, e.g., liquid formulations containing a crystalline protein (e.g., poly-Arg complexed crystalline hGH), have increased stability. E.g., upon storage in a container, at a temperature of 2-8° C. for a period of up to 3, 6, 9, 12, or 24 months (or in some embodiments longer), a protein in the composition will retain at least 50, 75, 85, 90, 95, or 100% of the stability it had prior to storage (e.g., the protein can retain about 77% of the stability at 25° C. over a period of three months). Stability, as used herein, includes parameters such as protein structure (e.g., minimizing or preventing changes in protein structure, e.g., protein aggregation or protein degradation) and/or efficacy of the protein, e.g., therapeutic efficacy (e.g., ability to cause an increase in body weight).

As used herein, the term "increased stability" refers to a decrease (e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, or about 99% decrease) in the amount of protein deamidation, protein oxidation, protein aggregation, protein dissolution, or therapeutic efficacy over a fixed period of time under testing or fixed storage conditions Human Growth Hormone The term "growth hormone (GH)" refers generally to growth hormones secreted by the pituitary gland in mammals. Although not an exhaustive list, examples of mammals include human, apes, monkey, rat, pig, dog, rabbit, cat, cow, horse, mouse, rat and goat. According to a preferred embodiment of this disclosure, the mammal is a human.

"Human growth hormone (hGH)" denotes a protein having an amino acid sequence, structure and function characteristic of native human growth hormone. As used herein, human growth hormone (hGH) also includes any isoform of native human growth hormone, including but not limited to, isoforms with molecular masses of 5, 17, 20, 22, 24, 36 and 45 kDa (Haro et al., J. Chromatography B, 720, 39-47 (1998)). Thus, the term hGH includes the 191 amino acid sequence of native hGH, somatotropin, and the 192 amino acid sequence containing an N-terminal methionine (Met-hGH) and somatrem (U.S. Pat. Nos. 4,342,832 and 5,633,352). hGH may be obtained by isolation and purification from a biological source or by recombinant DNA methods. If made by recombinant DNA methodology, hGH is denoted as recombinant human growth hormone (rhGH). Met-hGH is typically prepared by recombinant DNA methodology.

The term "human growth hormone derivative" refers to a protein that differs by at least about 1% but not by more than about 20% from the amino acid sequence of the 191 amino acid sequence of hGH or the 192 amino acid-sequence of Met-hGH. For example, the derivative can differ by about 1% to about 20%, about 2% to about 15%, or about 5% to about 10% from the 191 amino acid sequence of hGH or the 192 amino acid-sequence of Met-hGH; the protein can differ by about 1%, about 2%, about 3%, about 4%, about 51%, about 6%, about 7%, about 8%, about 9%, about 10%, about 11%, about 12%, about 13%, about 14%, or about 15% from the 191 amino acid sequence of hGH or the 192 amino acid-sequence of Met-hGH. The differences between the derivative and the 191 amino acid hGH or the 192 amino acid Met-hGH amino acid sequence can be one or more substitutions (e.g., conservative or non conservative substitutions), deletions, additions (e.g., insertions or amino- or carboxyterminal additions)), modifications, or combinations thereof. In some embodiments, the derivative maintains a biological activity and/or a chemical and/or physical property of the 191 amino acid hGH or the 192 amino acid Met-hGH amino acid sequence. Likewise, in some embodiments, a formulation containing a derivative (e.g., a formulation of poly-Arg complexed crystalline hGH derivative) possesses a chemical and/or physical property of a similarly-prepared formulation containing the 191 amino acid hGH or the 192 amino acid Met-hGH amino acid sequence (e.g., a formulation of poly-Arg complexed crystalline hGH).

In various embodiments of the present disclosure, human growth hormone derivatives comprise organic cations of hGH or Met-hGH, substitution, deletion and insertion variants of biologically synthesized hGH or Met-hGH proteins, post-translationally modified hGH and Met-hGH proteins, including deamidation, phosphorylation, glycoslylation, acetylation, aggregation and enzymatic cleavage reactions [Haro et al., J. Chromatography B, 720, 39-47 (1998)], chemically modified hGH or Met-hGH proteins derived from biological sources, polypeptide analogs and chemically synthesized peptides containing amino acid sequences analogous to those of hGH or Met-hGH.

Methods used to prepare hGH or Met-hGH include isolation from a biological source, recombinant DNA methodology, synthetic chemical routes or combinations thereof. To date, genes that encode for different DNA sequences of hGH include hGH-N and hGH-V [Haro et al., J. Chromatography B, 720, 39-47 (1998); Bennani-Baiti et al., Genomics, 29, 647-652 (1995)].

The term "valency" is defined as an element's ability to combine with other elements and which is dictated by the number of electrons in the outermost shell of the atom and expressed as the number of atoms of hydrogen (or any other standard univalent element) capable of uniting with (or replacing) its atoms [Webster's New World Dictionary of Science, Lindley, D. and Moore T. H., Eds., Macmillan, New York, N.Y., 1998]. The terms "monovalent cation" and "divalent cation" refer to ions carrying a positive charge that have either a valence state of one or two, respectively. Cations having different valence states can be organic or inorganic in nature. Examples of monovalent inorganic cations include ammonium ($NH_4^+$) and Group I elements of the periodic table ($H^+$, $Li^+$, $Na^+$, $R^{30}$, $Cs^+$ and $Fr^+$) and divalent inorganic cations include Group II elements ($Be^{2+}$, $Mg^{2+}$, $Ca^{2+}$, $Sr^{2+}$, $Ba^{2+}$, $Mn^{2+}$, $Co^{2+}$, $Ni^{2+}$, $Cu^{2+}$, $Zn^{2+}$, $Cd^{2+}$, $Mo^{2+}$ and $Ra^{2+}$).

"Organic cation crystal of human growth hormone or a human growth hormone derivative" refers to human growth hormone that has been crystallized in the presence of an organic cation. The term "organic cation" refers to a positively charged atom or group of atoms that contain carbon. Examples of organic cations include quaternary ammonium cations, tetraethylammonium (TEA), tributylmethylammonium (TBuMA), procainamide ethobromide (PAEB), azidoprocainamide methoiodide (APM), d-tubocurarine, metocurine vecuronium, rocuronium, 1-methyl-4-phenylpyridinium, choline and N-(4,4-axo-n-pentyl)-21-deoxyajm-alinium (APDA).

hGH is commercially available in lyophilized form and is typically produced by recombinant DNA methods. Crystallization of hGH can be accomplished by preparing a buffered solution of hGH, purifying and/or desalting, dialyzing and concentrating the solution and adding a monovalent or divalent cation or salt to the solution. The latter step results in the formation of an organic or inorganic cation bound to hGH.

One preferred embodiment of this disclosure relates to monovalent cation crystals of hGH or an hGH derivative. In a more preferred embodiment, the monovalent cation is selected from the group consisting of: lithium, sodium, potassium and ammonium. In a most preferred embodiment, the monovalent cation is sodium. In a most preferred embodiment, human growth hormone or a human growth hormone derivative comprises from about 1 to about 500 monovalent cation molecules per monomer or monomer chain of human growth hormone or human growth hormone derivative.

The term "monovalent cation salt" includes both inorganic and organic counterions or molecules that from an ionic bond with the monovalent ion. In a preferred embodiment, the monovalent cation salt is a sodium salt. In a more preferred embodiment, the sodium salt is selected from the group consisting of sodium citrate, sodium phosphate and sodium acetate. In a most preferred embodiment, the sodium salt is sodium acetate.

In one preferred embodiment, crystalline hGH or crystalline hGH derivative complexed with protamine is provided. Likewise, in another preferred embodiment, crystalline hGH or crystalline hGH derivative complexed with polyarginine is provided.

A crystallization and complexation process for hGH to produce long-acting hGH has been developed, and this product has demonstrated a controlled release profile in clinical trials (see US application 2004-0209804, WO 2004/060310, WO 2004/060920). Poly-arginine (poly-Arg) complexation results in an improved controlled release profile. This drug delivery method is designed for fewer injections without the use of polymers or fusion proteins to offer a more user-friendly treatment alternative for patients. The uniqueness of this crystallization technology is that little or no increase of soluble aggregates is observed since limited free hGH is present in the supernatant.

For example, poly-Arg crystalline hGH can be prepared as follows:

A frozen bulk feed solution of soluble recombinantly-produced hGH (rhGH) is obtained, e.g., derived from E. coli (Novartis) or from yeast (Lucky Gold).

Approximately 3.5 ml (12 mg/ml rhGH in Tris-HCl (10 mM, pH 8.0)) of thawed rhGH feed solution is purified using a 10DG-desalting column supplied by Biorad. Prior to sample loading, the column is conditioned by washing the column with 30 ml of Tris-HCl (10 mM, pH 8.0). The rhGH sample is then loaded and allowed to enter the column by gravity. After discarding the first three ml of eluant, another 5.0 ml of 10 mM Tris-HCl pH 8.0 is then added. 4.5 ml of the desalted rhGH is eluted and collected. Concentration by centrifugation is then performed using a Millipore concentrator (MWCO 10,000) at 3500 rpm for 20-30 min. The concentration of hGH is in the range of 30 mg/ml as measured by absorbance at 280 nm/0.813 (1 mg/ml hGH A280=0.813 absorbance units). Crystals are grown by adding 1M Tris-HCl (pH 8.6), 50% PEG-6000 and 1M Ca-acetate to the rhGH 30 mg/ml stock preparation so that a final concentration of 15 mg/ml rhGH, 100 mM Tris-HCl (pH 8.6), 2% (v/v) PEG-6000 and 85 mM Ca-acetate is obtained. The solution is then mixed gently and incubated at 33° C. for 12-16 hours. Needle-like-crystals are obtained ranging in length from approximately 2 to 25 μm. After extracting the supernatant and centrifuging and pelleting the crystals, crystallization yield is measured, e.g., the yield can be greater than 85%. The crystals can also be formed at temperatures between 33° C. and 15° C. but require increased crystallization time and may have a reduced yield. After crystallization, yield is determined, calcium rhGH crystals are re-suspended in a formulation vehicle (e.g., 5 mM CaOAc, 100 mM Tris-HCl (pH 8.6), 6% PEG-6000, and 4.2 mg/ml polyarginine) so that a final concentration of 21 mg/ml or 25 mg/ml of calcium rhGH crystals is achieved. The protein to additive ratio for rhGH to polyarginine was 5:1 (mg:mg). These ratios are calculated to be mole ratios of approximately 1:0.587 for rhGH:polyarginine. The above rhGH pellets are homogenously re-suspended in the appropriate mother liquor and incubated overnight at 2-8° C. before being centrifuged to obtain a condensed pellet. The supernatants are removed and the pellets can be re-suspended in the same mother liquor without ionic additive and can be stored at 4° C.

A further preferred embodiment of this disclosure includes monovalent or divalent crystals of hGH or an hGH derivative complexed or co-crystallized with protamine or polyarginine. More preferably, the crystals are sodium crystals complexed or co-crystallized with protamine or polyarginine.

The soluble form of hGH may be characterized by a variety of methods, including reversed phase high performance liquid chromatography (RP-HPLC), size exclusion chromatography high performance liquid chromatography (SEC-HPLC) and hydrophobic interaction chromatography (HIC) (Wu et al., J. Chromatography, 500, 595-606 (1990); "Hormone Drugs", FDA publication, (1982)). On the other hand, the crystalline form of hGH may be characterized by optical microscopy and X-ray diffraction. In general, the conditions of crystallization will determine the shape of a protein crystal, i.e., a shape selected from the group consisting of spheres, needles, rods, plates (hexagonals and squares), rhomboids, cubes, bipyramids and prisms.

Crystals of hGH or an hGH derivative according to this disclosure form rod-like or needle-like morphologies when imaged with optical microscopy. In one embodiment, crystals of hGH or an hGH derivative form rods or needles that are between about 0.1 and about 200 μm in length. In a preferred embodiment, crystals of hGH or an hGH derivative form rods or needles that are between about 3 and about 100 μm in length. In a more preferred embodiment, crystals of hGH or an hGH derivative form rods or needles that are between about 10 and about 25 μm in length.

ALTU-238 is a ready to use suspension of hGH crystals complexed with poly-L-Arginine in a formulation vehicle that is long-acting (e.g., provides week-long release of hGH after subcutaneous administration through a 29-guage or finer needle). The formulation of ALTU-238 is 25 mg/mL rhGH, 5 mg/mL poly-Arg, 25 mM Tris, 100 mM Na Acetate, 5% w/v PEG 6000 pH 7.5, which can be used, e.g., as a standard for comparison studies to assess the stability of the formulations described herein.

Two formulations, liquid and lyophilized, can be prepared with poly-L-Arginine complexed with hGH crystals. Descriptions of each are provided.

Liquid Suspension Formulation

Formulation Vehicle

The combination of pH, buffer, salt, suspending agent, hyaluronic acid ("HA") and/or preservative in which the poly-Arg complexed hGH crystals are suspended can be referred to as the "formulation vehicle." Each of the components of the vehicle can be varied separately or in combination and optimized to result in a suspension of complexed hGH crystals with desired properties, e.g., increased stability.

pH

The pH of a suspension can be a major factor affecting the stability of hGH complexed crystals (a suspension of poly-Arg-complexed hGH crystals). For example, the pH of the suspension can affect the deamidation and oxidation of the hGH complexed crystals. In some embodiments, a pH above about 7.0 or 7.5 (depending on other formulation conditions) can cause increases in both protein deamidation (FIG. 1) and oxidation. Deamidation can be measured, e.g., by cation exchange HPLC (CEX-HPLC). Oxidation can be measured, e.g., by reverse phase HPLC (RP-HPLC). pH below about 5.5 or about 5.0 can lead to protein turbidity, e.g., depending on other properties of the suspension. Turbidity can be measured, e.g., by UV absorbance readings at 320 nm.

In some embodiments, the pH of the suspension is between about 6 and about 7.5. In preferred embodiments, the pH is between 6.1 and 6.8. For example, the pH can be about 6.1, about 6.3, about 6.5, or about 6.8.

One can test a candidate pH by providing a poly-Arg complexed crystalline rhGH suspension that contains 25 mg/mL rhGH, 5 mg/mL poly-Arg, 25 mM Tris, 100 mM Na Acetate, 5% w/v PEG 6000 at a candidate pH value. The stability of the suspension at the candidate pH, measured, e.g., as a percent oxidation or degradation, at a predetermined time is compared with one or more standards. For example, a suitable standard would be a suspension similar to the test conditions except that the pH of the suspension is not adjusted, e.g., the pH of the standard can be 7.5. The stabilities of the test (the suspension adjusted to the candidate pH) and standard (the pH is not adjusted) suspensions are compared. Suitability can be shown by the test suspension increasing stability (e.g., as measured by a smaller amount of oxidation or deamidation) as compared with the standard. Another standard can be a suspension similar to the test suspension except that in place of the candidate pH, the suspension has another pH described herein, for example, pH 6.5. Suitability can be shown by the suspension at the candidate pH having comparable or better effects on stability than the suspension at pH 6.5.

Buffer

The buffer used to make a suspension can be a major factor affecting the stability of hGH complexed crystals (a suspension of poly-Arg-complexed hGH crystals). For example, the buffer of the suspension can affect the crystal size and turbidity (e.g., due to insoluble aggregates) of the suspension of hGH complexed crystals. Turbidity can be measured, e.g., by UV absorbance readings at 320 nm.

Crystal size can be evaluated, e.g., by microscopy and by laser diffraction particle size counter.

In some embodiments, the buffer can be phosphate buffer, glycine buffer, histidine buffer, citrate buffer, acetate buffer, or Tris buffer. In preferred embodiments, the buffer is histidine buffer, citrate buffer, or Tris buffer. In more preferred embodiments, the buffer is phosphate buffer. The concentration of the buffer can also be varied, e.g., the concentration of the buffer components, e.g., phosphate, glycine, histidine, citrate, acetate, or Tris can be varied.

One can test a candidate buffer by providing a poly-Arg complexed crystalline rhGH suspension that contains 25 mg/mL rhGH, 5 mg/mL poly-Arg, 100 mM Na Acetate, 5% w/v PEG 6000 at pH 6.5 in a test buffer. The stability of the suspension in the candidate buffer, measured, e.g., as the amount of turbidity, at a predetermined time is compared with one or more standards. For example, a suitable standard would be a composition similar to the test conditions except that the buffer of the composition is a buffer described herein, e.g., the buffer of the standard can be phosphate buffer. The stabilities of the test (the suspension in the test buffer) and standard (the suspension in phosphate buffer) suspensions are compared. Suitability can be shown by the test suspension increasing stability (e.g., as measured by a smaller amount of turbidity) as compared with the standard. Another standard can be a suspension similar to the test suspension except that in place of the candidate buffer, the suspension has another buffer described herein, for example, Tris buffer. Suitability can be shown by the suspension in the candidate buffer having comparable or better effects on stability than the suspension in phosphate buffer. As another example, the concentration of the buffer can also be tested, e.g., the stability (e.g., turbidity) of a suspension in Tris at a test concentration, e.g., 50 mM, can be compared to a suspension in Tris at a standard concentration described herein, e.g., 25 mM. Suitability can be shown by the suspension in the candidate concentration having comparable or better effects on stability than the suspension in standard concentration.

Salt

The salt used in a suspension can be a major factor affecting the stability of hGH complexed crystals (a suspension of poly-Arg-complexed hGH crystals). For example, the salt content in the suspension can affect the deamidation rate and/or levels in the suspension of hGH complexed crystals. As an example, higher salt content (e.g., increasing ionic strength) can lead to less deamidation. Deamidation can be measured, e.g., by cation exchange HPLC (CEX-HPLC).

In some embodiments, the salt can be a sodium salt such as sodium chloride or sodium acetate. In preferred embodiments, sodium chloride is used in the suspension. The salt concentration can also be varied, e.g., the concentration can be from about 1 mM to about 200 mM, e.g., from about 60 mM to about 200 mM.

One can test a candidate buffer by providing a poly-Arg complexed crystalline rhGH suspension that contains a test salt, 25 mg/mL rhGH, 5 mg/mL poly-Arg, 5% w/v PEG 6000 at pH 6.5 in phosphate buffer. The stability of the suspension with the candidate salt, measured, e.g., as the amount of deamidation, at a predetermined time is compared with one or more standards. For example, a suitable standard would be a composition similar to the test conditions except that the salt of the composition is a salt described herein, e.g., the salt of the standard can be sodium chloride. The stabilities of the test (the suspension with the test salt) and standard (the suspension with sodium chloride) suspensions are compared. Suitability can be shown by the test suspension increasing stability (e.g., as measured by a smaller amount of deamidation) as compared with the standard. Another standard can be a suspension similar to the test suspension except that in place of the candidate salt, the suspension has another salt described herein, for example, sodium acetate. Suitability can be shown by the suspension with the candidate salt having comparable or better effects on stability than the suspension with sodium acetate. As another example, the concentration of the given salt can also be tested, e.g., the stability (e.g., deamidation) of a suspension with sodium chloride at a test concentration, e.g., 20 mM, can be compared to a suspension with sodium chloride at a standard concentration described herein, e.g., 60 mM. Suitability can be shown by the suspension with the candidate concentration having comparable or better effects on stability than the suspension in standard concentration.

Suspending Agent

The suspending agent used in a suspension can be a major factor affecting the stability of hGH complexed crystals (a suspension of poly-Arg-complexed hGH crystals). For example, the suspending agent in the suspension can affect the rate of chemical degradation and/or deamidation rate and/or levels in the suspension of hGH complexed crystals. No or low amounts of suspending agent can lead to caking of the suspension. Chemical degradation can be measured, e.g., by RP-HPLC. Deamidation can be measured, e.g., by cation exchange HPLC (CEX-HPLC).

In some embodiments, the suspending agent can be a polyethylene glycol, mannitol, glycine, or sucrose. In preferred embodiments, the suspending agent can be a polyethylene glycol, mannitol, or glycine. In more preferred embodiments, the suspending agent is a polyethylene glycol such as PEG3350, PEG6000, or PEG8000. The amount of the suspending agent can also be varied, e.g., the amount can be from about 2.5% to about 20%.

One can test a candidate suspending agent by providing a poly-Arg complexed crystalline rhGH suspension that contains a test suspending agent, 25 mg/mL rhGH, 5 mg/mL poly-Arg, 100 mM Na Acetate, at pH 6.5 in phosphate buffer. The stability of the suspension with the candidate suspending agent, measured, e.g., as the amount of deamidation, at a predetermined time is compared with one or more standards. For example, a suitable standard would be a composition similar to the test conditions except that the suspending agent of the composition is a suspending agent described herein, e.g., the standard can be PEG8000. The stabilities of the test (the suspension with the test suspending agent) and standard (the suspension with PEG8000) suspensions are compared. Suitability can be shown by the test suspension increasing stability (e.g., as measured by a smaller amount of deamidation) as compared with the standard. Another standard can be a suspension similar to the test suspension except that in place of the candidate suspending agent, the suspension has another suspending agent described herein, for example, PEG6000. Suitability can be shown by the suspension with the candidate suspending agent having comparable or better effects on stability than the suspension with PEG6000. As another example, the concentration of the given suspending agent can also be tested, e.g., the stability (e.g., deamidation) of a suspension with PEG at a test amount, e.g., 25%, can be compared to a suspension with PEG at a standard concentration described herein, e.g., 5%. Suitability can be shown by the suspension with the candidate amount having comparable or better effects on stability than the suspension in standard amount.

hGH Concentration

The concentration of poly-Arg complexed crystals in a suspension can be a another factor affecting the stability of hGH complexed crystals (a suspension of poly-Arg-complexed hGH crystals). For example, at higher concentrations, the suspension may become thick. Protein stability can be assayed by RP-HPLC for oxidation levels or rates. Stability can also be measured by cation exchange HPLC (CEX-HPLC) for deamidation levels or rates.

In some embodiments, the concentration can be about 5 to about 50 mg/ml. In preferred embodiments, the concentration is about 20 to about 30 mg/ml.

One can test a candidate concentration by providing a poly-Arg complexed crystalline rhGH suspension that contains a test concentration of rhGH, 5 mg/mL poly-Arg, 100 mM Na Acetate, 5% w/v PEG 6000 at pH 6.5 in phosphate buffer. The stability of the suspension at the candidate concentration, measured, e.g., as the amount of deamidation, at a predetermined time is compared with one or more standards. For example, a suitable standard would be a composition similar to the test conditions except that the concentration of the composition is a concentration described herein, e.g., about 35 mg/ml. The stabilities of the test (the suspension at the test concentration) and standard (the suspension at 25 mg/ml) suspensions are compared. Suitability can be shown by the suspension at the candidate concentration having comparable or better effects on stability (e.g., as measured by a smaller amount of deamidation) as compared with the standard.

hGH to Poly-Arg Ratio

The ratio of hGH to poly-Arg in the complexed crystals in a suspension can be a another factor affecting the stability of the crystals. For example, it is possible that at lower hGH to poly-Arg ratios, the degradation level may be higher than at higher hGH to poly-Arg ratios (e.g., ration of 7). Degradation can be measured, e.g., by reverse phase HPLC (RP-HPLC).

In some embodiments, the hGH to poly-Arg ratio can be about 3 to about 15. In preferred embodiments, the ratio is about 7 to about 11.

One can test a candidate ratio by providing a poly-Arg complexed crystalline rhGH suspension that contains test amounts of poly-Arg to alter the hGH to poly-Arg ratio, 25 mg/ml rhGH, 100 mM Na Acetate, 5% w/v PEG 6000 at pH 6.5 in phosphate buffer. The stability of the suspension at the candidate ratio, measured, e.g., as the amount of oxidation, at a predetermined time is compared with one or more standards. For example, a suitable standard would be a composition similar to the test conditions except that the ratio of hGH to poly-Arg of the composition is a ratio described herein, e.g., 5 (i.e., the poly-Arg is present at a concentration of 5 mg/ml). The stabilities of the test (the suspension at the test ration) and standard (the suspension with a ratio of 5) suspensions are compared. Suitability can be shown by the suspension at the candidate ratio having comparable or better effects on stability (e.g., as measured by lower oxidation levels) as compared with the standard.

Storage Container and Container Closure

The choice of container used to store a suspension and/or the choice of container closure can affect the stability of hGH complexed crystals (a suspension of poly-Arg-complexed hGH crystals). For example, the choice of container and/or closure can affect dose consistency or product loss. For example, crystals can accumulate in the in the bottle neck of the vial or accumulate on the closure (e.g., on the walls of the closure). Further, the shape of the container and/or the closure can also affect dose consistency. Dose consistency can be measured, e.g., by measuring the amount of recovered hGH concentration or by measuring the extractable weight, e.g., after agitating the samples.

In some embodiments, vials and prefilled syringes made with various materials, e.g., siliconized, plastic (e.g., CZ) resin, or polypropylene vials are used. In some embodiments, the closure can be a Teflon coated stopper (e.g., a Diekyo Fluorotec stopper) or a rubber stopper, e.g., a butyl rubber stopper, e.g., West 4432/50. In preferred embodiments, siliconized containers, especially cylindrical siliconized or coated-surface containers, are used. In more preferred embodiments, siliconized prefilled syringes are used. In preferred embodiments, Teflon or butyl rubber stoppers are used as the closures.

One can test a candidate container by providing a poly-Arg complexed crystalline rhGH suspension that contains 25 mg/ml rhGH, 5 mg/ml poly-Arg, 100 mM Na Acetate, 5% w/v PEG 6000 at pH 6.5 in phosphate buffer in a test container. The stability of the suspension in the candidate container, measured, e.g., as the amount of extactable weight, at a predetermined time is compared with one or more standards. For example, a suitable standard would be the composition stored in a container described herein, e.g., a prefilled syringe. The stabilities of the suspension in the candidate container and the standard container are compared. Suitability can be shown by the suspension in the candidate container having comparable or better effects on stability (e.g., as measured by weight recovery) as compared with the standard.

Candidate container closures can be evaluated in a like manner.

Head Space

Finally, the head space in the container can also affect protein stability. For example, the head space of container closure can have a significant impact on delivered dose consistency.

In some embodiments, prefilled syringes with stake needles are preferred because of the limited dead volume (range from 2 to 5 μL) for hGH complexed crystals or any protein crystals products. There is no bottle neck for the prefilled syringes; also, the head space is much smaller and can be controlled by the stopper placement; the plunger can push almost all of the crystal out of the syringe barrel (except the dead volume). Other containers, e.g., vials, can also be used. In preferred embodiments, minimal or no head space is present in the container closure. Companies can fill material with no head space. Limited head space is preferred for container closures used for protein crystals for dose consistency. In a most preferred embodiment, prefilled syringes with stake needles and a head space of less than 10 mm are more suitable for protein crystal parenteral products.

Preservative

Preservatives, e.g., anti-microbial preservatives, can be used in the preparation of multi-dose pharmaceutical formulations. The optional addition of and the concentration of a preservative in a formulation of poly-Arg complexed crystals in suspension can be a factor affecting the stability of hGH complexed crystals (a suspension of poly-Arg-complexed hGH crystals). For example, the presence of a preservative may affect the stability, crystal structure, and/or efficacy (e.g., release profile) of the complexed hGH. Crystal structure can be assayed by microscopy. Release profile can be measured by assaying the concentration of hGH in the formulation supernatant or calculating the percent of free hGH in the formulation.

In some embodiments, the preservative can be phenol, meta-cresol, benzyl alcohol, methyl paraben, clorobutanol. In preferred embodiments, the preservative is phenol or m-cresol. In more preferred embodiments, the preservative is phenol. The amount of the preservative can also be varied, e.g., the amount preferably can be from about 0.1% to about 1%.

One can test a candidate preservative by providing a poly-Arg complexed crystalline rhGH suspension that contains the candidate preservative, 25 mg/ml rhGH, 5 mg/mL poly-Arg, 100 mM Na Acetate, 5% w/v PEG 6000 at pH 6.5 in phosphate buffer. The stability of the suspension with the candidate preservative, measured, e.g., as the concentration of hGH in the formulation supernatant, at a predetermined time is compared with one or more standards. For example, a suitable standard would be a composition similar to the test conditions except that no preservative is present. The stabilities of the test (the suspension with the test the concentration of hGH in the formulation supernatant) and standard (the suspension without a preservative) suspensions are compared. Suitability can be shown by the suspension with the candidate preservative having comparable or better effects on stability (e.g., as measured by a smaller amount of hGH in the supernatant) as compared with the standard. As another example, the concentration of the given preservative can also be tested, e.g., the stability of a suspension with phenol at a test amount, e.g., 2%, can be compared to a suspension with phenol at a standard concentration described herein, e.g., 0.5%. Suitability can be shown by the suspension with the candidate amount having comparable or better effects on stability than the suspension in standard amount.

Hyaluronic Acid

Hyaluronic acid ("HA") can also be included in the formulations described herein. The present disclosure contemplates the use of both HA and salts thereof. For example, HA may neutralize excess crystal charge, thereby reducing potential injection site reactions that may otherwise be caused by the administration of a formulation of complexed hGH crystals. Other advantages can include: contributing to a sustained release profile of complexed crystals after administration to a subject (e.g., human), allowing injection with fine gauged (e.g., very fine gauged, e.g., 30-gauge) needles, preserving crystallinity and integrity of complex over time. In some embodiments, the use of HA does not alter the hGH release profile or in vivo efficacy.

In preferred embodiments, HA is present in the formulation in an amount between about 0.01% and 0.5% (w/v), more preferably about 0.2% (w/v).

One can test a candidate concentration of HA by providing a poly-Arg complexed crystalline rhGH suspension that contains a test concentration of HA, 25 mg/ml rhGH, 5 mg/mL poly-Arg, 100 mM Na Acetate, 5% w/v PEG 6000 at pH 6.5 in phosphate buffer. The stability of the suspension at the candidate concentration, measured, e.g., as the dissolution rate (e.g., measured by size exclusion chromatography), at a predetermined time is compared with one or more standards. For example, a suitable standard would be a composition similar to the test conditions except that the HA concentration of the composition is a concentration described herein, e.g., about 0.2% (w/v). The stabilities of the test (the suspension at the test concentration) and standard (the suspension with 0.2% HA)) suspensions are compared. Suitability can be shown by the suspension at the candidate concentration having comparable or better effects on stability (e.g., as measured by no increase in dissolution rate) as compared with the standard.

Lyophilized Formulation

Lyophilized Formulations of hGH Crystals

Lyophilized hGH or hGH derivative protein formulations (e.g., complexed with poly-Arg) (e.g., after reconstitution of a lyophilized preparation) can increase the stability of the hGH formulation. For example, the lyophilized formulations described herein are predicted to achieve about 24 months or longer chemical stability at refrigerated or room temperatures.

Factors that can affect the stability of the formulation include: the buffer, pH, salt, suspending agent, preservative, and choice of storage container. One, two, three, four, five, or all of these factors can be altered or controlled to increase the stability of a protein of interest.

For example, as described herein, lyophilized formulations of poly-Arg complexed hGH crystals preferably contain one or more of the following: prepared using a buffer (preferably Tris or combination of histidine and phosphate) at the pH range from 7 to 9, a salt (preferably sodium chloride or sodium acetate), and a suspending agent (preferable polyethylene glycol 6000 or 8000). In some formulations, a preservative is also included. The container closure systems that are compatible with these formulations include siliconized or coated vials, such as Schott type I plus coated glass vials.

These components and amounts are suitable for the formulations prior to lyophilization and also for the formulations after the lyophilized hGH is reconstituted. For example, a given volume of a pre lyophilization formulation can have a given composition, e.g., 25 mg/mL poly-Arg complexed hGH crystals, 25 mM Tris, 5% PEG8000, pH 7.5. To reconstitute the crystals post lyophilization, a volume of liquid (e.g., saline or water, preferably water) that is equivalent to the volume of the formulation prior to lyophilization is added to reconstitute the lyophilized preparation. Because the same volume was used, the post lyophilization preparation will have the same or substantially the same composition as the formulation prior to lyophilization. Depending on what liquid was used to reconstitute the preparation, additional components may exist in the post lyophilization preparation (e.g., if saline was used for reconstitution instead of water, the salt concentration may be increased). Optionally, the amount of liquid added for reconstitution can be adjusted to account for pre lyophilization volume contributed by the protein crystals. Thus, a volume of liquid is added to bring the total volume of the post lyophilization formulation to the total volume pre lyophilization. As another alternative, a different (e.g., smaller or larger volume) of liquid can be used for reconstitution to dilute (if a larger volume is used) or concentrate (if a smaller volume is used) the components of the formulation.

Optimization of these factors and suitability determinations can be performed as described above.

Generally, lyophilization (also known as freeze drying) is a dehydration process typically used to preserve a perishable material or make the material more convenient for transport. Freeze drying works by freezing the material and then reducing the surrounding pressure and adding enough heat to allow the frozen water in the material to sublime directly from the solid phase to gas. Products, e.g., proteins or protein crystals, can be lyophilized to make them more stable, or easier to dissolve in water for subsequent use.

A description of a typical lyophilization are as follows. There are three stages in the complete lyophilization process: Freezing, Primary Drying, and Secondary Drying.

Freezing: The freezing process consists of freezing the material. This is often done by placing the material in a freeze-drying flask and rotating the flask in a bath of dry ice and methanol, or liquid nitrogen. On a larger-scale, freezing is usually done using a freeze-drying machine. It is important to freeze the material at a temperature below the eutectic point of the material. Since the eutectic point occurs at the lowest temperature where the solid and liquid phase of the material can coexist, freezing the material at a temperature below this point ensures that sublimation rather than melting will occur in the following steps.

Primary Drying: During the primary drying phase, the pressure is lowered and enough heat is supplied to the material for the water to sublimate. The amount of heat necessary can be calculated using the sublimating molecules' latent heat of sublimation. In this initial drying phase, about 98% of the water in the material is sublimated. This phase may be slow, because if too much heat is added the material's structure could be altered.

In this phase, pressure is controlled through the application of partial vacuum. The vacuum speeds sublimation making it useful as a deliberate drying process. Furthermore, a cold condenser chamber and/or condenser plates provide a surface(s) for the water vapor to re-solidify on. This condenser plays no role in keeping the material frozen; rather, it prevents water vapor from reaching the vacuum pump, which could degrade the pump's performance. Condenser temperatures are often below 10° C., e.g., −30° C. or −50° C., e.g., in ranges below these temperatures.

Secondary Drying: The secondary drying phase aims to sublimate the water molecules that are adsorped during the freezing process, since the mobile water molecules were sublimated in the primary drying phase. This part of the freeze-drying process is governed by the material's adsorption isotherms. In this phase, the temperature is raised even higher than in the primary drying phase to break any physico-chemical interactions that have formed between the water molecules and the frozen material. Usually the pressure is also lowered in this stage to encourage sublimation. However, there are products that benefit from increased pressure as well.

After the freeze drying process is complete, the vacuum is usually broken with an inert gas, such as nitrogen, before the material is sealed.

Properties of Freeze-dried Products: If a freeze-dried substance is sealed to prevent the reabsorption of moisture, the substance may be stored at room temperature without refrigeration, the process can increase the shelf life of pharmaceuticals.

Lyophilization also causes less damage to the substance than other dehydration methods using higher temperatures. Lyophilization does not usually cause shrinkage or toughening of the material being dried.

Lyophilized products can be rehydrated (reconstituted) much more quickly and easily because it leaves microscopic pores. The pores are created by the ice crystals that sublimate, leaving gaps or pores in its place. This is especially important when it comes to pharmaceutical uses.

Analytical Methods

Formulation development can be assessed by the following characteristics: storage stability at various temperatures, container-closure compatibility as a function of dose consistency, potential stickiness, ease of administration of product, and loss to container closure. The stability test methods and their application are listed in Table 1 below:

TABLE 1

Stability test methods and their purposes

| TEST METHODS | APPLICATION |
| --- | --- |
| pH | pH maintenance |
| Appearance | Suspension description |
| Particle Size Distribution | Physical stability |
| Crystal Morphology | Physical stability |
| Purity by Reverse Phase Chromatography (RP-HPLC) | Chemical degradation (oxidation) |
| Purity by Size Exclusion Chromatography (SEC) | Soluble aggregates |
| Poly(L-arginine) Total Content by Reverse Phase Chromatography | Facilitate controlled release |
| Free Poly(L-arginine) and hGH Content in Supernatant by Reverse Phase Chromatography | Physical stability |
| Absorbance at 280 nm | Protein Concentration |
| Undissolved crystals/aggregates by Absorbance at 320 nm | Insoluble aggregates |
| Cation Exchange HPLC | Chemical degradation (deamidation) |
| Crystal Dissolution | hGH product release profile |

Chemical Degradation

Arrhenius-Plot kinetics can be employed to predict the rate of chemical degradation at 2-8° C. using short-term stability data, e.g., generated from samples that are stressed at higher storage temperatures such as 50° C., 40° C., 35° C., 30° C. and 25° C. Extrapolated 2-8° C. data can be used to establish a proposed shelf life or expiration date.

Arrhenius stability prediction can be used to test candidate formulations. The Arrhenius stress model is a common life stress relationship utilized in accelerated testing. It has been widely used when the stimulus or acceleration variable (such as deamidation, oxidation, etc) is thermal (i.e., temperature). It is derived from the Arrhenius reaction rate equation proposed by the Swedish physical chemist Svandte Arrhenius. The degradation rate at 5° C. can be predicted using stability results from several elevated temperatures. For example, samples of poly-Arg (pR) complexed crystals in prefilled syringes with Fluoroteck stoppers are placed at 2-8° C., 25° C., 30° C., 35° C., 40° C. and 50° C. Based on the reported data, the Arrhenius equation is applied and degradation rate at 5° C. is predicted. The results can be compared to the real stability of a known/standard lot that was analyzed by the same methods.

In addition, formulations can be tested by a dissolution profile assay, using a standard hGH formulation for comparison.

The following are examples of analytical methods that can be carried out to evaluate formulations containing crystalline hGH.

hGH Content

The hGH content of a suspension containing hGH crystals complexed with poly-Arg can be determined by UV spectrophotometry. The suspension of hGH crystals complexed with poly-Arg is dissolved in 50 mM glycine, pH 2.6 and absorbance at 280 nm is measured. The concentration of hGH is calculated by multiplying the measured absorbance value by the dilution factor, and then dividing by the absorption coefficient for rhGH, 0.75 mL·mg-1·cm-1.

Turbidity

The turbidity of the suspension of hGH crystals complexed with poly-Arg can be determined by UV spectrophotometry. The suspension of hGH crystals complexed with poly-Arg is dissolved in 50 mM glycine, pH 2.6 and absorbance at 320 nm is measured.

Particle Size Distribution

Particle size distribution can be evaluated to assess the consistency of the manufacturing process for a suspension containing hGH crystals complexed with poly-Arg. Particle size distribution can be determined by laser diffraction using a Coulter LS 230 Particle Size Analyzer (Coulter Corp., Miami, Fla.) with micro volume module. The sample is diluted in sample buffer or 1×PBS or the formulation vehicle to achieve an operation range of 8 to 12% obscuration. Each sample is analyzed in triplicate and data analysis is performed using the Fraunhofer optical model. The volume representing the cumulative distribution limits for 10% (dl10), 50% (median) and 90% (dl90) are reported. The test method can be performed for product stability testing as well (i.e., to assess the potential for particle distribution change upon storage).

RP-HPLC (Percentage of Oxidation, and Poly-L-Arginine Content)

Same mobile phases and column can be used for these analyses. The method for poly L arginine (poly-Arg) quantitation can be carried out at 214 nm and hGH at 280 nm. The amounts of poly L arginine, and hGH are used to calculate and report free hGH to supernatant and total poly-L-arginine content. The hGH/poly-Arg ratio (mass-to-mass) can be calculated using total hGH concentration derived from OD280 using an extinction coefficient of 0.75. Quantitation of poly-L-arginine can be determined by using a calibration curve of poly-L-arginine standards. The concentration of poly L-arginine in the test sample can be determined based on the linear regression line of poly-L-arginine standards. A C5 Supelco Discovery Bio Wide Pore column, 5 cm×4.6 mm, 3 µm particle size, 300 A pore size, can be used. hGH samples can be prepared for HPLC analysis by dissolution with a 50 mM glycine buffer, pH 2.6. The elution of rhGH is carried out at a flow rate of 1.0 mL/min with a mobile phase gradient formed by mobile phase A (water with 0.1% trifluoroacetic acid) and mobile phase B (acetonitrile with 0.1% trifluoroacetic acid) as follows: 0-2 min held at 95% A-5% B, 2-8 min linear change to 50% A-50% B, 8-20 min linear change to 30%

A-70% B, 20-22 min linear change to 10% A-90% B, 22-25 min held at 10% A-90% B, followed by return to the initial conditions of 95% A-5% B. The peak areas of oxidized rhGH are calculated and compared against that of non oxidized rhGH. Purity is calculated as the fractional peak area of the oxidized peak relative to the total area of all rhGH related peaks.

Soluble Aggregation (% High Molecular Weight)

High molecular weight soluble aggregates of rhGH can be separated from rhGH monomer by size exclusion HPLC. A Phenomenex BioSep-SEC-S 2000 7.8 mm I.D.×60 cm column can be used. hGH samples are prepared for HPLC analysis by dissolution with a 50 mM glycine buffer of pH 2.6. The elution of rhGH is carried out isocratically at a flow rate of 0.4 mL/min with a mobile phase consisting of 60 mM sodium phosphate, 3% isopropanol, pH 7.0. Detection of rhGH monomer and aggregates is carried out at 280 nm. The peak areas of aggregated rhGH are measured and compared against that of rhGH monomer peak. The peak before the main peak of rhGH is the aggregated species of rhGH. Percent aggregate is calculated as the fractional peak area of the aggregated peak relative to the total area of all rhGH protein peaks.

Deamidation and Other Degradations

Deamidated rhGH peaks can be separated from non-deamidated rhGH by Cation Exchange HPLC (CEX-HPLC). A PolyLC PolySULFOETHYL A, 4.6 mm×50 mm, 5 µm, 300 Å column can be used. hGH samples are prepared for HPLC analysis by dissolution with a 50 mM glycine buffer, pH 2.6. The elution of rhGH is carried out at a flow rate of 1.0 mL/min with a mobile phase gradient of increasing salt concentration formed by mobile phase A (50 mM sodium acetate, pH 4.6) and mobile phase B (50 mM sodium acetate, 250 mM sodium chloride, pH 4.6) as follows: Start at 100% A-0% B, 0 5 min linear change to 80% A-20% B, 5-40 min linear change to 40% A-60% B, 4-45 min linear change to 0% A-100% B, and return to initial conditions (100% A) in 5 min. Detection of deamidated and non-deamidated rhGH was carried out at 280 nm. The peaks before the main rhGH peak in the stressed sample are presumably deamidated and degraded rhGH species. The peak areas of deamidated rhGH are calculated and compared against that of non-deamidated rhGH. Purity is calculated as the fractional peak area of the degraded peak relative to the total area of all rhGH related protein peaks.

Dissolution Profile

A dissolution test for hGH crystals is developed to monitor the relevant parameters in effecting dissolution of poly L arginine-coated hGH crystals in a suitable buffer. Citrate, pH 5.0 can be used as the dissolution buffer. Dissolution rate of the complexed hGH is measured under the condition of fixed mg of hGH crystals in citrate pH 5.0 medium at constant agitation speed at 37° C. An initial dispersion is made followed by centrifugation to remove the supernatant, then replenished with new medium that is similar to physiological condition. The procedure is repeated every 15 minutes up to one hour, then the dissolution rate is calculated.

Dissolution rate may also be measured by UV absorbance or RP-HPLC (e.g., Agilent Technologies).

Bioactivity and pK Profile

The species used for in-vivo evaluation can be *Rattus norvegicus* (Wistar Rats, hypophysectomized). Treatment groups are designed to determine the comparability of crystalline hGH with a commercial hGH product at a matched weekly dose level. The diluted test articles are slowly injected subcutaneously in the thoraco-lumbar region on either side of the spine. The needle is directed away from the spine and inserted up to the hub before any material was injected. The site of injection is shaved and marked up to 3 days prior to dosing and thereafter as required to facilitate injection. All doses are administered using a 30-gauge×8 mm needle attached to a 300 µL syringe (BD part number BD 320438). Each single unit marking on the syringe is equivalent to 10 µL. Diluted Control and Test articles are carefully inverted in order to ensure suspension or solution uniformity without causing foaming prior to withdrawal into the syringe. The experiments provide a way to compare the bioactivity of hGH formulations when administered to hypophysectomized male Wistar rats. The selection of the control hGH formulation against which comparisons are made can be based, in part, on previously-established efficacy in a standard rat weight gain assay. Test or control material is administered to hypophysectomized male Wistar rats (9 rats/group) by subcutaneous (SC) injection. For example, growth of hypophysectomized rats after receiving a single SC injection of 5.6 mg/kg of a control formulation and a test formulation can be compared. As another example, daily SC injections of 0.8 mg/kg of a soluble commercial rhGH (e.g., Nutropin AQ) for 7 days (i.e. 5.6 mg/kg/week) can be used as a control. Body weights are measured weekly prior to the start of dosing and daily from Day −7 (seven days prior to dosing) until the end of the observation period on Day 8. In addition, blood can be withdrawn for blood level hGH determination for pK profile assay in a separate study. The blood hGH level can be determined by ELISA.

Pharmaceutical Formulations

The crystalline protein formulations described herein, e.g., poly-Arg complexed hGH crystals, can be formulated into pharmaceutical formulations for therapeutic use, e.g., to treat a subject suffering from an hGH insufficiency or deficiency.

Crystals of human growth hormone or a human growth hormone derivative can be combined with any pharmaceutically acceptable excipient. According to this disclosure, a "pharmaceutically acceptable excipient" is an excipient that acts as a filler or a combination of fillers used in pharmaceutical compositions. Preferred excipients included in this category are: 1) amino acids, such as glycine, arginine, aspartic acid, glutamic acid, lysine, asparagine, glutamine, proline; 2) carbohydrates, e.g., monosaccharides such as glucose, fructose, galactose, mannose, arabinose, xylose, ribose; 3) disaccharides, such as lactose, trehalose, maltose, sucrose; 4) polysaccharides, such as maltodextrins, dextrans, starch., glycogen; 5) alditols, such as mannitol, xylitol, lactitol, sorbitol; 6) glucuronic acid, galacturonic acid; 7) cyclodextrins, such as methyl cyclodextrin, hydroxypropyl-β-cyclodextrin and alike; 8) inorganic molecules, such as sodium chloride, potassium chloride, magnesium chloride, phosphates of sodium and potassium, boric acid, ammonium carbonate and ammonium phosphate; 9) organic molecules, such as acetates, citrate, ascorbate, lactate; 10) emulsifying or solubilizing/stabilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives, sorbitan derivatives; and 11) viscosity increasing reagents like agar, alginic acid and its salts, guar gum, pectin, polyvinyl alcohol, polyethylene oxide, cellulose and its derivatives propylene carbonate, polyethylene glycol, hexylene glycol, tyloxapol. Salts of such compounds may also be used. A further preferred group of excipients includes sucrose, trehalose, lactose, sorbitol, lactitol, mannitol, inositol, salts of sodium and potassium, such as acetate, phosphates, citrates and borate, glycine, arginine, polyethylene oxide, polyvinyl alcohol, polyethylene glycol, hexylene glycol, methoxy polyethylene glycol, gelatin, hydroxypropyl-β-cyclodextrin, polylysine and polyarginine.

In some embodiments of this disclosure, the excipient is selected from the group consisting of: amino acids, salts, alcohols, carbohydrates, proteins, lipids, surfactants, polymers, polyamino acids and mixtures thereof. In some preferred embodiments, the excipient is selected from the group consisting of: protamine, polyvinylalcohol, cyclodextrins, dextrans, calcium gluconate, polyamino acids, such as polyarginine, polylysine and polyglutamate, polyethylene glycol, dendrimers, polyorthinine, polyethyleneimine, chitosan and mixtures thereof. In more preferred embodiments, the excipient is selected from the group consisting of: protamine, polyarginine, polyethylene glycol and mixtures thereof.

Crystals of human growth hormone or a human growth hormone derivative according to this disclosure can also be combined with a carrier or excipient, a substance that, when added to a therapeutic, speeds or improves its action (see, e.g., The On-Line Medical Dictionary at http://cancerweb.ncl.ac.uk/omd/index.html). Examples of carriers or excipients include, for example, buffer substances, such as phosphates, glycine, sorbic acid, potassium sorbate, partial glyceride mixtures of saturated vegetable fatty acids, waters, salts or electrolytes, such as protamine sulfate, disodium hydrogen phosphate, sodium chloride, zinc slats, colloidal silica, magnesium, trisilicate, cellulose-based substances and polyethylene glycol. Carriers or excipients for gel base forms may include, for example, sodium carboxymethylcellulose, polyacrylates, polyoxyethylene-polyoxypropylene-block copolymers, polyethylene glycol and wood wax alcohols.

In yet other preferred embodiments, the excipient is protamine. Furthermore, crystals of hGH or an hGH derivative and protamine are present in an hGH:protamine ratio of about 5:1 to about 1:10 (w/w). That ratio may also range between about 10:1 to about 20:1 (w/w). Most preferably, that ratio ranges between about 12:1 to about 15:1 (w/w). According to alternate embodiments, that ratio is between about 3:1 and about 1:10 (w/w). In other embodiments, that ratio is between about 5:1 and about 40:1 (w/w). And, in a further embodiment, that ratio is about 5:1 (w/w).

In another aspect, the pharmaceutically acceptable excipient is selected from the group consisting of polyamino acids, including polylysine, polyarginine and polyglutamate. In preferred embodiments, the excipient is polylysine. In a more preferred embodiment, polylysine has a molecular weight between about 1,500 and about 8,000 kD. In other embodiments, the crystals of hGH or an hGH derivative and polylysine are present in an hGH:polylysine ratio of about 5:1 to about 40:1 (w/w). That ratio may also range between about 10:1 to about 20:1 (w/w). Most preferably, that ratio ranges between about 12:1 to about 15:1 (w/w). According to alternate embodiments, that ratio is about 5:1 to about 1:50 (w/w). In further embodiments, that ratio is about 5:1 (w/w).

In yet other preferred embodiments, the excipient is polyarginine. In more preferred embodiments, polyarginine has a molecular weight between about 15,000 and about 60,000 kD. In other embodiments, the crystals of hGH or an hGH derivative and polyarginine are present in an hGH: polyarginine ratio of about 5:1 to about 40:1 (w/w). That ratio may also range between about 10:1 to about 20:1 (w/w). Most preferably, that ratio ranges between about 12:1 to about 3:1 (w/w). According to alternate embodiments, that ratio is about 5:1 to about 1:50 (w/w). In other embodiments, that ratio is between about 12:1 and about 15:1 (w/w). In further embodiments, that ratio is about 5:1 (w/w).

Other embodiments of the disclosure include an injectable crystalline suspension comprising about 20 mg/ml of crystals of hGH or an hGH derivative. The suspension is characterized by easy resuspendability, slow sedimentation, and a time action profile of about 7 days. It may be injected once weekly, using a 30 gauge syringe and providing an 80% level of effective loading. The suspension is substantially pure, as reflected by parameters of 0.02% aggregation (SE-HPLC) and 2.3% related proteins (RP-HPLC). This purity is maintained for at least about 4 months under refrigerated conditions.

Other embodiments of the disclosure relate to a crystal of hGH or an hGH derivative which is characterized as having delayed dissolution behavior when introduced into an individual, as compared to that of conventional soluble hGH or hGH formulations. According to this disclosure, dissolution of crystals of hGH or an hGH derivative is characterized by either in vitro or in vivo dissolution parameters. For example, in vitro dissolution is described as the concentration of soluble hGH (expressed as a percentage of total or mg of total hGH or hGH derivative crystals originally present) obtained per 15 minutes or per wash step in a sequential dissolution process. In other embodiments, crystals of hGH or an hGH derivative are characterized by an in vitro dissolution rate of between about 2 and about 16% of said crystal per wash step upon exposure to a dissolution buffer (50 mM HEPES (pH 7.2), 140 mM NaCl, 10 mM KCl and 0.02% (v/v) $NaN_3$) at a temperature of 37° C., wherein the concentration of hGH or an hGH derivative is present in solution at a concentration of about 2 mg/ml. In another embodiment, crystals of hGH or an hGH derivative are characterized by an in vitro dissolution rate of between about 0.04 to about 0.32 mg of said crystal per wash step in a sequential dissolution process. On the other hand, in vivo dissolution is described by serum levels of hGH in a mammal over time after a single injection of hGH into the mammal.

Therapeutic Use and Dosage

In mammals, GH stimulates tissues to synthesize and secrete IGF-1, a protein that, in turn, plays a role in cell division and metabolic processes. As will be appreciated by those of skill in the art, serum hGH and IGF-1 levels are dependent on many factors, including physiological and treatment-related factors. Such factors include, but are not limited to: physiological factors, such as: birth age and bone age, sex, body weight, developmental stage (e.g., increased level at puberty) and treatment-related factors, such as dose, rate (kinetics) of dosing and route of administration, and patient diagnosis and medical history. Also, those of skill in the art will appreciate that different hGH and IGF-1 levels may be beneficial, both from the standpoint of safety and efficacy, for different patient populations.

Adults or children suffering from a variety of hGH insufficiencies, disease states or syndromes may be treated by various regimens of exogenously delivered hGH using hGH crystals or hGH derivative crystals according to this disclosure. For example, an endocrinologist may initiate therapy using a dose of about 0.2 mg/kg/week for a child, increasing the dose to about 0.3 mg/kg/week after several weeks or months of treatment, with the dose being further increased to about 0.7 mg/kg/week around puberty. As will be appreciated by those of skill in the art, the level of such exogenously delivered hGH dosed to adults or children requiring hGH delivery is also dependent upon the existing physiological level or concentrations of hGH.

Dosage regimens for hGH in adults or children are often expressed in terms of mg/kg or International Units (IU/kg). Such regimens are generally scheduled for either a day or a week, i.e., mg/kg/day or mg/kg/week. With such considerations in mind, according to one embodiment of this disclosure, a single administration of crystals of hGH or an hGH derivative, or a composition comprising such crystals, for example, a single weekly administration of about 9 mg per 30 kg child, provides an in vivo hGH serum concentration of greater than about 10 ng/ml on days 1 and 2 post-administration, greater than about 5 ng/ml on days 3 and 4 post-administration and about 0.3 ng/ml on day 5 to day 7 post-administration. Alternatively, a single administration of crystals of hGH or an hGH derivative, or a composition comprising such crystals, provides an in vivo hGH serum concentration of about 0.3 ng/ml to about 2,500 ng/ml hGH, preferably about 0.5 ng/ml to about 1,000 ng/ml hGH, most preferably about 1 ng/ml to about 100 ng/ml hGH for between about 0.5 hours and about 40 days post-administration in said mammal, preferably for between about 0.5 hours and any one of about 10 days, 7 days or 1 day post-administration. Similarly, a single administration of crystals of hGH or an hGH derivative, or a composition comprising such crystals, provides an in vivo serum concentration of above about 2 ng/ml hGH, preferably above about 5 ng/ml hGH, most preferably above about 10 ng/ml hGH for between about 0.5 hours to about 40 days post-administration in said mammal, preferably for any one of about 10, 7 or 1 days post-administration. In a more preferred embodiment of this disclosure, a single administration of crystals of hGH or an hGH derivative, or a composition comprising such crystals, provides an in vivo serum concentration of greater than about 0.3 ng/ml hGH for between about 0.5 hours and about 40 days in a mammal, preferably for any one period of any one of about 10, 7 or 1 days post-administration. According to one embodiment of this disclosure, a single weekly administration of crystals of hGH or an hGH derivative, or a composition comprising such crystals, provides an in vivo hGH serum concentration of greater than about 10 ng/ml hGH on days 1 and 2 post-administration, greater than about 5 ng/ml hGH on days 3 and 4 post-administration and above about 0.3 ng/ml hGH on day 5 to day 7 post-administration. In a further embodiment, a single administration of crystals of hGH or an hGH derivative, or a composition comprising such crystals, provides an in vivo serum concentration of greater than about 0.3 ng/ml hGH for between about 0.5 hours and about 10 days post-administration.

According to other embodiments of this disclosure, a single administration of crystals of hGH or an hGH derivative, or a composition comprising such crystals, provides an in vivo IGF-1 serum elevation over baseline IGF-1 level prior to said administration of greater than 50 ng/ml from about 10 hours to about 72 hours post-administration and between about 0.5 ng/ml to about 50 ng/ml from about 72 hours to about 15 days post-administration, preferably about 10 days post-administration. Alternatively, a single administration of crystals of hGH or an hGH derivative, or a composition comprising such crystals, provides an in vivo IGF-1 serum elevation of about 5 ng/ml to about 2,500 ng/ml, preferably about 100 ng/ml to about 1,000 ng/ml, for about 0.5 hours to about 40 days post-administration, preferably about 7 days post-administration. Alternatively, a single administration of crystals of hGH or an hGH derivative, or a composition comprising such crystals, according to the present disclosure may provide an in vivo IGF-1 serum elevation of above about 50 ng/ml, preferably above about 100 ng/ml, for about 0.5 hours to about 40 days post-administration, preferably about 7 days post-administration. According to one embodiment of this disclosure, a single administration of crystals of hGH or an hGH derivative, or a composition comprising such crystals, provides an in vivo IGF-1 serum elevation over baseline IGF-1 level prior to said administration of greater than about 50 ng/ml from about 10 hours to about 72 hours post-administration and between about 0.5 ng/ml to about 50 ng/ml from about 72 hours to about 15 days post-administration or 72 hours to about 10 days post-administration.

According to this disclosure, a single administration is defined as between about 0.01 mg/kg/week to about 100 mg/kg/week hGH crystals or hGH derivative crystals, or a composition comprising such crystals, wherein the volume of the administration is between 0.1 ml and about 1.5 ml. For example, pediatric growth hormone deficiency may be dosed with hGH crystals or hGH derivative crystals, or a composition comprising such crystals, at about 0.3 mg/kg/week, e.g., about 9 mg for a 30 kg child. Turner syndrome may be dosed with hGH crystals or hGH derivative crystals, or a composition comprising such crystals, at about 0.375 mg/kg/week, e.g., about 11.25 mg for a 30 kg child. Additionally, adult growth hormone deficiency may be dosed with hGH at about 0.2 mg/kg/week, e.g., about 16 mg for a 80 kg adult. AIDS wasting disease may be dosed with hGH at 6 mg/day, e.g., 42 mg/week.

In yet other embodiments, crystals of hGH or an hGH derivative, or composition comprising such crystals, display a relative bioavailability similar to that of soluble hGH in a mammal. The crystals according to this disclosure have a relative bioavailability of at least 50% or greater compared to that of soluble hGH, delivered by the same route (e.g., subcutaneous or intramuscular injection), wherein said bioavailability is measured by the area under curve (AUC) of total in vivo hGH serum concentration for said soluble hGH and said crystal. Crystals of hGH or an hGH derivative are thus characterized by an advantageous in vivo dissolution rate.

The present disclosure further provides methods of administering crystals of hGH or an hGH derivative to a mammal having a disorder associated with human growth hormone deficiency or insufficiency or which is ameliorated by treatment with hGH. The method comprises the step of administering to the mammal a therapeutically effective amount of a crystal of hGH or an hGH derivative. Alternatively, the method comprises the step of administering to the mammal an effective amount of a composition comprising crystals of hGH or an hGH derivative alone or with an excipient. Various embodiments of crystals of hGH or an hGH derivative according to this disclosure are: calcium crystals, monovalent crystals, protamine crystals or polyarginine crystals of hGH or an hGH derivative. Such crystals, or compositions comprising them, may be administered by a time regimen of about once every three days, about once a week, about once every two weeks or about once every month.

Disorders related to hGH insufficiency or deficiency that may be treated according to this disclosure include, but are not limited to: adult growth hormone deficiency, pediatric growth hormone deficiency, Prader-Willi syndrome, Turner syndrome, short bowel syndrome, chronic renal insufficiency, idiopathic short stature, dwarfism, hypopituitary dwarfism, bone regeneration, female infertility, intrauterine growth retardation, AIDS-related cachexia, Crohn's disease, burns, as well as other genetic and metabolic disorders. In one embodiment of this disclosure, the disorder is pediatric growth hormone deficiency and treatment results in annualized growth velocity of between about 7 cm and about 11 cm in the child undergoing treatment.

In another embodiment, a calcium crystal of hGH or an hGH derivative may serve as a useful adjunct for bone therapy, as well as treatment of human growth hormone deficiency in a mammal.

The present disclosure also provides methods for inducing weight gain in a mammal, comprising the step of administering to said mammal a therapeutically effective amount of crystals of hGH or an hGH derivative. Alternatively, such methods comprise the step of administering to said mammal a therapeutically effective amount of a composition comprising crystals of hGH or an hGH derivative and an excipient. In one embodiment of such methods, the weight gain induced in a hypophysectomized rat is between about 5% and about 40% after administration of said crystals by injection once a week.

Crystals of hGH, crystals of an hGH derivative or compositions comprising them alone, or with an excipient, may be administered alone, or as part of a pharmaceutical, therapeutic or prophylactic preparation. They may be administered by any conventional administration route including, for example, parenteral, oral, pulmonary, nasal, aural, anal, dermal, ocular, intravenous, intramuscular, intraarterial, intraperitoneal, mucosal, sublingual, subcutaneous, transdermal, topical, buccal or intracranial routes.

In some embodiments, crystals of hGH or an hGH derivative, or compositions (e.g., formulations containing crystalline hGH suspensions) comprising them, with or without an excipient, are administered by oral route or parenteral route. In preferred embodiments, crystals of hGH or an hGH derivative, or compositions comprising them, with or without an excipient, are administered by subcutaneous or intramuscular route.

In preferred embodiments, the crystals or compositions of this disclosure, are administered by subcutaneous route, using a needle having a gauge greater than or equal to 27. In one embodiment of this disclosure, the needle gauge may be equal to 30. The crystals or compositions may be administered from a pre-filled syringe or a meta dose infusion pump. Alternatively, they may be administered by needle-free injection.

This disclosure advantageously permits sustained release of hGH into a mammal. In one embodiment, the crystals or compositions according to this disclosure are administered about once a week. In another embodiment, the crystals or compositions according to this disclosure are administered about once every two weeks. In yet another embodiment, the crystals or compositions according to this disclosure are administered about once every month. It will be appreciated by those of skill in the art that the specific treatment regimen will depend upon factors such as the disease to be treated, the age and weight of the patient to be treated, general physical condition of the patient and judgment of the treating physician.

Kits

Kits containing a formulation containing poly-Arg complexed crystalline hGH and instructions for use, and optionally, a device for administering the formulation are also part of the present disclosure. The formulation can be in a suitable container (e.g., vial, prefilled syringe, etc). The instructions can take any form, e.g., a pamphlet or sheet, or a world wide web address to a site where instructions are provided. The instructions can include, e.g., instructions for storage and/or administration.

Overview: Needle-less Injection Systems for Crystalline Protein Formulations

This disclosure further relates to the field of crystalline suspensions of therapeutic proteins for use with needle-free (jet) injectors for administration to subjects. The disclosure also features methods of preparing formulations of crystalline proteins that are suitable for needleless injection.

Needless injection devices help to increase subject compliance by improving ease of drug administration; decreasing injection time, and possibly reducing pain upon injection. In some aspects, crystalline protein formulations have advantages over soluble formulations. Crystallization can extend the release time of a protein, thereby decreasing the frequency of administration, and possibly increasing subject compliance. As one example, a crystalline insulin formulation is available. By using crystallization technology, it was possible to extend release time of insulin, thereby decreasing the frequency of drug administration and increasing subject compliance.

Needle-free options may also help to an increase subject compliance with crystalline drugs, as needle phobia has been reported in about 5-10% of the patient population. Further, it would be beneficial for subjects to have multiple delivery options for administration of crystalline formulations (e.g., parenteral formulations), including a needle-free option.

Another example of an application for needle-free injectors in conjunction with crystalline protein formulation is the veterinary market. It is possible to use crystalline formulation providing extended drug release in combination with jet injectors to improve animal care compliance. Compliance can be increased in part because of decreased frequency of administrations, shorter time required for injection, and decreased pain upon injection.

A needle-free jet injector is a type of medical injecting syringe that uses a high-pressure narrow jet of the injection liquid instead of a hypodermic needle to penetrate the epidermis. It is powered by compressed air or gas, either by a pressure hose from a big cylinder, or from a built-in gas cartridge or small cylinder. Some are multi-shot, and some are one-shot.

Needle-free injection systems are known. Examples include: BioJector 2000, VetJet, Vitajet, JET2000, MIT-V jet injector, LectraJet, Akra Dermojet, and Med-E-Jet injector.

A jet injector, e.g., BioJector needle-free (jet) injection system, can be used to study the feasibility of using jet injectors with crystalline protein formulations. BioJector's needle-free injection technology works by forcing liquid medication at high speed through a tiny orifice held against the skin. This creates a fine stream of high-pressure medication that penetrates the skin, depositing the medication in the tissue beneath.

BioJector 2000: The BioJector 2000 consists of two components: a hand-held, reusable jet injector and a sterile, single-use, disposable plastic syringe. The BioJector 2000 uses disposable carbon dioxide cartridges as a power source. The carbon dioxide gas provides consistent, reliable pressure on the plunger of the disposable syringe, thereby propelling the medication into the tissue. The second component of the system, the BioJector single-use disposable syringe, consists of a plastic, needle-free, variable dose syringe. The body of the syringe is transparent and has graduated markings to aid accurate filling. There are five different BioJector syringes, each of which is intended for a different injection depth or body type.

VetJet and Vitajet: The VetJet is a modified Vitajet for use in the veterinary market. VetJet is also composed of two components, a portable injector unit and a disposable syringe. VetJet is powered by a spring.

Needle-free injectors have been in use for administration of liquid non-crystalline protein formulations. A possible reason for absence of reported case of needle-free device for suspensions crystalline protein is that protein crystals represent particulates in suspension which could make injection via needle-free device difficult or which could cause physical changes to crystalline formulation, thereby undermining therapeutic action of the formulation.

Vaccines are examples of suspensions of antigens formulated with an adjuvant (e.g., aluminum hydroxide). Needle-free jet injectors have been used to administer vaccines. In contrast, crystalline protein formulations have different mode of actions, different purpose, different requirements for integrity of formulations, and different suspension properties as compared to vaccine formulations.

The standard approach of administration of soluble and crystalline therapeutic parenteral formulations is with hypodermic needs. Pain upon injection is associated with the size of the needle and the amount of time that the needle is held at the injection site of the subject. Larger needle gauge and increased time of injection are both associated with increased pain at the injection site caused by the needle. Because jet injectors have comparatively small orifice size (Table 2) and injection time is very short, pain upon injection is significantly less compared to the needle injection systems.

However, the use of needle free (jet) injectors for therapeutic suspensions (e.g., suspensions of crystalline protein) requires additional considerations. As described herein, the use of needle-free injectors for delivery of crystalline protein suspension formulations was evaluated. Becton Dickinson needles of 30 to 18 gauges were used for comparison in the study. Needle G30 was regular wall and G25, 21 and 18 needles were thin-wall. Comparison of needle inner and outer diameters represent in Table 2.

TABLE 2

Orifice sizes of jet injection systems and inner diameters of needles used in the study

| Injection system | Orifice or Needle I.D., μm | Needle O.D., μm |
| --- | --- | --- |
| BioJector 2000 system with Size 2 syringe 1S021 | 114 | 114*, [1] |
| VetJet system with 0.0062" nozzle syringe Ref # K7000 | 157 | 157*, [2] |
| 30G needle | 160 | 310 |
| 25G needle | 310 | 510 |
| 21G needle | 590 | 820 |
| 18G needle | 980 | 1270 |

*O.D. for jet injectors equals I.D of jet injector orifice;
[1] Equivalent needle gauge is 36
[2] Equivalent needle gauge is 34

The capability of crystalline suspension to be administered using needle-free jet injectors was assessed. Limitations on crystalline suspensions that could be used in needle-free injectors exist. Surprisingly, it was determined that formulations containing crystalline suspensions that are appropriately formulated and selected can be administered using needle-free (jet) injection systems.

Advantages of the disclosure include:
use of needle-free (jet) injection devices for administration of crystalline protein suspensions formulations;
retaining therapeutic action of said crystalline formulations; and
reduced pain upon injection when using needle-free (jet) injectors.

As demonstrated herein, factors that affect the ability to use needless injectors include:
the sedimentation rate of the crystalline protein and
the size of the particles (i.e., crystals).

For example, if the sedimentation rate of the crystalline protein is high, after injection, a portion of the protein may remain in the injector and not be delivered to the subject. As a result, the subject may not receive the required dosage of the protein. If the largest dimension of the crystals is too large, e.g., larger than the orifice, or in some cases more than ⅓ the diameter of the orifice, the crystals may clog the orifice, the crystals may not successfully load into the injection module, and/or the crystals may be damaged by the interaction with the orifice border (e.g., altering crystal morphology or size).

Needle-free injection can be used to administer any formulation containing a crystalline protein suspension, if certain conditions are satisfied. For example, if a crystalline protein suspension has a low sedimentation rate, e.g., the majority of the protein is delivered to the subject and does not remain in the injector (e.g., even after a delay between preparing the syringe and administering to a subject and/or independent of the position in which the injector is held (e.g., upside down, horizontal)), it may be suitable for needless administration.

Likewise, if the particle size of the crystals is smaller than the orifice, and ideally, if the particle size (e.g., the largest dimension of the particle) is about or less than ⅓ the diameter of the orifice, the crystalline protein may be suitable for needless administration.

If a formulation of crystalline protein does not appear to be well-suited for needless injection, e.g., based on an evaluation of the sedimentation rate and/or particle size of the crystals, or based on an attempt (e.g., unsuccessful attempt) to use needless injection to administer the crystalline protein, the properties of the formulation can be optimized (e.g., to decrease the crystal size or decrease the sedimentation rate, without decreasing the efficacy of the protein by an unacceptable amount), e.g., by varying the pH, buffer, salt concentration, suspending agent, preservative, etc., to make the formulation suitable for use with a needless injection system.

Particle Size

The particle size of crystalline protein can be measured, e.g., by laser diffraction (e.g., using a Coulter LS 230 Particle Size Analyzer (Coulter Corp., Miami, Fla.) with micro volume module). If the particle size (e.g., the largest dimension) is less than the size or the orifice, e.g., less than about ½, particularly if the size is less than about ⅓ the diameter of the orifice, the formulation may be suited for needless injection.

Suitability of a crystalline protein with a given particle size for needless injection can be tested, e.g., by injecting a crystalline protein formulation with a needle-free injector (e.g., BioJector 2000) and observing particle size after first and repeated injections and comparing the particle sizes post-injection to the particle size prior to injection. Particle size can be measured using a Coulter LS 230 particle sizer prior to injection, and after first and repeated injections. Fraunhofer optical model can be used to analyze data. The particle size can be verified with microscopic observation. Microscopic observation can also be used to detect possible changes in crystal morphology. If minimal or no changes in particle size are observed and the majority of the dose is delivered from the injector, the crystalline protein may be suitable for needless injection.

If a crystalline protein does not perform well in this analysis, i.e., the particle size is larger than the orifice, the formulation vehicle can be optimized, or the crystals themselves (e.g., the crystals may be complexed with an agent (e.g., polycation or polyamino acid e.g., poly-Arg), or the ratio of the complexing agent to protein may be varied) to affect the crystal size may be optimized.

Sedimentation Rate

The sedimentation rate can affect the suitability of a crystalline protein for needless injection. If the sedimentation rate is high, the dose delivered to a subject may be inconsistent. High crystalline suspension sedimentation rate may be defined as a rate that allows for dose redistribution in a needle-free device during the time required for dose preparation and administration, e.g., about 90% redistribution after an hour incubation of the device in a horizontal position. Low sedimentation rate may be defined as a rate that allows for a preparation and administration of dose without substantial dose redistribution. In one embodiment, a high sedimentation rate may be defined as the rate allowing for less than 90% dose injection upon incubation of needle-free device in horizontal position. In some embodiments, low sedimentation rate may be defined as rate allowing for uniform dose (e.g., minimal or no dose re-distribution; e.g., less than about 35%, about 30%, about 25%, about 20%, about 15%, about 10%, about 9%, about 8%, about 7%, about 6%, about 5%, about 4%, about 3%, about 2%, about 1%,) after more than one hour incubation in any position.

For example, the sedimentation rate can be measured indirectly. As one example, a suspension is held for three minutes in a horizontal, vertical upright or upside down position. If substantial (e.g., about 80%) dose redistribution is observed or measured, e.g., after 10 or 20 minutes incubation time, the sedimentation rate is viewed as high. As another example, a suspension incubated for one hour in various positions with no dose redistribution is viewed as having a low sedimentation rate.

Suitability of a crystalline protein for needless injection based on its sedimentation rate can be evaluated, e.g., by loading a suspension into a BioJector syringe and injecting the suspension either immediately after loading or injecting after a hold period of one hour in horizontal, vertical upright, and upside down positions. The hold samples are compared with the sample injected immediately after loading into the jet injector's syringe. The after-injection content of the protein that was injected and the amount remaining inside the syringe are determined and expressed as percentages, considering as 100% the material that was loaded into syringe. If there are no or minor differences observed in dose distribution between the immediately-injected sample and the injected samples that had been held prior to injection, the crystalline protein may be suitable for needless injection.

If a crystalline protein does not perform well in this analysis, i.e., the delivered dose decreased greatly for the samples held prior to injection, the formulation vehicle can be optimized, or the crystals themselves (e.g., the crystals may be complexed with an agent (e.g., polycation or poly amino acid, e.g., poly-Arg), or the ratio of the complexing agent to protein may be varied) to affect the crystal size, or the concentration of the protein may be optimized.

Methods of Use

Needless injection systems can be used to administer a formulation containing a crystalline protein to a subject. For example, the subject can be a patient in need of treatment with the crystalline protein, e.g., the crystalline protein can be crystalline hGH and the patient may suffer from an hGH deficiency. The dose and dose schedule for administration are determined based on a variety of factors. Such factors include, but are not limited to, physiological factors, such as birth age and bone age, sex, body weight, developmental stage (e.g., increased level at puberty) and treatment-related factors, such as dose, rate (kinetics) of dosing and route of administration, and patient diagnosis and medical history.

Kits

Kits containing a formulation containing a crystalline protein and instructions for use in needless injection, and optionally, a device for needless injection are also part of the present disclosure. The formulation can be in a suitable container (e.g., vial, prefilled syringe, etc). The instructions can take any form, e.g., a pamphlet or sheet, or a world wide web address to a site where instructions are provided. The instructions can include, e.g., instructions for storage and/or administration.

Analytical Methods

Analytical methods that can be utilized in assessing the suitability of crystalline proteins for needless injection include the following.

Injection

Crystalline formulations are injected with the use BioJector 2000 system with 1S021 syringe and VetJet system with 0.0062" nozzle syringe Ref # K7000, BD 0.5 cc syringe with preattached 30 G×½" needle (BD Part # 328466), through 30 G×½" (BD Part #305106), 25 G×⅝" (BD Part #305122), 18 G×½" (BD Part #305196) attached with luer-lock to 1 mL syringe (BD Part # 309628). 0.25 mL Samples are tested in duplicates. BioJector 2000 and VetJet systems are used according to BioJector's recommendations.

SE-HPLC

To determine purity using the SE-HPLC (size-exclusion HPLC) method, a Phenomenex BioSep SEC-S-2000 column is used. Ten microliters of 2 mg/mL concentration sample is injected into the column. The running buffer is composed of 3% IPA and 60 mM sodium phosphate, pH 7.0. The flow rate is set to 0.6 mL/min and the run time is 30 minutes. Detection is performed at 214 nm. The resulting chromatogram is manually integrated. Percent purity (monomer) was calculated based on peak area.

RP-HPLC

RP-HPLC is used for purity testing. To determine the purity of a protein using the RP-HPLC method, a C5 Supelco Discovery Bio Wide Pore Column, 5 cm×4.6 mm, 3 μm particle size, 30 nm Pore size is used. The column thermostat temperature is set to 37° C. Ten microliters of sample at 2 mg/mL concentration is injected. The elution is carried out at a flow rate of 1.0 mL/min with a gradient system present by mobile phase A (0.1% TFA in water) and mobile phase B (0.8% TFA in MeCN). The gradient system is changed from 5% B to 50% B from 0-2.5 min., then 50% to 70% B in 2.5-15.5 min. then, 70% to 90% in 15.5 to 17 min., immediately following this 5% B is re-established. A 3 min post-time is held before the start of the next run. Detection is performed at 214 nm. The resulting chromatogram is manually integrated. Percent purity is calculated based on peak area.

SCX-HPLC (Strong Cation Exchange) Chromatography

The SCX-HPLC method is used to measure deamidation specific in stability testing. To determine the purity of protein using the IEX-HPLC method, a PolyLC (NEST Group cat #P054SE0503) column was used. The column thermostat temperature was set to 30° C. Twenty microliters of sample at 2 mg/mL concentration injected. The elution is carried out at a flow rate of 1 mL/min with a gradient system present by mobile phase A (50 mM Na Acetate, pH 4.6) and mobile phase B (50 mM Na Acetate, pH 4.6 250 mM NaCl). The gradient system is changed from 0% B to 20% B from 0 to 5 min., then 20% to 70% B in 5 to 25 min. then, 70% to 100% in 25 to 25.1 min. 100% B is kept until 27 min. following 27.1 min, 0% B is re-established for a 5 min. post-time. Detection is performed at 214 nm and 280 nm. The resulting chromatogram was manually integrated. Percent purity was calculated based on peak area.

Particle Size Distribution (PSD)

PSD is determined by laser diffraction using a Coulter LS 230 Particle Size Analyzer (Coulter Corp., Miami, Fla.) with micro volume module. The sample is diluted in sample buffer to achieve an operation range of 8% to 12% obscuration. Data analysis is performed using the Fraunhofer optical model. Size in μm of particle fraction representing cumulative volume distribution limits of 10% (dl10), 50% (median) and 90% (dl90) is reported.

3-pH Dissolution Test

This test is used to assess changes in dissolution profiles in protein samples.

Particle Surface Charge

Particle Surface Charge is determined using Zetasizer Nano-Z (Malvern Instruments Ltd. UK). Running buffer was 20 mM Tris, pH 7.5. Zeta Potential Transfer Standard is used to calibrate the instrument (Malvern catalog #DTS1050). For each sample, 12 µl crystalline aliquot (concentration between 10 to 30 mg/ml) is added to 588 µl running buffer, and three measurements are taken at room temperature.

Microscopic Appearance

The microscopic appearance of the crystalline test article is assessed to detect any relevant changes in the test article due to injections.

EXAMPLES

Example 1

A crystallization and complexation process for hGH to produce long-acting hGH with a controlled release profile has been developed (US pub. app. no. 2004/0209804). The poly-Arg complexation is critical in contribution of the controlled release profile because the bare hGH crystals perform the same as the daily injection product in the market. Poly-Arg complexed hGH crystals or hGH derivative, or compositions or formulations comprising them, have several advantages including: the capability of once per week delivery, ready to use crystalline suspension form, safety, efficacy, purity, stability and syringeability over a period of time. The complexed hGH drug delivery method is designed for fewer injections without the use of polymers or fusion proteins and to offer a more user-friendly treatment alternative for subjects. The uniqueness of this crystallization technology is that no increase of soluble aggregates is observed because limited free hGH is present in the supernatant.

Formulation development studies were conducted to evaluate the effect of pH and buffer species. Based on the results, excipients and ionic strength were then screened. Acceptable formulation development was assessed by the following characteristics: storage stability at various temperatures, container-closure compatibility as a function of dose consistency, potential stickiness, ease of administration of product, and loss to container closure. The stability test methods and their application are listed in Table 1.

Several factors such as hGH to pR ratio, particle size distribution, were critical in the release profile upon injection. Changes in these factors during stability of ALTU-238 were studied. In addition, dissolution profile assays were used to assess the controlled release profiles, as the improved formulations need to demonstrate comparable release profiles as the earlier formulation.

Both glass vials and prefilled syringes were evaluated during the development phase as potential container closure configurations for the finished drug product. Additional development studies evaluated siliconized vs. non-glass vials and/or syringes.

A fixed protein fill concentration covering a delivered volume ranging from 0.2 mL to 1.0 mL was evaluated.

Arrhenius-Plot kinetics were employed to predict the rate of chemical degradation at 2-8° C. using short-term stability data generated from samples that were stressed at higher storage temperatures such as 50° C., 40° C., 35° C., 30° C. and 25° C. Extrapolated 2-8° C. data was used to establish the proposed shelf life or expiration date.

In addition, selected formulations were tested with rat hypox model to evaluate the controlled release profile, using the clinical trial formulation for comparison.

As described herein, preferred liquid suspension protein formulations of complexed hGH are prepared using a buffer (preferably phosphate) at the pH range from 6 to 7, a salt (preferably sodium chloride or sodium acetate), and a suspending agent (preferable polyethylene glycol 6000 or 8000). The container closure systems that are compatible with these formulations are siliconized prefilled syringes with a head space less than 10 mm or vials with no head space.

The results indicate that chemical degradation and crystal form changes are considerations for ALTU-238 stability, the extent of which is affected by the buffer species, ionic strength and pH. pH is a major factor affecting the stability of hGH complexed crystals for chemical degradation, increasing pH>7.0 increases deamidation. As demonstrated, pH has a significant effect on deamidation (FIG. 1). Preferably, the pH should be in the range from pH 6.1 to 7.2, more preferably in the range of pH 6.1 to 6.8.

Table 3 shows $OD_{320}$ data of the dissolved crystals in glycine buffer and indicates that insoluble aggregates were formed. The histidine pH 5.0 and 5.5 samples were very turbid after the addition of dissolution buffer. This turbidity could be filtered out by a 0.45 µm filer indicating insoluble aggregates were formed. Additionally, histidine containing samples at pH 6.0, 6.5 and 7.0 also had higher $OD_{320}$ compared to other phosphate buffers at the same pHs. It implies the presence of insoluble aggregates or changes of the crystal form resulting in non-dissolvable complexed crystals in glycine buffer. These results also indicate phosphate is a preferable buffer compared to histidine at the same pH ranges. Histidine is not preferred for higher level of light scattering due to undissolved crystals or insoluble aggregates.

TABLE 3

Summary of turbidity by $OD_{320}$ of the dissolved crystals in glycine, pH 2.6 buffer for the stability samples

| Formula | Time 0 | 1 week at 40° C. |
|---|---|---|
| Phosphate, pH 6.5 | 0.014 | 0.016 |
| Phosphate, pH 7.0 | 0.008 | 0.014 |
| Phosphate, pH 7.5 | 0.011 | 0.016 |
| Histidine, pH 5.0 | 0.009 | 4.204 |
| Histidine, pH 5.5 | 0.010 | 0.278 |
| Histidine, pH 6.0 | 0.010 | 0.063 |
| Histidine, pH 6.5 | 0.009 | 0.053 |
| Histidine, pH 7.0 | 0.005 | 0.046 |
| Control ALTU-28 standard | 0.034 | 0.020 |

The crystal sizes of these histidine and citrate containing samples were smaller than the others that suggest that the crystals were dissolving. Higher solubility is observed in citrate buffers (Table 4). The solubility of hGH complexed crystals is less than 0.1 mg/mL in phosphate buffer.

TABLE 4

Solubility in citrate buffer at various pH. The hGH complexed crystals have higher solubility in citrate buffer

| pH | Solubility in citrate buffer mg/mL hGH |
|---|---|
| 7 | 0.9 |
| 6 | 1.7 |
| 5.5 | 1.6 |

Therefore, histidine and citrate are not preferred buffers. The solubility of hGH complexed crystals in phosphate buffer at various pH was less than 0.1 mg/mL. The preferred formulation uses a phosphate salt buffer species for poly-Arg complexed hGH or an hGH derivative crystal.

Figure 2:
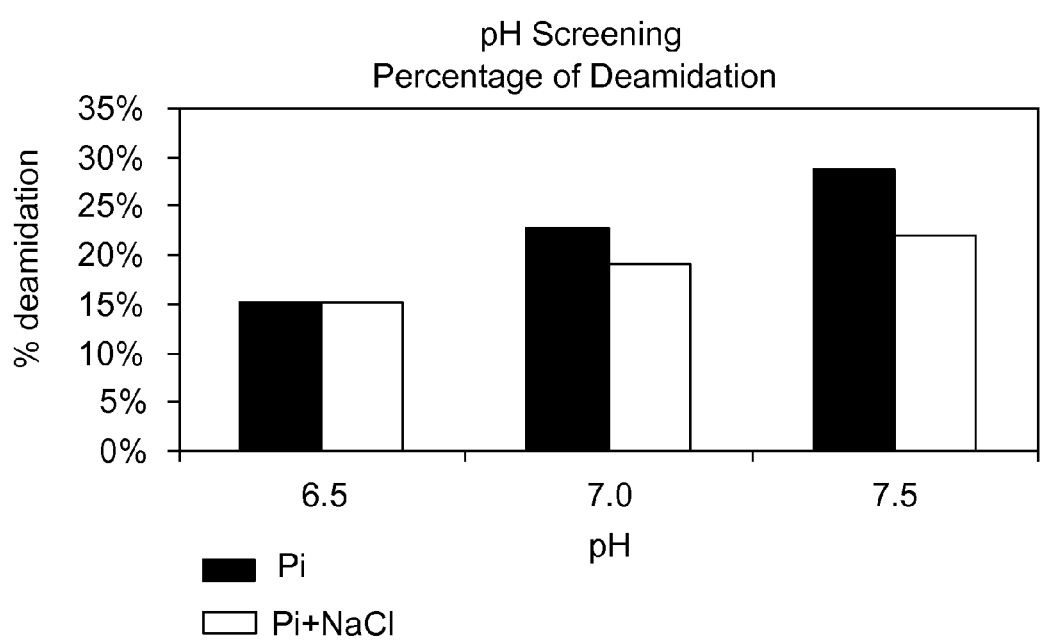
FIG. 2 is a graph showing that formulations containing sodium salt (higher ionic strength) have less degradation than formulations without salt by CEX. Stability data of one week at 40° C.

FIG. 2 shows the stability results of poly-Arg complexed hGH crystals at various pH values in the presence of NaCl to assess the effect of ionic strength. The figure demonstrates that increasing ionic strength does influence the rate of deamidation. With higher salt content, lower deamidation and oxidation level were observed after storage at 40° C.

Figure 3:
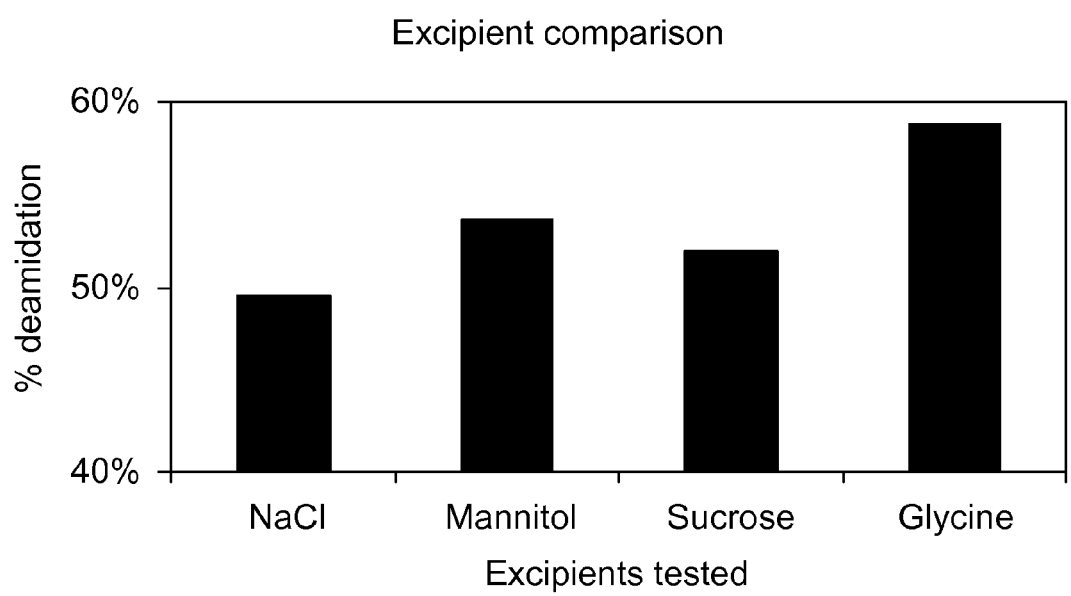
FIG. 3 is a graph showing the percentage of degradation for excipient screening, excipient screening by CEX after two weeks at 40° C.
Figure 4:
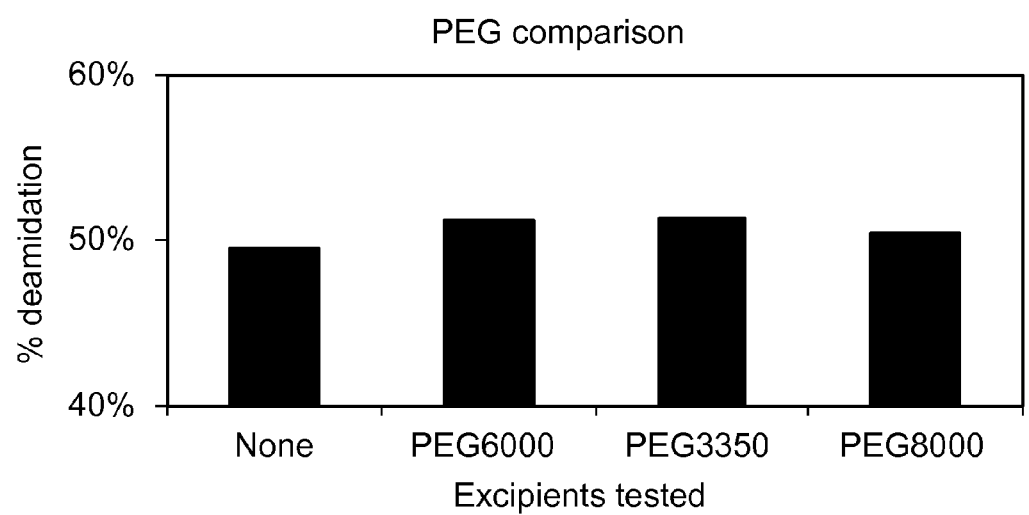
FIG. 4 is a graph showing the percentage of degradation (excipient) for various suspending agents at pH 6.8 by CEX. All formulations contained the following components: phosphate, NaCl at pH 6.8.
Figure 5:
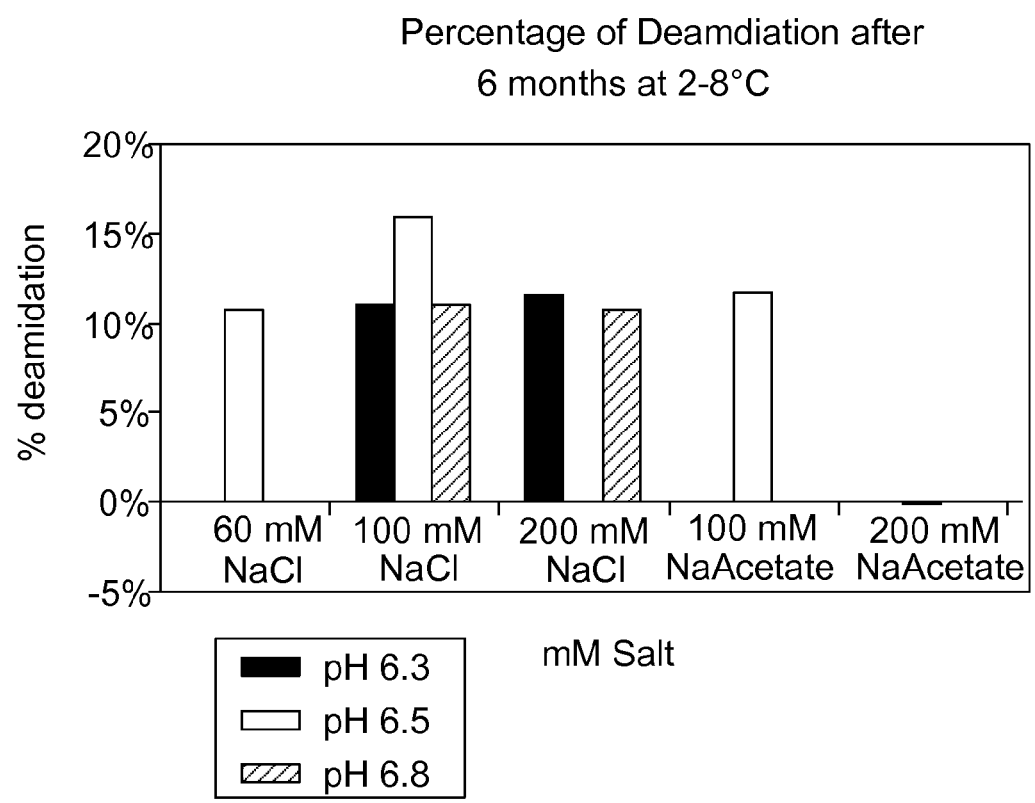
FIG. 5 is a graph showing the effects of salt species and concentration on degradation by CEX. All formulations contained the following components phosphate with either PEG6000 or PEG8000.

Polyethylene glycol ("PEG") is the suspending agent used in previous formulations. Alternative suspending agents such as PEG3350, PEG8000, mannitol and sucrose were compared. In addition, effect of replacing salt with glycine on deamidation rate or oxidation was evaluated. Phosphate buffer at pH 6.8 was used for this study. FIGS. 3 to 5 show the results. The formulations containing NaCl appear to have the least amount of deamidation. No significant differences are observed in chemical degradation for different salts (sodium acetate or sodium chloride) or suspending agents (PEG3350, PEG6000 or PEG8000) at the same pH of 6.8 (FIGS. 3 to 5). No significant differences were observed for the oxidation level among the tested formulation at the same pH.

In one embodiment, the preferred salt to be used for hGH complexed crystals is sodium acetate or sodium chloride. In a more preferred embodiment, the salt concentration for poly-Arg complexed crystals of hGH is 60 mM to 200 mM sodium salt.

Figure 6:
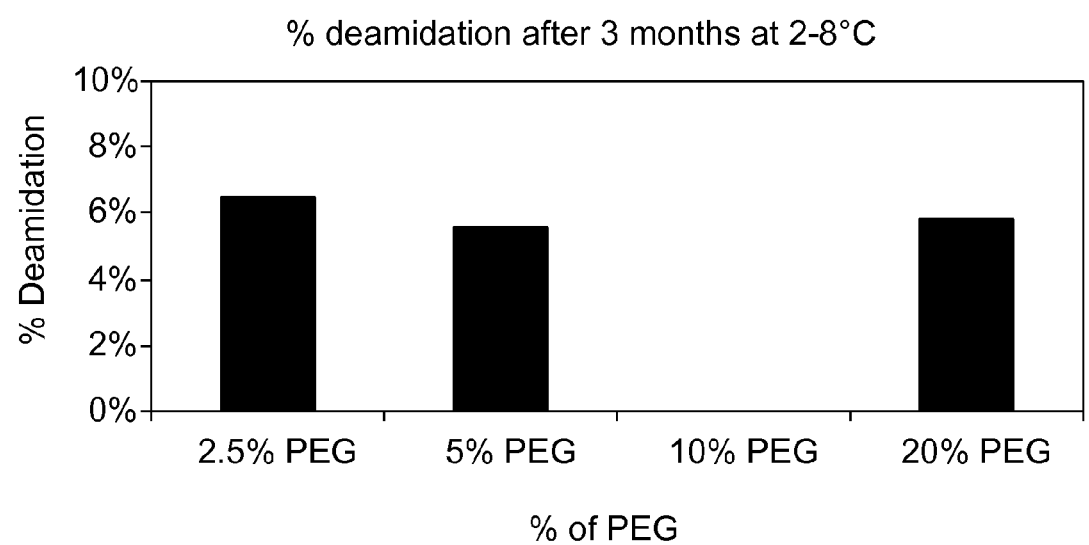
FIG. 6 is a graph showing percentage of degradation versus PEG concentration by CEX (10% PEG results not shown).
Figure 7A:
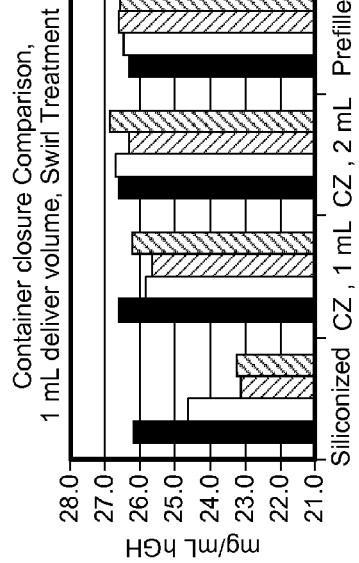
FIGS. 7A, 7B, 7C, and 7D are a series of graphs showing a recovered hGH concentration comparison.
Figure 7B:
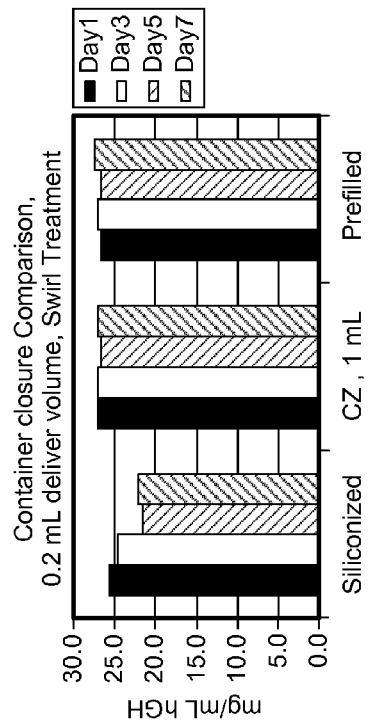
Figure 7C:
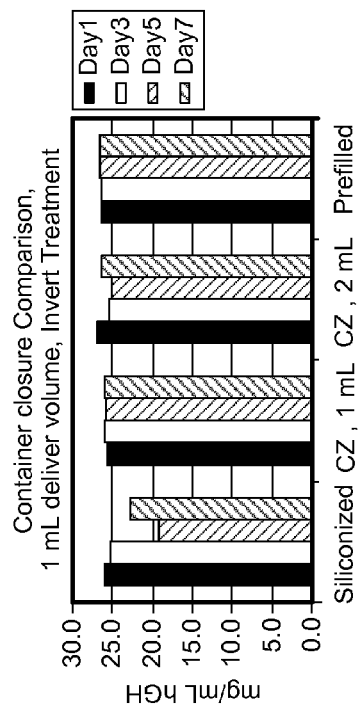
Figure 7D:
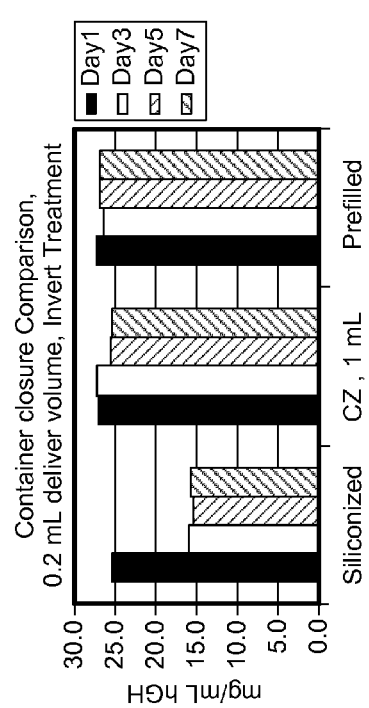
Figure 8B:
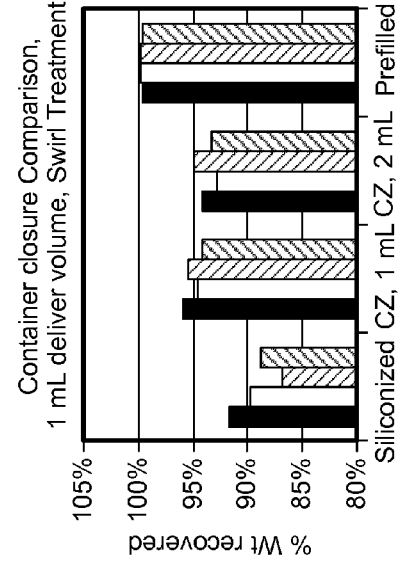
FIGS. 8A, 8B, 8C, and 8D are a series of graphs showing a percentage of weight recovery comparison.
Figure 8D:
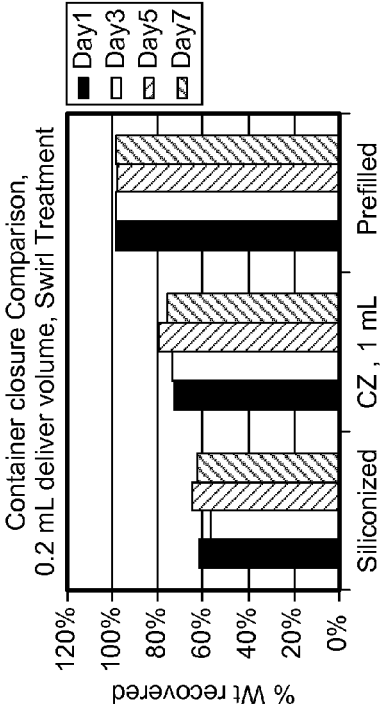
Figure 8A:
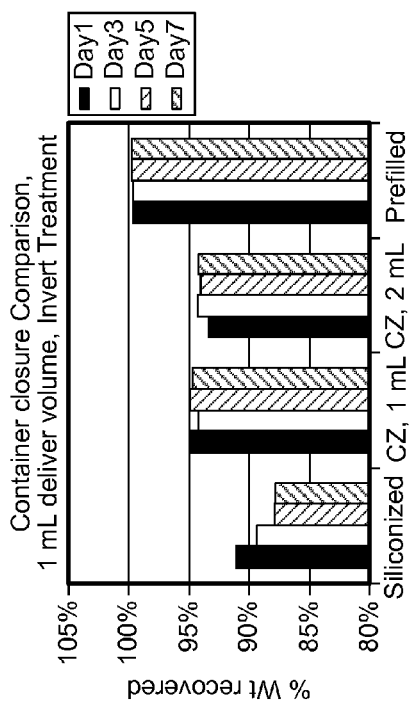
Figure 8C:
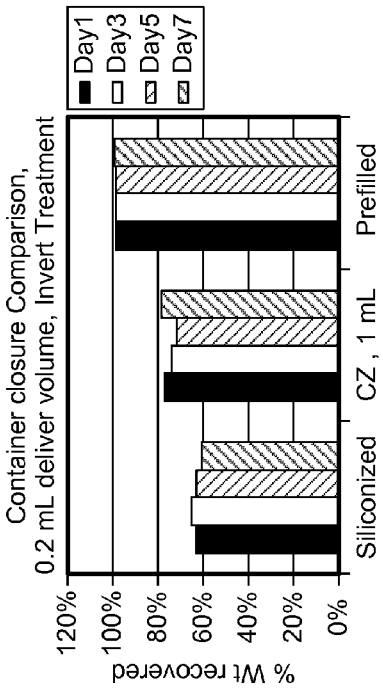

The concentration range of polyethylene glycol (2.5%, 5%, 10% and 20%) was also established. With no suspending agent, potential caking could be problematic. FIG. 6 shows the results of deamidation, and no difference in stability is observed. In addition, all samples could be resuspended within one minute with shaking In one embodiment, preferred PEG concentration to be used for hGH complexed crystals is between 2.5% to 20%.

These experiments also establish the hGH to poly-Arg ratios desired for the complexed crystals. The targeted ratio was between 3 to 11 for various lots of complexed protein. At the hGH/poly-Arg ratio of 3, the oxidation level is significantly higher than those at ratios of 7 and 15 at the elevated temperature. All samples used the same formulation containing of Tris, sodium acetate and PEG6000 at pH 7.5. However, no significant difference was observed for deamidation level.

The in vitro dissolution profile was performed on selected time point samples to evaluate any changes during the test period. The results indicated that there was no significant difference in the dissolution profiles among all tested hGH/poly-Arg ratios (Table 5). The preferred hGH/pR ratio is between 5 to 15.

TABLE 5

Summary of the in-vitro dissolution profile

| TARGETED HGH/PR RATIO | 3 MONTHS 5° C. RATE mg of hGH released/hr |
|---|---|
| 3 | 0.30 |
| 7 | 0.28 |
| 11 | 0.23 |

Crystals of hGH or an hGH derivative according to this disclosure form shining rod-like or needle-like morphologies when imaged with optical microscopy and SEM. In some embodiments, crystals of hGH or an hGH derivative form needles that are between about 0.1 and about 200 μm in length. In preferred embodiments, crystals of hGH or an hGH derivative form needles that are between about 2 and about 100 μm in length. In more preferred embodiments, crystals of hGH or an hGH derivative form needles that are between about 2 and about 25 μm in length for 50% mean particle size distribution.

The concentration of the poly-Arg complexed hGH crystals was also defined. The stability data ranging from 5 to 50 mg/mL of poly-Arg complexed hGH crystals demonstrated that there are no observed differences in stability. Based on the results, the free hGH and poly-Arg in the supernatant are comparable for all tested concentrations. However, at the 50 mg/mL level, the suspension was very thick and required more strength to eject the product. Therefore, in some embodiments hGH complexed crystal concentrations are 5 to 50 mg/mL. In preferred embodiments, the concentration should be between 20 to 30 mg/mL poly-Arg complexed hGH crystals.

The selection of container closure for hGH crystals focused on dose consistency. Vials and prefilled syringes that were made with various material siliconized and CZ resin were compared. Two different types of treatment, invert or swirl 10 times, were applied respectively to the vials/syringes for each configuration once per day. The extractable weight and ALTU-238 concentration were recorded at each time point (Day 1, Day 3, Day 5 and Day 7). The loss of product to prefilled syringes is much less than the vials by this agitation study due to the head space. FIGS. 7A-7D and 8A-D summarize the results.

Noticeable crystals were accumulated in the bottle neck of the vials, and crystals were stuck to the walls of container closure. Therefore, both the shape and head space of container closure impact delivered dose consistency. The prefilled syringes with stake needles appear to be most ideal for the limited dead volume (range from 2 to 5 μL) for hGH complexed crystals or any protein crystal products. There is no bottle neck for the prefilled syringes; the head space is also much smaller and can be controlled by the stopper placement; the plunger can push almost all of the crystal out of the syringe barrel (except the dead volume). However, these can be resolved if no head space is present in the container closure. Companies (e.g., Hyauron)) do fill material with no head space. In conclusion, for dose consistency, limited or no head space is preferred for container closures used for protein crystals. Prefilled syringes/stake needles and a head space of less than 10 mm are more suitable for protein crystal parenteral products.

Stoppers of Teflon coated (i.e. Diekyo Fluorotec) and 4432 formulation stoppers were tested as closures for pR complexed hGH crystals. The data indicate that both stoppers have no compatibility issues.

The fill volume, e.g., 0.2 to 1.0 mL, for poly-Arg coated hGH crystals was also examined. There are no differences among all tested fill volumes. hGH complexed crystals preferably have a fill volume between 0.2 mL to 1.0 mL.

Lead formulations were identified for Arrhenius stability prediction. The Arrhenius stress model (or relationship) has been widely used when the stimulus or acceleration variable (such as deamidation, oxidation, etc.) is thermal (i.e., temperature). The degradation rate at 5° C. can be predicted using stability results from several elevated temperatures. Samples of the poly-Arg complexed crystals in prefilled syringes with Fluoroteck stoppers were placed at 2-8° C., 25° C., 30° C., 35° C., 40° C. and 50° C. Based on the data reported, the Arrhenius equation was applied and degradation rate at 5° C. was predicted. The results were compared to the real stability of a previous lot that was analyzed by the same methods. In addition, the real time stability of the lead formulation was listed for comparison. It is estimated that and ~7% degradation increase after 24 months storage at 5° C. for the ALTU-238 by CEX (Tables 6 and 7)

TABLE 6

The prediction of percentage of deamidation of the dissolved crystals by CEX

| °C. | 1/T | PI, 100 MM NACL, PEG6000 | PI, 200 MM NACL, PEG6000 | lot 1 | lot 2 | lot 3 | #17 Tris, Na Acetate PEG6000 |
|---|---|---|---|---|---|---|---|
| 50° C. | 0.00310 | −3.29 | −3.32 | −3.34 | −3.27 | −3.26 | −3.16 |
| 40° C. | 0.00319 | −4.00 | −4.05 | −4.06 | −4.06 | −4.01 | −3.80 |
| 35° C. | 0.00325 | −4.78 | −4.87 | −4.92 | −4.86 | −4.78 | −4.57 |
| 30° C. | 0.00330 | −5.41 | −5.46 | −5.46 | −5.36 | −5.27 | −5.13 |
| 25° C. | 0.00336 | −5.73 | −5.73 | −5.55 | −5.37 | −4.96 | −4.92 |
| 5° C. | 0.00360 | −9.56 | −8.45 | −8.17 | −7.19 | −6.80 | −7.26 |
| Predicted LnK for 5° C. | 0.00360 | −9.25 | −8.40 | −8.13 | −7.32 | −6.89 | −7.23 |
| Predicted % deamidation Rate/day at 5° C. | | 0.000096 | 0.000225 | 0.000295 | 0.000665 | 0.001022 | 0.000727 |
| Corr. Coeff. | | 0.979 | 0.993 | 0.988 | 0.972 | 0.946 | 0.972 |
| Assumed 10% to start with, after 24 months | | 17.0% | 26.4% | 31.6% | 58.6% | 84.6% | 63.1% |

TABLE 7

Comparison of the predicted and actual percentage degradation results by CEX

Lead Formulation in phosphate, sodium chloride and PEG6000

| Time 0 Actual | 6 months at 5° C. Actual | 6 months at 5° C. Predicted |
|---|---|---|
| 12% | 11% | 14% |

Previous formulation in Tris, sodium acetate and PEG6000

| Time 0 Assumed | 15 months at 5° C. Actual | 15 months at 5° C. Predicted |
|---|---|---|
| 10% | 29% | 43% |

The dissolution profile of the formulations defined based on this disclosure was compared to the one used in the previous analyses by both dispersed dissolution profile assay and rat hypox study model. The results (Table 8) indicate that comparable dissolution rate and rat PD and PK profiles were attained. Therefore, the formulations defined herein can provide a controlled release profile of once per week injection for human therapy.

TABLE 8

Dispersed dissolution profile results from different study and time points. The correlation coefficient was calculated.

| stability time point | #1 Mg hGH/hr released | #2 Mg hGH/hr released | Correlation coefficient (r) |
|---|---|---|---|
| 1 Month at 25° C. | 0.21 | 0.19 | 0.83 |
| 3 Months at 5° C. | 0.25 | 0.24 | |
| 3 Months at 25° C. | 0.18 | 0.17 | |
| 3 Months at 5° C. | 0.23 | 0.22 | |
| 4 Months at 5° C. | 0.20 | 0.23 | |
| 2 Months at 5° C. | 0.25 | 0.26 | |
| Average | 0.22 | 0.22 | |
| RSD | 13% | 15% | |

No significant difference in the PD profile was observed between the previous and present formulations of ALTU-238 in a rat hypophysectomized model. No significant difference in body weight gain as well as pK profile was observed between the daily rhGH control, previous and present formulations in this hypophysectomized rat model. Mean body weight changes were 18%, 18%, and 16%, respectively.

Example 2

Studies were performed to prepare a target formulation of a poly-Arg complexed crystalline hGH suspension that is stable for about 18 to about 24 months at 5±3° C. (refrigerated) and at least one week at room temperature 25±2° C. (in use) conditions.

Both the stability of the hGH molecule and system stability were considered. Instability of molecule includes chemical degradation and aggregation. System stability should provide stability for 1-week long release profile and stability of the suspension including crystal aggregation, sedimentation and surface adsorption.

An array of analytical methods were used to study degradation in the complexed hGH formulations. Chemical stability or formation of hGH-related impurities was monitored with RP-HPLC and IEX-HPLC assays. Aggregation was monitored using SE-HPLC assays. Changes in particle size distribution were studied with a laser light scattering technique. Changes in suspension appearance was observed visually.

Control stability measurements were based on five representative batches of previous formulations. For example, regarding chemical stability, the stability of a previous formulation is 8 to 12 months at 2-8° C. and 1 to 3 months at room temperature.

Regarding aggregation, the projected stability is more than three years at 2-8° C. and 1 to 3 years at room temperature. The previous suspension is stable with respect to particle size distribution, appearance and sedimentation over a two year observation period.

Chemical instability in hGH molecules can include deamidation, formation of succinimide intermediates, oxidation, and clipping. The optimizations described herein help to increase hGH chemical stability in complexed hGH formulations.

Degradation of hGH may be process induced degradation and/or formulation induced degradation. Formulation derived degradation may be a consequence of using a suboptimal formulation vehicle composition and the components and characteristics of the vehicle, such as pH, buffer, salt, suspending agent, preservative, and contaminants derived from these components.

During these studies, conditions influencing hGH stability in crystalline hGH suspensions coated with poly-Arginine were studied. Formulation vehicles allowing for increased hGH stability were identified. The formulations were similar to previous formulations in terms of therapeutic action.

An experiment was performed to study the influence of pH and buffer composition on hGH chemical stability in formulations. hGH crystals complexed to poly-Arginine were resuspended in formulation vehicles listed in Table 9. hGH concentration in the samples was 25 mg/mL and poly-Arginine content was about 5 mg/ml. Samples were stored at 5±3° C. and 25±2° C. conditions.

TABLE 9

Compositions of formulation vehicles (pH screen)

| Lot # | Composition | pH |
|---|---|---|
| 1 | 25 mM Tris, 100 mM NaAc, 5% PEG 6000 | 8.0 |
| Previous formulation (ALTU-238; Control) | 25 mM Tris, 100 mM NaAc, 5% PEG 6000 | 7.5 |
| 3 | 25 mM Tris, 100 mM NaAc, 5% PEG 6000 | 7.0 |
| –4 | 10 mM Histidine, 25 mM Tris, 100 mM NaAc, 5% PEG 6000 | 7.0 |
| 5 | 10 mM Histidine, 25 mM Tris, 100 mM NaAc, 5% PEG 6000 | 6.5 |
| 6 | 10 mM Histidine, 25 mM Tris, 100 mM NaAc, 5% PEG 6000 | 6.0 |
| 7 | 25 mM Tris, 100 mM NaAc, 5% PEG 6000 | 5.5 |
| 8 | 25 mM Tris, 100 mM NaAc, 5% PEG 6000 | 5.0 |

At the beginning of study, purity of the control sample was determined (Table 10). After 1 month storage at room temperature, samples were analyzed with reverse phase (RP-HPLC) and anion exchange (IEX-HPLC) HPLC (IEX-HPLC results are shown in Table 10).

TABLE 10

Time 0 characterization of control sample

| Lot # | pH | Buffer component | RP-HPLC, % | IEX-HPLC, % |
|---|---|---|---|---|
| Control | 7.5 | Tris | 95.99 | 94.53 |

TABLE 11

Characterization of samples stored 1 month at 25 ± 2° C.

| Lot # | pH | Buffer component | RP-HPLC, % | IEX-HPLC, % |
|---|---|---|---|---|
| 1 | 8.0 | Tris | 90.59 | 78.01 |
| Control | 7.5 | Tris | 92.53 | 80.70 |
| 3 | 7.0 | Tris | 91.78 | 86.33 |
| 4 | 7.0 | Histidine | 82.03 | 85.31 |
| 5 | 6.5 | Histidine | 79.00 | 88.70 |
| 6 | 6.0 | Histidine | 69.00 | 88.96 |
| 7 | 5.5 | Acetate | 81.81 | 90.89 |

To our surprise, based on RP-HPLC stability data, buffer components influenced chemical stability of the formulations. Surprisingly, histidine buffer was found to cause significantly faster chemical degradation in formulations. Thus, the buffer component has a strong influence on hGH chemical degradation as analyzed by RP-HPLC. In the range of explored buffers under the test conditions, the optimal pH was 7.5 with decreasing stability on either extreme of this value.

Interestingly, according to IEX-HPLC, deamidation is strongly influenced by the pH of the formulation vehicle. Higher pH promotes deamidation. With decreasing pH, deamidation rate decreased significantly (Table 11).

Based on data from this example, overall hGH chemical degradation in complexed hGH formulations was found to be influenced by buffer component, composition of formulation vehicle, and pH. Based on these data, further screens were performed to vary these parameters in order to get increased chemical stability of hGH protein while maintaining other parameters of the hGH formulation.

In order to screen for an improved stability formulation, additional formulation vehicles were tested (Tables 12-16). hGH crystals complexed to poly-Arginine were resuspended in formulation vehicles to yield an hGH concentration of 25 mg/mL. Stability was studied after samples were stored at 5±3° C. and 25±2° C. conditions.

TABLE 12

Compositions of formulation vehicles (pH screen)

| Lot # | Composition | pH |
|---|---|---|
| 9 | 10 mM Histidine, 25 mM Tris, 100 mM NaAc, 5% PEG 6000 | 7.5 |
| 10 | 10 mM Histidine, 25 mM Tris, 100 mM NaAc, 5% PEG 6000 | 6.5 |
| 11 | 10 mM Histidine, 25 mM Tris, 100 mM NaAc, 5% PEG 6000 | 6.0 |
| 12 | 10 mM Na Phosphate, 25 mM Tris, 100 mM NaAc, 5% PEG 6000 | 7.5 |
| 13 | 10 mM Na Phosphate, 25 mM Tris, 100 mM NaAc, 5% PEG 6000 | 6.5 |
| 14 | 10 mM Na Phosphate, 25 mM Tris, 100 mM NaAc, 5% PEG 6000 | 6.0 |
| 15 | 10 mM Ethanolamine, 25 mM Tris, 100 mM NaAc, 5% PEG 6000 | 7.5 |
| 6 | 10 mM Triethanolamine, 25 mM Tris, 100 mM NaAc, 5% PEG 6000 | 7.5 |
| 17 | 10 mM Triethanolamine, 25 mM Tris, 100 mM NaAc, 5% PEG 6000 | 6.8 |
| 18 | 10 mM Ethanolamine, 25 mM Tris, 100 mM NaAc, 5% PEG 6000 | 6.5 |
| 19 | 10 mM Ethanolamine, 25 mM Tris, 100 mM NaAc, 5% PEG 6000 | 6.0 |

TABLE 13

Compositions of formulation vehicles in additional pH screen

| Lot # | Composition | pH |
|---|---|---|
| 21 | 10 mM Ethanolamine, 25 mM Tris, 100 mM NaAc, 5% PEG 6000 | 7.0 |
| 22 | 10 mM Triethanolamine, 25 mM Tris, 100 mM NaAc, 5% PEG 6000 | 7.0 |
| 23 | 30 mM Triethanolamine, 100 mM NaAc, 5% PEG 6000 | 6.8 |
| 24 | 50 mM Triethanolamine, 100 mM NaAc, 5% PEG 6000 | 6.8 |
| 25 | 50 mM Triethanolamine, 100 mM NaAc | 6.8 |
| 26 | 50 mM Triethanolamine, 100 mM NaCl | 6.8 |
| 27 | 50 mM Triethanolamine, 4% Mannitol | 6.8 |

TABLE 14

Compositions of formulation vehicles

| Lot # | Composition | pH |
|---|---|---|
| 55-01 | 10 mM Histidine, 0.3% Poloxamer 188, 0.3% Phenol, 4% Mannitol | 6.0 |
| 55-2 | 10 mM Histidine, 0.3% Poloxamer 188, 0.3% Phenol, 4% Mannitol | 6.5 |
| 55-3 | 10 mM Histidine, 0.3% Poloxamer 188, 0.3% Phenol, 4% Mannitol | 7.0 |
| 55-4 | 10 mM Histidine, 0.3% Poloxamer 188, 0.3% Phenol, 4% Mannitol | 7.4 |

TABLE 15

Compositions of formulation vehicles

| # | Composition | pH |
|---|---|---|
| 55-01n | 10 mM Na Citrate, 0.2% w/v Polysorbate 20, 0.25% w/v Phenol, 150 mM NaCl PH 6.0* | 6.0 |
| 55-2n | 10 mM Na Citrate, 0.25% w/v Phenol, 150 mM NaCl pH 6.0 | 6.0 |
| 55-3n | 10 mM Na Citrate, 0.2% w/v Polysorbate 20, 150 mM NaCl | 6.0 |
| 55-4n | 10 mM Na Citrate, 150 mM NaCl | 6.0 |
| 55-5n | 10 mM Na Citrate, 75 mM NaCl, 75 mM NaAc | 6.0 |
| 55-6n | 10 mM Na Citrate, 150 mM NaAc | 6.0 |
| 55-7n | 10 mM Na Citrate, 125 mM NaCl, 5% PEG6000 | 6.0 |
| 55-8n | 10 mM Na Citrate, 150 mM NaAc, 5% PEG6000 | 6.0 |
| 55-9n | 10 mM Na Citrate, 25 mM Tris 125 mM NaAc, 5% PEG 6000 | 6.0 |
| 55-10n | 10 mM Na Citrate, 25 mM Tris 125 mM NaAc, 5% PEG 6000 | 7.5 |
| 55-11n | 10 mM Na Citrate, 25 mM Tris 125 mM NaCl, 5% PEG 6000 | 7.5 |
| 55-12n | 25 mM Tris, 100 mM NaCl, 5% PEG 6000 | 7.5 |
| 55-13n | 25 mM Tris 125 mM NaCl | 7.5 |
| 55-14n | 25 mM Tris, 100 mM Na Ac | 7.5 |
| 55-15n | 25 mM Tris, 100 mM NaAc, 0.2% w/v Polysorbate 20, 0.25% w/v Phenol, 5% PEG 6000 | 7.5 |

TABLE 16

Compositions of formulation vehicles in additional pH screen

| # | Composition | pH |
|---|---|---|
| 57-01 | 25 mM Imidazole, 100 mM Na Acetate, 5% w/v PEG6000 | 6.5 |
| 57-02 | 25 mM Imidazole, 100 mM Na Acetate, 5% w/v PEG6000 | 7.0 |
| 57-03 | 25 mM Imidazole, 100 mM Na Acetate, 5% w/v PEG6000 | 7.5 |
| 57-04 | 10 mM Methionine, 25 mM Tris, 100 mM Na Acetate, 5% w/v PEG6000 | 7.5 |
| 57-05 | 10 mM EDTA, 25 mM Tris, 100 mM Na Acetate, 5% w/v PEG6000 | 7.5 |
| 57-06 | 25 mM Tris, 100 mM Na Acetate, 2% w/v PEG6000 | 7.5 |
| 57-07 | 25 mM Tris, 100 mM Na Acetate, 2% w/v PEG3350 | 7.5 |
| 57-08 | 50 mM Triethanolamine, 25 mM Tris, 100 mM Na Acetate, 2% w/v PEG3350 | 7.5 |
| 57-09 | 50 mM Triethanolamine, 100 mM NaCl, 2% w/v PEG3350 | 7.5 |
| 57-10 | 25 mM Triethanolamine, 10 mM Methionine, 100 mM NaCl, 2% w/v PEG3350 | 6.8 |

Based on results from 1 and 3 months stability time-points, preferred stability formulations were identified (Table 17). Preferred stability formulation selections were also based on crystallinity, poly-Arg content, and dissolution properties.

TABLE 17

Optimum stability formulations

| Lot # | Composition | pH |
|---|---|---|
| 02 (Control) | 25 mM Tris, 100 mM Na Acetate, 5% w/v PEG6000 | 7.5 |
| 13 | 10 mM Na Phosphate, 25 mM Tris, 100 mM NaAc, 5% PEG 6000 | 6.5 |
| 23 | 30 mM Triethanolamine, 100 mM Na Acetate, 5% w/v PEG6000 | 6.8 |
| 24 | 50 mM Triethanolamine, 100 mM Na Acetate, 5% w/v PEG6000 | 6.8 |
| 55-01 | 10 mM Histidine, 0.3% Poloxamer 188, 0.3% Phenol, 4% Mannitol | 6.0 |
| 55-01N | 10 mM Na Citrate, 0.2% Tween 20, 0.25% Phenol, 150 mM NaCl | 6.0 |
| 57-01 | 25 mM Imidazole, 100 mM Na Acetate, 5% w/v PEG6000 | 6.5 |
| 57-10 | 25 mM Triethanolamine, 10 mM Methionine, 100 mM NaCl, 20% w/v PEG3350 | 6.8 |

At 6 months time-point samples stored at refrigerated and room temperature conditions analyzed (Table 19 and 20). Purity compared to control sample $O_2$ which represent composition identical to the control formulation. Time 0 purity results of control sample described in Table 18.

TABLE 18

Time 0 characterization of control sample

| | RP-HPLC | | IEX-HPLC | |
|---|---|---|---|---|
| # | %, Main peak | %, Impurities | %, Main peak | %, Deamidated |
| 02 (Control) | 95.99 | 4.01 | 94.53 | 5.47 |

TABLE 19

Characterization of sample stored 6 months at 5 ± 3° C.

| | RP-HPLC | | IEX-HPLC | |
|---|---|---|---|---|
| Lot # | %, Main peak | %, (Total Impurities | %, Main peak | %, Deamidated |
| 02 (Control) | 90.62 | 9.38 | 87.67 | 12.33 |
| 13 | 92.85 | 7.15 | 92.39 | 7.61 |
| 23 | 93.27 | 6.73 | 90.59 | 9.41 |
| 24 | 93.20 | 6.80 | 90.74 | 9.26 |
| 55-01 | 91.57 | 8.43 | 91.24 | 8.76 |
| 55-01N | 93.29 | 6.71 | 93.51 | 6.49 |
| 57-01 | 92.55 | 7.45 | 90.64 | 9.36 |
| 57-10 | 92.88 | 7.12 | 90.37 | 9.63 |

TABLE 20

Characterization of sample stored 6 months at 25 ± 2° C.

| | RP-HPLC | | IEX-HPLC | |
|---|---|---|---|---|
| Lot # | %, Main peak | %, Total Impurities | %, Main peak | %, Deamidated |
| 02 (Control) | 72.18 | 27.82 | 49.27 | 50.73 |
| 13 | 78.36 | 21.64 | 65.26 | 34.74 |
| 23 | 79.12 | 20.88 | 60.76 | 39.24 |
| 24 | 79.51 | 20.49 | 60.58 | 39.42 |
| 55-01 | 71.45 | 28.55 | 59.88 | 40.12 |
| 55-01N | 80.11 | 19.89 | 76.79 | 23.21 |
| 57-01 | 79.01 | 20.99 | 56.34 | 43.66 |
| 57-10 | 72.18 | 27.82 | 49.27 | 50.73 |

Methodology of estimation of degradation rates and selection of optimum formulations: Degradation rates were used to compare formulations and identify optimum stability formulations. Degradation rates are expressed as rate of accumulation of hGH related substances. Rates are calculated as the difference between degradation product content at Time 0 and 6 months divided by number of months (6 months in current case) stored at refrigerated condition.

Percent of impurity is determined as the content of all peaks besides the main peak on respective HPLC chromatograms. Chemical degradation other than deamidation was determined by RP-HPLC. Deamidation was determined by IEX-HPLC.

Degradation rates were calculated as the difference between the content of degradation products in the sample at given time-point (6 months) and at the beginning of the study divided by duration of observation period (6 months). The chemical degradation rate was expressed through combining degradation rates obtained with RP-HPLC and IEX-HPLC. Formulations with lowest degradation rates are the optimum formulations. Degradation rates in samples stored 6 months at 5±3° C. are given in Table 21.

TABLE 21

Degradation rates in samples stored 6 months at 5 ± 3° C.

| Lot # | RP-HPLC, %/Month | IEX-HPLC, %/Month | Degradation rate, %/month |
|---|---|---|---|
| 02 — Control | 0.90 | 1.14 | 2.0 |
| 13 | 0.52 | 0.36 | 0.9 |
| 23 | 0.45 | 0.66 | 1.1 |
| 24 | 0.47 | 0.63 | 1.1 |
| 55-01 | 0.74 | 0.55 | 1.3 |
| 55-01N | 0.45 | 0.17 | 0.6 |
| 57-01 | 0.57 | 0.65 | 1.2 |
| 57-10 | 0.52 | 0.69 | 1.2 |

In order to compare stability, purity of historical previous batches were determined (Table 22) and degradation rates were calculated (Table 23). Degradation rates in historical batches were compared to the control sample and to the new formulations.

TABLE 22

Characterization of historical Phase I ALTU-238 batches stored at 5 ± 3° C.

| Lot # | Months stored at 5° C. | T0 RP-HPLC, % | RP-HPLC, % | T0 IEX-HPLC, % | IEX-HPLC, % |
|---|---|---|---|---|---|
| 204-35-01 | 14.0 | 96.00 | 89.66 | 95.00 | 80.00 |
| 161-29-2 | 23.0 | 97.00 | 83.51 | 95.00 | 70.00 |
| 05-021-001 | 12.0 | 96.00 | 88.49 | 95.00 | 77.52 |
| 161-93-08 | 16.5 | 98.50 | 78.41 | 95.00 | 61.34 |

TABLE 23

Degradation rates and shelf-life of historical batches stored at 5 ± 3° C.

| Lot # | RP-HPLC, %/Month | IEX-HPLC, %/Month | Degradation rate, %/month |
|---|---|---|---|
| 204-35-01 | 0.45 | 1.07 | 1.5 |
| 161-29-2 | 0.59 | 1.09 | 1.7 |
| 05-021-001 | 0.63 | 1.48 | 2.1 |
| 161-93-08 | 1.22 | 2.04 | 3.3 |

Surprisingly, degradation rates in the optimized formulations were significantly lower than in the control sample and in the historical batches. In current screens several formulations were identified with greatly decreased degradation rates. Two preferred improved stability formulations were identified: #13 (10 mM Na2HPO4, 25 mM Tris, 100 mM NaAc, 5% PEG 6000, pH 6.5) and #55-01N (10 mM Na Citrate, 0.2% Tween20, 0.25% Phenol, 150 mM NaCl pH 6.0).

Estimation of Room Temperature Degradation Rates

Analysis of the stability of the new formulations at room temperature yielded the same improved stability formulation #55-01N (Table 24). Other formulations identified as optimal at refrigerated storage conditions had better stability than the control formulation when stored at room temperature.

TABLE 24

Degradation rates and shelf-life of samples stored 6 months at 25 ± 2° C.

| Lot # | RP-HPLC, %/Month | IEX-HPLC, %/Month | Degradation Rate, %/month |
|---|---|---|---|
| 02 - control | 3.97 | 7.54 | 11.51 |
| 13 | 2.94 | 4.88 | 7.82 |
| 23 | 2.81 | 5.63 | 8.44 |
| 24 | 2.75 | 5.66 | 8.41 |
| 55-01 | 4.09 | 5.78 | 9.87 |
| 55-01N | 2.65 | 2.96 | 5.61 |
| -57-10 | 2.83 | 6.37 | 9.20 |

Experiments were performed to see how the new formulation vehicles that provide improved chemical stability influence hGH aggregation in suspensions of hGH crystals complexed to poly-Arginine. hGH crystals complexed to poly-Arginine were resuspended in optimized stability formulation vehicles. Aggregation was studied using SE-HPLC after samples were stored at 5±3° C.

TABLE 25 hGH aggregation samples stored 6 months at 5 ± 3° C.

| Lot # | Formulation vehicle | SE-HPLC, % at time 0 | SE-HPLC, % at 6 months | Aggregation rate, %/month |
|---|---|---|---|---|
| 333-3-01 | 25 mM Tris, 100 mM NaAc, 5% PEG 6000 pH 7.5 - Control | 99.94 | 99.57 | 0.06 |
| 333-3-02 | 10 mM Na Citrate, 0.2% Tween20, 0.25% Phenol, 150 mM NaCl pH 6.0 - FV in the sample 55-01N | 99.94 | 99.64 | 0.05 |
| 333-3-13 | 10 mM Na$_2$HPO$_4$, 25 mM Tris, 100 mM NaAc, 5% PEG 6000, pH 6.5 FV in the sample 13 | 99.94 | 99.79 | 0.025 |

To our surprise, the new formulation vehicles did not increase aggregate formation rate in suspensions of hGH crystals complexed to poly-Arginine. Indeed, for some of the optimized stability formulations, aggregated hGH formation rate decreased two fold as compared control sample (Table 25).

In Vivo Results: Hypophysectomized Rat Study

These experiments were performed to determine whether the therapeutic action of poly-Arginine complexed hGH crystals in optimized stability formulations vehicles is equivalent to the hGH release profile of the control formulation. No significant difference in the therapeutic action was observed between a control lot and an optimized stability formulation Lot# 299-35-06 (10 mM Na Citrate, 0.2% Tween20, 0.25% Phenol, 150 mM NaCl pH 6.0) in hypophysectomized male Wistar rats.

The efficacy confirmation in the standard rat weight gain assay is an important step for the clinical and commercial development of an hGH formulation. Test or control material was administered to hypophysectomized male Wistar rats (9 rats/group) by SC (subcutaneous) injection. The study compared the growth of hypophysectomized rats after receiving a single SC injection of 5.6 mg/kg of single-dose and multi-dose control and new formulations or daily SC injections of 0.8 mg/kg of soluble commercial rhGH (Nutropin AQ) for 7 days (i.e. 5.6 mg/kg/week). Body weights were measured weekly prior the start of dosing and daily from Day −7 (seven days prior dosing) until the end of observation period on day 8. No significant difference in body weight gains were observed between the daily rhGH injection formulation, the control, and the optimized stability formulation in this hypophysectomized rat model; mean body weight changes were 18±3%, 18±2%, and 16±4%, respectively.

Conclusions

These studies have identified formulation vehicles for suspensions of hGH crystals coated with poly-Arginine in formulation vehicles. The formulations:

a) provide improved stability
b) maintain crystallinity in the complex comparable to the control formulation
c) allow administration through 29 or finer gauge needle These formulations provide:

a) suspension of hGH crystals coated with polyelectrolyte where crystalline hGH concentration in the range of 5-100 mg/mL, preferably 10-50 mg/mL, more preferably in the range of 20 to 30 mg/mL.

b) suspension in formulation vehicles comprised of biologically compatible buffers that maintain crystallinity of the hGH complexes with pH in the range of 5.0 to 8.0. Buffer salt concentration in the range of 1 to 150 mM concentration. Preferably, 2-50 mM; more preferably 10 mM concentration. The examples of buffer salts include: acetate, triethanolamine, imidazole, phosphate, citrate, Tris-HCl. A preferred buffer is sodium phosphate in the pH range of 5.8 to 7.0, preferably 6.0 to 6.5. A combination of buffers, e.g., sodium phosphate and sodium citrate buffers, can be used, for example, 2 mM Na citrate 8 mM Na phosphate.

c) Components maintaining or increasing crystallinity of the hGH complex. As example is a neutral salt such as Na Acetate or polyethylene glycol (PEG 3350-PEG 8000). Preferred PEG concentrations range from 1-25 w/v %, more preferred 2-10 w/v %; more preferred 4-6 w/v %. Phenol can be used at concentrations of 0.1-0.5%.

d) Tonicity modifiers allowing for total osmolality of the compositions in the range of 250-450 mOsm/kg, preferably 270-350 mOsm/kg, more preferably 280-330 mOsm/kg. Examples include neutral salts such as sodium chloride, sodium acetate, Tris-HCl. Buffer salt outside of their working buffering pH range could be used as neutral salts. A preferred salt is sodium acetate or sodium chloride. Salts of amino acids could be used as neutral salts in the pH ranges outside their buffering pH range. Preferred salt of amino acids is glycine sodium salt. Polyols as mannitol, sorbitol also could be used as tonicity modifier. Polyethylene glycols could be used as tonicity modifiers.

e) Optionally, a preservative, e.g., phenol at a concentration of about 0.25% w/v. Preferred phenol concentration ranges are between 0.2-0.3%.

f) Optionally components increasing chemical stability of said formulation such as methionine, EDTA, etc.

Specific Examples of Lead Formulation Vehicles:

10 mM Na Phosphate, 25 mM Tris, 100 mM NaAc, 5% PEG 6000, pH 6.5
10 mM Na Phosphate, 0.25% Phenol, 150 mM NaCl, 5% PEG 6000 pH 6.0
10 mM Na Citrate, 0.2% Tween 20, 0.25% Phenol, 150 mM NaCl, pH 6.0
30 mM Triethanolamine, 100 mM Na Acetate, 5% PEG6000 pH 6.8
25 mM Triethanolamine, 10 mM Methionine, 100 mM NaCl, 2% PEG3350 pH 6.8
25 mM Imidazole, 100 mM Na Acetate, 5% PEG6000 pH 6.5

Specific Examples of Potentially Beneficial Formulations Vehicles:

2 mM Na citrate, 8 mM Na phosphate, 120 mM NaCl, 0.3% Phenol pH 6.0
10 mM Na Phosphate, 100 mM Glycine, 0.3% phenol, pH 6.0
10 mM Na Phosphate, 100 mM NaCl, 0.3% phenol, pH 6.0
10 mM Na Phosphate, 100 mM Na acetate, 5% PEG 6000, pH 6.0
10 mM Na Phosphate, 100 mM NaCl, 5% PEG 6000, pH 6.0
10 mM Na Phosphate, 100 mM NaCl, 5% PEG 6000, pH 6.5
2 mM Na citrate, 8 mM Na phosphate, 120 mM NaCl, 0.3% Phenol pH 5.4
10 mM Na phosphate, 100 mM NaCl, 10% w/v PEG3350 pH 6.0
10 mM Na citrate, 80 mM Na Glycine, 10% w/v PEG6000 pH 5.4
10 mM Na acetate, 120 mM NaCl, 10% w/v PEG6000 pH 5.6

Preparations of Said Formulations: Protocol (1) Production of poly-Arginine complexed hGH crystal, 25 mg/ml (Govardhan et al., 2004: WO 2004/060310)
(2) Centrifugation of step 1 product, 3,5000 rpm, 15 min, 4° C.
(3) Remove supernatant, record volume.
(4) Add same volume formulation vehicle.
(5) Resuspend the pellet.
(6) Repeat step 3, then add volume of formulation vehicle to get desired hGH concentration upon resuspension and resuspend.
(7) Store the final suspension at 2-8° C.

Samples are analyzed with gradient low pH RP-HPLC method to monitor chemical degradation excluding deamidation; deamidation is detected with use of cation exchange HPLC; finally chemical degradation is expressed through combining impurity numbers obtained with RP-HPLC and IEX-HPLC. SE-HPLC is used to monitor aggregation. Ratio of bound to free poly-Arginine calculated based on RP-HPLC determined concentration of total and supernatant located poly-Arginine. Crystallinity determined as ratio of hGH concentration in supernatant to the hGH concentration in crystalline phase of formulation by RP-HPLC calibration.

Sample preparation for HPLC analysis: Crystals dissolved to perform RP-, IEX- and SE-HPLC analyses. Crystals are centrifuged and supernatant removed; crystalline pellet is dissolved in acetic acid water solution with pH 2.8 in order to give 2 mg/mL concentration. After 2 minutes of incubation, solutions are centrifuged 4 minutes at 12000 rpm. Samples are then analyzed using HPLC.

RP-HPLC: RP-HPLC is used to determine the purity of hGH using RP-HPLC method a C5 Supelco Discovery Bio Wide Pore Column, 5 cm×4.6 mm, 3 µm particle size, 30 nm Pore size is used. The column thermostat temperature is set to 37° C. 10 µL of sample at 2 mg/mL concentration is injected. The elution is carried out at a flow rate of 1.0 mL/min with a gradient system present by mobile phase A (0.1% TFA in water) and mobile phase B (0.1% TFA in MeCN). The gradient system is changed from 5% B to 50% B from 0-2.5 min., then 50% to 70% B in 2.5-15.5 min. then, 70% to 90% in 15.5 to 17 min. Immediately following, 5% B is re-established for a 3 min. post-time. Detection is performed at 214 nm. The resulting chromatogram is manually integrated. Percent purity is calculated based on peak area.

IEX-HPLC Weak Anion Exchange Chromatography: WAX-hGH method is used as deamidation specific measure in stability testing at Time 0 point. To determine the purity of hGH using the WAX method, a PolyMA WAX (Supelco cat #59602-U) is used. The column thermostat temperature is set to 37° C. 54 of sample at 2 mg/mL concentration is injected. The elution is carried out at a flow rate of 0.5 mL/min with a gradient system present by mobile phase A (50 mM TRIS, pH 8.0) and mobile phase B (50 mM TRIS, pH 8.0 500 mM NaCl). The gradient system is changed from 5% B to 30% B from 0-30 min., then 30% to 50% B in 30 to 40 min. then, 50% to 95% in 40 to 42 min. 95% B is kept until 45 min. following, 50% B is re-established for a 3 min. post-time. Detection is performed at 214 nm and 280 nm. The resulting chromatogram is manually integrated. Percent purity is calculated based on peak area.

IEX-HPLC Strong Cation Exchange Chromatography: SCX-hGH method is used as deamidation specific in stability testing. To determine the purity of hGH using the IEX-HPLC method, a PolyLC (NEST Group cat #P054SE0503) is used. The column thermostat temperature is set to 30° C. 20 µL of sample at 2 mg/mL concentration is injected. The elution is carried out at a flow rate of 1 mL/min with a gradient system present by mobile phase A (50 mM Na Acetate, pH 4.6) and mobile phase B (50 mM Na Acetate, pH 4.6 250 mM NaCl). The gradient system is changed from 0% B to 20% B from 0 to 5 min., then 20% to 70% B in 5 to 25 min. then, 70% to 100% in 25 to 25.1 min. 100% B is kept until 27 min. following 27.1 min, 0% B is re-established for a 5 min. post-time. Detection is performed at 214 nm and 280 nm. The resulting chromatogram is manually integrated. Percent purity is calculated based on peak area.

SE-HPLC: used to determine aggregate content in samples. SE-HPLC Phenomenex BioSep SEC-S-2000 column is used. 10 µl of 2 mg/mL concentration sample is injected into the column. The running buffer is composed of 3% IPA and 60 mM sodium phosphate, pH 7.0. The flow rate is set to 0.6 mL/min and the run time is 30 min. Detection is performed at 214 nm. The resulting chromatogram is manually integrated. Percent purity is calculated based on peak area.

Crystallinity: Crystallinity is calculated as ratio of hGH concentration (based on RP-HPLC calibration) in supernatant to the total hGH concentration in sample.

$$\text{Crystallinity} = ((C_{hGHtotal} - Ch_{GHsupernatant})/C_{hGHtotal}) \times 100\%$$

Ratio of Bound to Free Poly-Arginine: ratio is calculated based on RP-HPLC determined (based on poly-Arginine calibration) concentration of total and supernatant located poly-Arginine.

$$\text{Poly-Argininty} = ((C_{poly-Rtotal} - C_{poly-Rsupernatant})/C_{poly-Rtotal}) \times 100\%$$

Visual Appearance: visual appearance of the test articles assessed visually to detect any relevant changes in the test article.

Example 3

This disclosure relates to the field of sustained release multi-dose suspensions of hGH crystals complexed with poly-electrolyte.

Some liquid formulations of human growth hormone are multi-dose formulations. They contain antimicrobial preservatives which allow for the use formulation in the single vial for multiple administrations. hGH solutions also could be filled in the cartridge which contain antimicrobial preservatives that allow for multiple administration of hGH. It is worth to mention that despite being multi-dose, these liquid formulations require once per day administration to achieve pharmacological effect. It will greatly benefit patients, especially children, if hGH could be formulated as sustained release product, e.g., a once per week injection product. It will greatly benefit patients also if multi-dose formulations of a once-weekly product were available on the market. Addition of antimicrobial preservatives is a known way of preparation of multi-dose pharmaceutical formulations.

Polyelectrolyte complexation with hGH crystal has been shown to be effective in vivo (e.g., administered through 29 G needle) to sustain the hGH release to 5-6 days, and stimulate the elevation of IGF-1 above baseline values for at least 7 days.

In these studies, performed to increase chemical stability of hGH formulations, crystalline hGH complexed to poly-Arginine was suspended in buffer solutions containing sodium citrate, or sodium phosphate buffers and also containing detergents, salts, and antimicrobial preservative.

Surprisingly, the addition of antimicrobial preservatives does not have adverse effects on crystallinity of hGH complexed to poly-Arginine; crystallinity was maintained in suspensions.

Interestingly, citrate buffer led to increases of free (soluble) hGH content in suspension of hGH crystals complexed to poly-Arginine—an indication of crystal dissolution in formulation which can lead to significant shortening of release profile. In contrast, the addition of phosphate buffer did not increase the content of free hGH in formulation and later in vivo animal studies confirmed equivalence to the release profile of a previously known formulation of complexed hGH.

Another part of experiment was to put hGH not complexed (bare crystals) to poly-Arginine into various buffer solutions. These crystals were readily soluble in said formulations. This experiment showed that bare hGH crystals could not maintain crystallinity in the multi-dose formulation vehicles studied here. By contrast, rhGH crystals complexed with polyarginine could be used for the purpose of multi-dose formulations using different antimicrobial preservatives.

This experiment was conducted to assess whether the addition of antimicrobial preservative phenol affects the content of free hGH in formulations. As a control, a previously known (control) formulation was studied. Three more samples were prepared by resuspending pellet of hGH crystals complexed with poly-Arginine into citrate buffer-based formulation vehicles with salt, with or without surfactant and phenol.

TABLE 26

Free hGH content in samples stored for 1 month at 5 ± 3° C.

| Lot# | Sample ID | Buffer Composition | C hGH supernatant, mg/mL | % of free hGH |
|---|---|---|---|---|
| 333-3-01 | Control complexed hGH | 25 mM Tris, 100 mM Na Acetate, 5% w/v PEG6000 pH 7.5 | 0 | 0 |
| 333-3-02 | Complexed hGH in phenol containing buffer | 10 mM Na Citrate, 0.2% Tween 20, 0.25% Phenol, 150 mM NaCl pH 6.0 | 1.6 | 6.4 |
| 333-3-07 | Complexed hGH in phenol containing buffer without surfactant | 10 mM Na Citrate, 0.25% Phenol, 150 mM NaCl pH 6.0 | 1.2 | 4.6 |
| 333-3-08 | Complexed hGH in similar buffer without phenol | 10 mM Na Citrate, 0.2% Tween 20, 150 mM NaCl pH 6.0 | 4.3 | 17.2 |

Results from this study showed that the addition of phenol does not have adverse effects on the content of free hGH both in a control formulation as well as to citrate buffer-based solutions containing surfactant and salt (Table 26). Surprisingly, the phenol-containing formulation showed a lower concentration of free hGH in suspension and the surfactant (Tween)-containing formulation showed a higher concentration of free hGH in suspension.

This experiment was performed to assess the influence of citrate and phosphate buffers on the content of free hGH in suspensions of hGH crystals complexed with poly-Arginine. As a control, a previously known hGH (control) formulation was used. Two more samples were prepared by resuspending pellet of hGH crystals complexed to poly-Arginine into citrate or phosphate buffer-based formulation vehicles containing also surfactant, salt and phenol.

TABLE 27

Free hGH content in samples stored for 1 month at 5 ± 3° C.

| Lot# | Sample ID | Buffer Composition | C hGH supernatant, mg/mL | % of free hGH |
|---|---|---|---|---|
| 333-3-01 | Control complexed hGH | 25 mM Tris, 100 mM Na Acetate, 5% w/v PEG6000 pH 7.5 | 0 | 0 |
| 333-3-02 | Complexed hGH in citrate based buffer | 10 mM Na Citrate, 0.2% Tween 20, 0.25% Phenol, 150 mM NaCl pH 6.0 | 1.6 | 6.4 |
| 333-3-05 | Complexed hGH in phosphate based buffer | 10 mM Na Phosphate, 0.2% Tween 20, 0.25% Phenol, 150 mM NaCl pH 6.0 | 0.2 | 0.6 |

Results from this experiment showed that control formulation has a very minor content of free (soluble) hGH, indicating the integrity of hGH crystals complexed with poly-Arginine (Table 27). Surprisingly, the content of free (soluble) hGH was higher when hGH crystals complexed with poly-Arginine were transferred in citrate-based buffer, indicating partial dissolution of hGH crystals. This crystals dissolution can lead to significant shortening of in vivo hGH release profile. In contrast, when hGH crystals complexed were transferred into phosphate-based buffer, the content of free (soluble) hGH was an order of magnitude lower than in citrate-based buffer. Thus, use of phosphate-based buffers as formulation vehicles for hGH crystals complexed with poly-Arginine could provide an advantage in terms of maintaining once-weekly release profiles seen with the control formulation.

Multi-dose formulations that would maintain crystallinity of hGH crystals complexed with poly-Arginine in suspension preferably contain phosphate buffer, phenol as a preservative, and a tonicity modifying component.

An experiment was undertaken to demonstrate influence of citrate and phosphate buffers on content of free hGH in suspensions of hGH crystals not complexed with poly-Arginine (i.e., bare hGH crystals). As control, the base formulation vehicle from the previous (control) complexed hGH formulation was used. Two more samples were prepared by resuspending pellet of bare crystals into citrate or phosphate buffer-based formulation vehicles containing also surfactant, salt, and phenol.

TABLE 28

Free hGH content in samples stored for 1 month at 5 ± 3° C.

| Lot# | Sample ID | Buffer Composition | C hGH supernatant, mg/mL | % of free hGH |
|---|---|---|---|---|
| 249-54-02 | control | 25 mM Tris, 100 mM Na Acetate, 5% w/v PEG6000 pH 7.5 | 0 | 0 |
| 333-48-05 | Bare hGH crystals in base control formulation vehicle | 25 mM Tris, 100 mM Na Acetate, 5% w/v PEG6000 pH 7.5 | 9 | 35 |
| 333-48-07 | Bare hGH crystals in citrate based buffer | 10 mM Na Citrate, 0.2% Tween 20, 0.25% Phenol, 150 mM NaCl pH 6.0 | 27 | 100 |
| 333-48-08 | Bare hGH crystals in phosphate based buffer | 10 mM Na Phosphate, 0.2% Tween 20, 0.25% Phenol, 150 mM NaCl pH 6.0 | 27 | 100 |

Results from this experiment showed that base control formulation vehicle allows partial dissolution of bare hGH crystals (Table 28). Surprisingly, bare hGH crystals were readily soluble in citrate or phosphate-based buffers that also contained surfactant, salt and preservative. Dissolution of crystals in formulation can lead to significant shortening of in vivo hGH release profile.

The next experiment was performed to demonstrate the influence different preservatives at different concentrations on the content of free hGH and poly-Arginine in suspensions of hGH crystals complexed with poly-Arginine in the control formulation vehicle or in sodium phosphate low pH formulation vehicles. As a control, formulation vehicles without the addition of preservatives were used. The content of free hGH and poly-Arginine in the supernatants of samples was analyzed after one month incubation at room temperature.

TABLE 29

Free hGH content in samples stored for 1 month at room temperature in low pH sodium phosphate based buffer

| Lot# | Formulation vehicle composition | C hGH supernatant, mg/mL | % of free hGH | C poly-Arginine supernatant, mg/mL | % of free poly-Arginine |
|---|---|---|---|---|---|
| 333-52-01 | Control low pH FV —10 mM NaHPO4, 100 mM NaCl, 5% PEG6000, pH 6.0 | 0.0043 | 0.02 | 0.1097 | 3.05 |
| 333-52-02 | 0.5% phenol in control low pH FV | 0.0081 | 0.04 | 0.2304 | 6.40 |
| 333-52-03 | 0.2% phenol in control low pH FV | 0.0266 | 0.12 | 0.1813 | 5.04 |
| 333-52-04 | 0.1% phenol in control low pH FV | 0.0248 | 0.11 | 0.1047 | 2.91 |
| 333-52-05 | 1.5% benzyl alcohol in control low pH FV | 0.0184 | 0.08 | 0.2336 | 6.49 |
| 333-52-06 | 0.75% benzyl alcohol in control low pH FV | 0.0248 | 0.11 | 0.2352 | 6.53 |
| 333-52-07 | 0.1% benzyl alcohol in control low pH FV | 0.0183 | 0.08 | 0.1848 | 5.13 |
| 333-52-08 | 0.1% methyl paraben in control low pH FV | 0.0145 | 0.06 | 0.1222 | 3.39 |
| 333-52-09 | 0.05% methyl paraben in control FV | 0.0325 | 0.14 | 0.0743 | 2.06 |
| 333-52-10 | 0.02% methyl paraben in control low pH FV | 0.0367 | 0.16 | 0.0498 | 1.38 |
| 333-52-11 | 0.3% m-cresol in control low pH FV | 0.0097 | 0.04 | 0.1138 | 3.16 |
| 333-52-12 | 0.2% m-cresol in control low pH FV | 0.0057 | 0.03 | 0.1007 | 2.80 |
| 333-52-13 | 0.1% m-cresol in control low pH FV | 0.0114 | 0.05 | 0.1086 | 3.02 |
| 333-52-14 | 0.5% clorobutanol in control low pH FV | 0.0132 | 0.06 | 0.1919 | 5.33 |
| 333-52-15 | 0.3% clorobutanol in control low pH FV | 0.0211 | 0.09 | 0.1302 | 3.62 |
| 333-52-16 | 0.1% clorobutanol in control low pH FV | 0.0331 | 0.15 | 0.1187 | 3.30 |

TABLE 30

Free hGH content in samples stored for 1 month at room temperature in control formulation vehicle

| Lot# | Formulation vehicle composition | C hGH supernatant, mg/mL | % of free hGH | C poly-Arginine supernatant, mg/mL | % of free poly-Arginine |
|---|---|---|---|---|---|
| 333-52-22 | Control vehicle- 25 mM Tris, 100 mM Na Acetate, 5% w/v PEG 6000, pH 7.5 | 0.0038 | 0.02 | 0.1147 | 3.19 |
| 333-52-17 | 0.5% phenol in control vehicle | 0.0026 | 0.01 | 0.3223 | 8.95 |
| 333-52-18 | 1.5% benzyl alcohol in control vehicle | 0.0085 | 0.04 | 0.3343 | 9.29 |
| 333-52-19 | 0.1% methyl paraben in control vehicle | 0.0051 | 0.02 | 0.1186 | 3.30 |
| 333-52-20 | 0.3% m-cresol in control vehicle | 0.0023 | 0.01 | 0.1562 | 4.34 |
| 333-52-21 | 0.5% clorobutanol in control vehicle | 0.0036 | 0.02 | 0.3169 | 8.80 |

Results from this experiment showed that addition of antimicrobial preservatives does not significantly change the amount of free hGH and poly-Arginine in suspensions of hGH crystals complexed with poly-Arginine in 10 mM $NaHPO_4$, 100 mM NaCl, 5% PEG6000, pH 6.0 formulation vehicle (Tables 29 and 30). In the examples where 1.5% benzyl alcohol and 0.5% clorobutanol were added to the control formulation vehicle, an increase in the amount of free poly-Arginine in supernatants was observed. The increase of free poly-Arginine however did not cause an increase of free hGH concentrations.

This experiment was performed to demonstrate the influence of different preservatives at different concentrations on chemical stability of hGH in suspensions of hGH crystals complexed with poly-Arginine in the control formulation vehicle and in sodium phosphate low pH formulation vehicle. As a control, control and sodium phosphate low pH formulation vehicles without addition of preservatives were used. Increases in content of hGH degradation products were analyzed after one month incubation at room temperature.

TABLE 31

Accumulation of hGH degradation products in samples stored for 1 month at room temperature in low pH sodium phosphate based buffer

| Lot# | Buffer Composition | Increase in hGH impurities, according to RP-HPLC % | Increase in hGH impurities, according to IEX-HPLC % |
|---|---|---|---|
| 333-52-01 | Control low pH FV - 10 mM NaHPO4, 100 mM NaCl, 5% PEG6000, pH 6.0 | 4.48 | 7.94 |
| 333-52-02 | 0.5% phenol in control low pH FV | 3.76 | 4.16 |
| 333-52-03 | 0.2% phenol in control low pH FV | 4.08 | 3.35 |
| 333-52-04 | 0.1% phenol in control low pH FV | 4.15 | 4.69 |
| 333-52-05 | 1.5% benzyl alcohol in control low pH FV | 5.23 | 2.37 |
| 333-52-06 | 0.75% benzyl alcohol in control low pH FV | 5.06 | 3.45 |
| 333-52-07 | 0.1% benzyl alcohol in control low pH FV | 6.95 | 4.34 |
| 333-52-08 | 0.1% methyl paraben in control low pH FV | 5.30 | 3.85 |
| 333-52-09 | 0.05% methyl paraben in control FV | 3.95 | 4.47 |
| 333-52-10 | 0.02% methyl paraben in control low pH FV | 5.14 | 5.10 |
| 333-52-11 | 0.3% m-cresol in control low pH FV | 10.09 | 1.89 |
| 333-52-12 | 0.2% m-cresol in control low pH FV | 5.14 | 1.84 |
| 333-52-13 | 0.1% m-cresol in control low pH FV | 4.53 | 4.04 |
| 333-52-14 | 0.5% clorobutanol in control low pH FV | 9.16 | 1.55 |
| 333-52-15 | 0.3% clorobutanol in control low pH FV | 7.36 | 1.97 |
| 333-52-16 | 0.1% clorobutanol in control low pH FV | 5.14 | 6.08 |

TABLE 32

Accumulation of hGH degradation products in samples stored for 1 month at room temperature in control formulation vehicle

| Lot# | Buffer Composition | Increase in hGH impurities, according to RP-HPLC % | Increase in hGH impurities, according to IEX-HPLC % |
|---|---|---|---|
| 333-52-22 | Control vehicle 25 mM Tris, 100 mM Na Acetate, 5% w/v PEG 6000, pH 7.5 | 4.66 | 9.09 |
| 333-52-17 | 0.5% phenol in control vehicle | 5.96 | 7.91 |
| 333-52-18 | 1.5% benzyl alcohol in control vehicle | 4.70 | 6.55 |
| 333-52-19 | 0.1% methyl paraben in control vehicle | 5.10 | 8.41 |
| 333-52-20 | 0.3% m-cresol in control vehicle | 7.47 | 7.30 |
| 333-52-21 | 0.5% clorobutanol in control vehicle | 20.78 | 4.82 |

Surprisingly, the addition of antimicrobial preservatives can increase chemical stability of hGH in suspensions of hGH crystals complexed with poly-Arginine in 10 mM NaHPO$_4$, 100 mM NaCl, 5% PEG6000, pH 6.0 formulation vehicle (Tables 31 and 32). This improvement was not as pronounced in the case of clorobutanol. Also, the addition of 0.5% of clorobutanol to base ALTU-238 formulations decreased chemical stability of hGH. Thus, clorobutanol is not a preferred antimicrobial preservative for use with formulations containing complexed hGH.

This experiment was performed to assess the influence of antimicrobial preservatives on the morphology of hGH crystals complexed with poly-Arginine in different formulation vehicles. As a control, control and sodium phosphate low pH formulation vehicles without addition of preservatives were used. Microscopic observation performed after one month incubation at room temperature. Microscopic appearance of hGH crystals coated with poly-Arginine in suspensions of control formulation vehicle without antimicrobial preservatives, with % 0.5 of Phenol, and with 0.3% of meta-cresol (right) was examined. Microscopic appearance of hGH crystals coated with poly-Arginine in suspensions of low pH phosphate based formulation vehicle (10 mM NaHPO4, 100 mM NaCl, 5% PEG6000, pH 6.0) without antimicrobial preservatives and with 0.2% of phenol and with 0.2% of meta-cresol was also examined.

Surprisngly, the addition of antimicrobial preservatives had no adverse influence on morphology of hGH crystals complexed with poly-Arginine.

In Vivo Results: Hypophysectomized Rat Study

This experiment was performed to assess whether the release profile of poly-Arginine complexed hGH crystals in multi-dose formulation vehicles (with preservative) is equivalent to hGH release profile of single-dose control hGH formulation. No significant difference in the pharmacodynamic profile was observed between a single-dose formulation of complexed hGH in control buffer without preservative and a multi-dose formulation complexed hGH in control buffer with phenol in hypophysectomized male Wistar rats.

The efficacy confirmation in the standard rat weight gain assay is an important step for the clinical and commercial development of an hGH formulation. Test or control material was administered to hypophysectomized male Wistar rats (9 rats/group) by SC injection. The study compared the growth of hypophysectomized rats after receiving a single SC injection of 5.6 mg/kg of single-dose and multi-dose (with preservative) hGH formulation in control buffers or daily SC injections of 0.8 mg/kg of soluble commercial rhGH (Nutropin AQ) for 7 days (i.e., 5.6 mg/kg/week). Body weights were measured weekly prior the start of dosing and daily from Day −7 (seven days prior dosing) until the end of observation period on day 8. No significant difference in body weight gains were observed between the daily rhGH control, single-dose and multi-dose formulations in this hypophysectomized rat model; mean body weight changes were 18±3%, 18±2%, and 16±4%, respectively.

In Vivo Results: Hypophysectomized Rat Study

This experiment was performed to assess whether the release profile of poly-Arginine complexed hGH crystals in multi-dose formulation vehicles (with preservative) is equivalent to hGH release profile of single-dose control hGH formulation. No significant difference in the PD profile was observed between a single-dose formulation of complexed hGH in control buffer without preservative and a multi-dose formulation complexed hGH in control buffer with phenol in hypophysectomized male Wistar rats. Test or control material was administered to hypophysectomized male Wistar rats (9 rats/group) by SC injection. The study compared the growth of hypophysectomized rats after receiving a single SC injection of 5.6 mg/kg of single-dose and multi-dose formulations. Body weights were measured weekly prior the start of dosing and daily from Day −7 (seven days prior dosing) until the end of observation period on day 8. No significant difference in body weight gains were observed between the single-dose and multi-dose formulations in this hypophysectomized rat model; mean body weight changes were 15±2% and 16±1% (mean±SE), respectively.

Preparations of said formulations: Protocol:

(1) Production of poly-Arginine complexed hGH crystal, 25 mg/ml (Govardhan et al., 2004-WO 2004/060310)

(2) Centrifugation of step 1 product, 3,5000 rpm, 15 min, 4° C.

(3) Remove supernatant, record volume.

(4) Add same volume multi-dose formulation vehicle.

(5) Resuspend the pellet.

(6) Repeat step 3, then add volume of formulation vehicle to get desired hGH concentration upon resuspension and resuspend.

(7) Store the final suspension at 2-8° C.

Analytical Methods

RP-HPLC is used to detect all hGH related impurities but deamidated hGH (Deamidation is determined with use of IEX-HPLC, see below) performed on C5 Supelco Discovery Bio Wide Pore Column, 5 cm×4.6 mm, 3 um particle size, 30 nm Pore size. Thermostat temperature is 37° C. The elution is carried out with a gradient system present by mobile phase A (0.1% TFA in H$_2$O) and mobile phase B (0.1% TFA in MeCN). Gradient system changed from 5% B to 50% B from 0-2.5 min., then 50% to 70% B in 2.5-15.5 min. then, 70% to 90% in 1.5 min., immediately following this 5% B is re-established. A 3 min post-time is held before the start of the next run. Flow rate is 1.0 ml/min. Injection volume is 10 µl for hGH sample at 2 mg/ml concentration. Detection performed at 214 nm. Percent purity is calculated based on peak area.

IEX-HPLC is used as deamidation specific assay. To determine the purity of hGH using the a PolyLC (NEST Group cat #P054SE0503) is used. The column thermostat temperature is set to 30° C. 20 µL of sample at 2 mg/mL concentration injected. The elution is carried out at a flow rate of 1 mL/min with a gradient system present by mobile phase A (50 mM Na Acetate, pH 4.6) and mobile phase B (50 mM Na Acetate, pH 4.6 250 mM NaCl). The gradient system is changed from 0% B to 20% B from 0 to 5 min., then 20% to 70% B in 5 to 25 min. then, 70% to 100% in 25 to 25.1 min. 100% B is kept until 27 min. following 27.1 min, 0% B is re-established for a 5 min. post-time. Detection is performed at 280 nm. Percent purity is calculated based on peak area.

Example 4

These experiments relate to the field of crystalline suspensions of therapeutic proteins for use with needle free (jet)

injectors for administration. Different devices are utilized for administering liquid soluble formulations of pharmaceuticals including needle free (jet) injector devices. These devices help to increase patient compliance by improving ease of drug administration; decreasing injection time and possibly reducing pain upon injection.

Crystalline protein formulations may have advantage over soluble formulations. Needle-free options could increase patient compliance when using crystalline drugs even more. However, needle free delivery options for crystalline insulin suspension are not available. Needle phobia is reported in about 5-10% of patient population. It would be beneficial for patients to have multiple delivery capabilities for administration of crystalline parenteral formulations, including needle-free option.

Another possible application of jet injectors in conjunction with crystalline protein formulation is in the veterinary market. Use of crystalline formulations, e.g., in combination with jet injectors, can provide extended drug release to improve animal care compliance, e.g., as a result of decreased frequency of administrations and shorter time required for injection and decreased pain upon injection.

Needle-free injectors are in use for administration of liquid therapeutic protein formulations. A possible reason for absence of reported cases of needle-free device for crystalline protein is that protein crystals represent particulates in suspension, which could make injection via needle-free device impossible or which could bring physical changes to crystalline formulation undermining therapeutic action of said formulation.

The standard approach of administration of soluble and crystalline therapeutic parenteral formulations is use of hypodermic needs. Pain upon injection is associated with size of the needle and time needle is held at the injection site of the patient. Larger needle gauge and increased time of injection is associated with increased pain at the injection site caused by the needle. Since jet injectors have comparatively small orifice size (Table 2) and injection time is very short, pain upon injection is significantly less compared to the needle injection systems. Use of needle free (jet) injectors impose additional requirement on formulations.

Herein, the influence of needle-free injectors on crystalline protein suspension formulation with needle injection systems was compared. BD needles of 30 to 18 gauges were used as comparators in the study. Needle G30 was regular wall and G25, 21 and 18 needles were thin-wall. Comparison of needle inner and outer diameters represent in Table 2.

A BioJector needle-free (jet) injection system was used to study the feasibility of using jet injectors with crystalline protein formulations.

BioJector 2000: The B-2000 consists of two components: a hand-held, reusable jet injector and a sterile, single-use, disposable plastic syringe. The BioJector 2000 injector uses a disposable carbon dioxide cartridges as a power source. The carbon dioxide gas provides consistent, reliable pressure on the plunger of the disposable syringe, thereby propelling the medication into the tissue.

The second component of the system, the BioJector single-use disposable syringe consists of a plastic, needle-free, variable dose syringe. The body of the syringe is transparent and has graduated markings to aid accurate filling. There are five different BioJector syringes, each of which is intended for a different injection depth or body type.

VetJet and Vitajet: The VetJet is a modified Vitajet for use in the veterinary market. VetJet is also composed of two components, a portable injector unit and a disposable syringe. VetJet is powered by a spring.

The capability of crystalline suspensions to be administered using needle-free jet injectors was explored. Limitations on crystalline suspension that can be used in needle-free injectors were identified. However, crystalline formulations that are appropriately formulated and selected can be administered using needle-free (jet) injection systems.

In order to study the feasibility of using crystalline protein formulations with needle free injector, suspensions of hGH crystals coated with poly-Arginine is buffer solution containing 25 mg/mL rhGH, 5 mg/mL poly-Arg, 25 mM Tris, 100 mM Na Acetate, 5% w/v PEG 6000 pH 7.5—ALTU-238—as well as similar formulation containing 0.2% of hyaluronic acid (HA)—HA-ALTU-238—were used. We also compared influence of injection using needle-free and needle-based systems on a soluble commercial hGH formulation (see Table 33).

TABLE 33

Soluble and crystalline hGH samples

| Lot # | Concentration | Description |
|---|---|---|
| 249-67-05 | 5 mg/mL | Commercial soluble hGH formulation Nutropin AQ[1] |
| 249-67-06 | 25 mg/mL | ALTU-238 Phase I formulation |
| 249-70-04 | 25 mg/mL | Reduced size ALTU-238 |
| 249-81-01 | 25 mg/mL | HA-ALTU-238 |

[1]Manufactured and commercialized in the US by Genentech Inc., South San Francisco, CA.

Properties of crystalline suspensions of model proteins with different crystal size and different protein concentrations (see Table 34) when injected using needle-free as well as needle based injection systems were also explored.

TABLE 34

Crystalline protein suspension formulations sample description

| Lot # | Concentration | Description | Particle size |
|---|---|---|---|
| 249-82-01 | 30 mg/mL | BC-Lipase small size hexagonal crystals Lot #145-75-2 | 16 (20 μm at largest dimension) |
| 249-83-01 | 30 mg/mL | BC-Lipase medium size hexagonal crystals LP-7 | 30 (45 μm at largest dimension) |
| 249-84-01 | 30 mg/mL | BC-Lipase big size rhomboidal crystals Lot L-00298-K | 32 (70 × 40 × 15 μm) |
| 249-85-01 | 40 mg/mL | Glutaryl Alcalase big size elongated bipiramidal crystals | 42 μm (150 × 30 × 30) |

For all the samples viscosities of formulation vehicles were comparable to the viscosity of water.

This experiment was performed to study the effects of different injection systems on aggregation and chemical purity of hGH in crystalline ALTU-238 suspension. Injections were performed in triplicate. After injection, crystals were dissolved and soluble hGH was analyzed with respect to aggregation, as analyzed by SE-HPLC, and chemical degradation, as analyzed by RP-HPLC and deamidation specific IEX-HPLC.

TABLE 35

Aggregation and chemical purity of hGH in ALTU-238 after injection with different injection systems

| Sample | SE-HPLC, % | RP-HPLC, % | IEX-HPLC, % |
|---|---|---|---|
| ALTU-238 Lot# 249-67-06 before injection | 99.51 | 90.72 | 84.44 |
| 249-67-06 after BD syringe with 30G × ½" preattached needle | 99.10 | 91.42 | 84.85 |
| 249-67-06 after BioJector 2000 injector | 99.48 | 91.03 | 83.54 |
| 249-67-06 after VetJet injector | 99.32 | 91.86 | 84.22 |

There was no significant difference in the content of monomer or hGH related substances in the control sample and test samples injected with the use of 30 G×½" needle, BioJector 2000 or VetJet injection systems (Table 35). These data support the conclusion that there was no measured impact of shear at the molecular level as a result of using any of the tested injection systems.

In order to study possible influence of shear stress on crystalline hGH suspensions, samples prior and after injections were analyzed for content of free hGH and poly-Arginine in the supernatants of crystalline hGH suspensions. The control suspension, ALTU-238, is a previously known suspension of coated or complexed hGH crystals with poly-Arginine in a formulation vehicle. Shear stress could change release properties of said formulation. ALTU-238 contains a typical range of free hGH and poly-Arginine. Changes of these parameters could indicate adverse influence of said injection systems on crystals in suspensions and could affect hGH release profile. Injections were performed in triplicate. Supernatants of the control sample as well as the samples after using different injection systems were analyzed for content of hGH and poly-Arginine. The average content for the three runs of free hGH and poly-Arginine is listed in the Table 36.

TABLE 36 hGH and poly-Arginine content in the supernatants of ALTU-238 samples

| Sample | C hGH sup | C p-R sup |
|---|---|---|
| ALTU-238 Lot # 249-67-06 | 0.039 | 0.264 |
| 249-67-06 after BD syringe with 30G × ½" preattached needle | 0.003 | 0.171 |
| 249-67-06 after BioJector 2000 injector | 0.003 | 0.163 |
| 249-67-06 after VetJet injector | 0.023 | 0.219 |

No increase in the content of free hGH or poly-Arginine as result of using 30 G×½" needle, BioJector 2000 or VetJet injection systems was observed. These data suggest that the studied injection systems do not adversely influence the crystalline hGH suspension.

To study influence of different injection systems on the dissolution profile of complexed hGH crystal formulations, an ALTU-238 control sample and ALTU-238 samples after injection were analyzed for dissolution in a 3-pH dissolution test. Injections were performed in duplicate. The average of two runs is presented in Table 37.

TABLE 37

3-pH dissolution, average of 2 runs

| Sample | Dissolution at pH 2.5 (%) | Dissolution at pH 5.0 (%) | Dissolution at pH 7.0 (%) |
|---|---|---|---|
| ALTU-238 Lot # 249-67-06 - control | 110.00 | 63.30 | 24.17 |
| 249-67-06 after BD syringe with 30G × ½" preattached needle | 101.39 | 69.66 | 25.87 |
| 249-67-06 after BioJector 2000 injector | 101.64 | 65.83 | 25.22 |
| 249-67-06 after VetJet injector | 105.73 | 67.05 | 25.17 |

No significant differences in hGH dissolution were seen among the control sample and samples injected with the 30 G×½" needle, BioJector 2000, or VetJet injection systems (Table 37). These data support the feasibility of using needle-free (jet) injectors for administration of ALTU-238.

An experiment was conducted to show the effect of different injection systems on particle surface charge. Zeta potential in ALTU-238 samples was studied after injection with a BioJector 2000 injector. After the first injection, the sample was collected and injected repeatedly.

TABLE 38

Zeta potential of ALTU-238 samples prior injection, after first and second injection with BioJector 2000 system

| Sample | ξ-potential, mV |
|---|---|
| ALTU-238 Lot # 249-9-02 prior to injection | 21.8 ± 0.8 |
| 249-70-05 = 249-9-02 after $1^{st}$ injection with BioJector 2000 | 22.7 ± 1.5 |
| 249-70-06 = 249-9-02 after $2^{nd}$ injection with BioJector 2000 | 22.6 ± 0.5 |

There were no significant changes in particle surface charge after the first and repeated injections with BioJector 2000 compared to the original sample prior to injection (Table 38). Injection with BioJector 2000 does not change a-potential in ALTU-238 formulations.

In this experiment, the influence of BioJector 2000 jet injections on particle size of crystalline hGH suspension—ALTU-238—was examined. Particle size was measured using a Coulter LS 230 particle sizer prior to injection, and after the first and repeated injections. A Fraunhofer optical model was used to analyze data. Microscopic observation was used to detect possible changes in crystal morphology.

TABLE 39

Particle size distribution in ALTU-238 samples

| Sample | Size μm % < 10 | Size μm % < 50 | Size μm % < 90 |
|---|---|---|---|
| 249-70-04 = 249-9-02 prior injection | 1.57 | 3.50 | 6.61 |
| 249-70-05 = 249-9-02 after $1^{st}$ injection with BioJector 2000 | 1.61 | 3.31 | 6.02 |
| 249-70-06 = 249-9-02 after $2^{nd}$ injection with BioJector 2000 | 1.71 | 3.42 | 6.01 |

Figure 9:
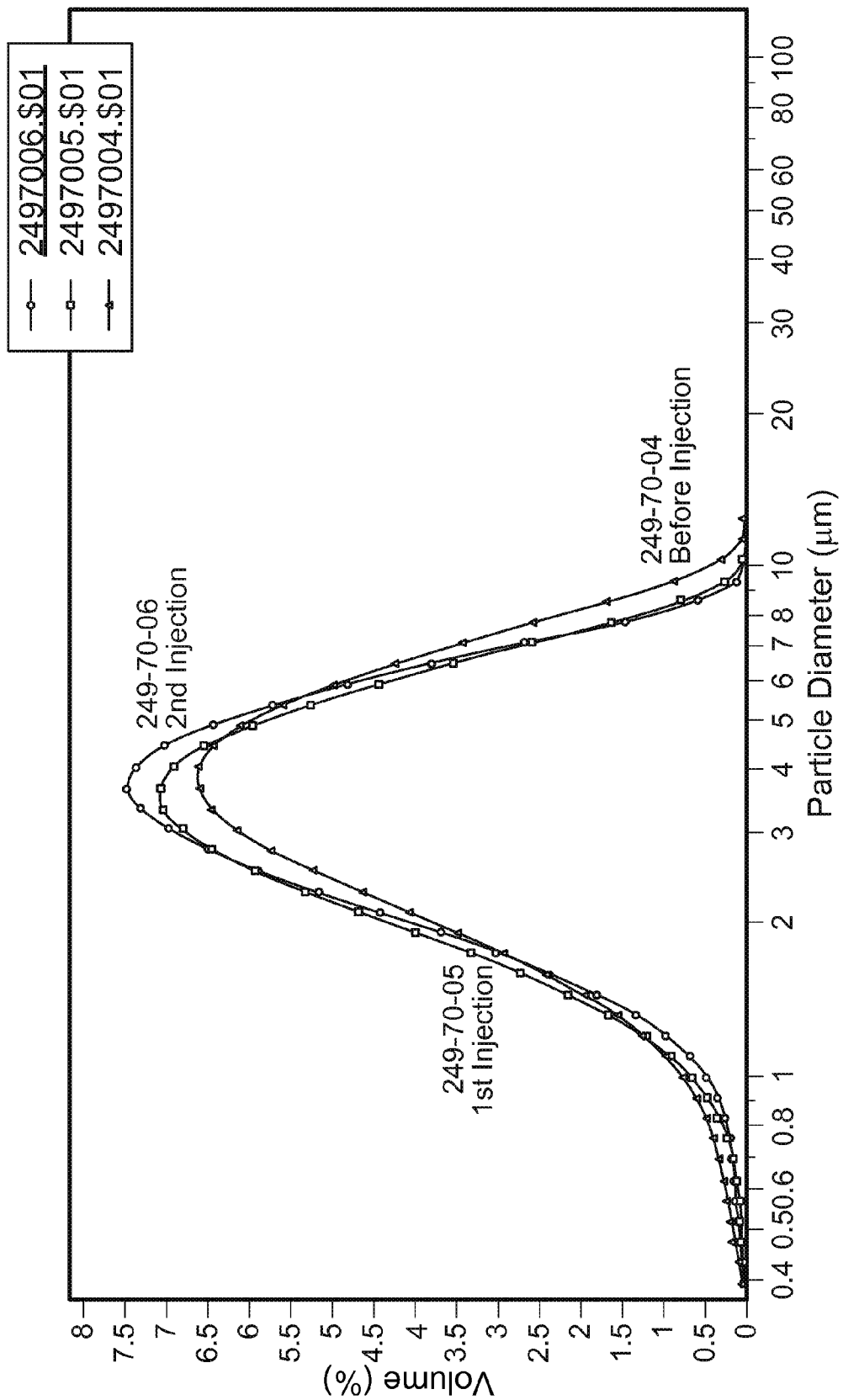
FIG. 9 is a graph showing the overlay of particle size distribution in an ALTU-238 sample originally free of crystalline aggregates, after first, and after second injections with a BioJector 2000 injection system.

No significant change in particle size after the first and repeated injections with BioJector 2000 compared to original sample prior to injection (Table 39; FIG. 9). These numbers are consistent with microscopic observation. No reduction in particle size or changes in crystal morphology were observed after injection of ALTU-238 with any of injection systems. Similarly, no changes were observed after repeated injections.

A suspension of hGH crystals coated with poly-Arginine in a formulation vehicle containing hyaluronic acid, HA-ALTU-238, was used to study feasibility of using jet injectors with this crystalline protein suspension formulations. In this experiment, the influence of different injection systems on hGH aggregation was examined. Injections were performed in duplicate. After injection, crystals were dissolved and soluble hGH was analyzed for aggregation by SE-HPLC.

TABLE 40

Monomer protein content

| Sample | SE-HPLC, % |
| --- | --- |
| 249-75-01 (HA-ALTU-238) | 99.83 |
| 249-75-01 after BD syringe with 30G × ½" preattached needle | 99.83 |
| 249-75-01 after BioJector 2000 injector | 99.61 |
| 249-75-01 after VetJet injector | 99.83 |

There was no significant difference in monomer hGH content in the control HA-ALTU-238 sample and samples injected with the use the 30 G×1/2" needle, BioJector 2000, or VetJet injection systems (Table 40). These data support the conclusion that there was no measured impact of shear at the molecular level as a result of using any of the tested injection systems.

In this experiment, the influence of the BioJector 2000 jet injection on particle size of a crystalline hGH suspension—HA-ALTU-238. Particle size was measured using a Coulter LS 230 particle sizer prior injection, and after first and repeated injections. A Fraunhofer optical model was used to analyze data. Microscopic observation was used to detect possible changes in crystal morphology.

TABLE 41

Particle size distribution in HA-ALTU-238 sample

| Sample | Size μm % < 10 | Size μm % < 50 | Size μm % < 90 |
| --- | --- | --- | --- |
| 249-81-01 = HA-ALTU-238 prior to injection | 2.28 | 4.87 | 8.96 |
| 249-81-02 = 249-81-01 after $1^{st}$ injection with BioJector 2000 | 2.27 | 4.59 | 8.29 |
| 249-81-03 = 249-81-01 after $2^{nd}$ injection with BioJector 2000 | 1.96 | 4.05 | 7.23 |
| 249-81-04 = 249-81-01 after $1^{st}$ injection with VetJet | 1.97 | 4.23 | 7.70 |
| 249-81-05 = 249-81-01 after $2^{nd}$ injection with VetJet | 1.89 | 4.21 | 8.30 |
| 249-81-06 = 249-81-01 after $1^{st}$ injection through 30G × ½" needle | 1.85 | 4.12 | 7.59 |
| 249-81-07 = 249-81-01 after $2^{nd}$ injection through 30G × ½" needle | 1.91 | 4.05 | 7.45 |

Figure 10:
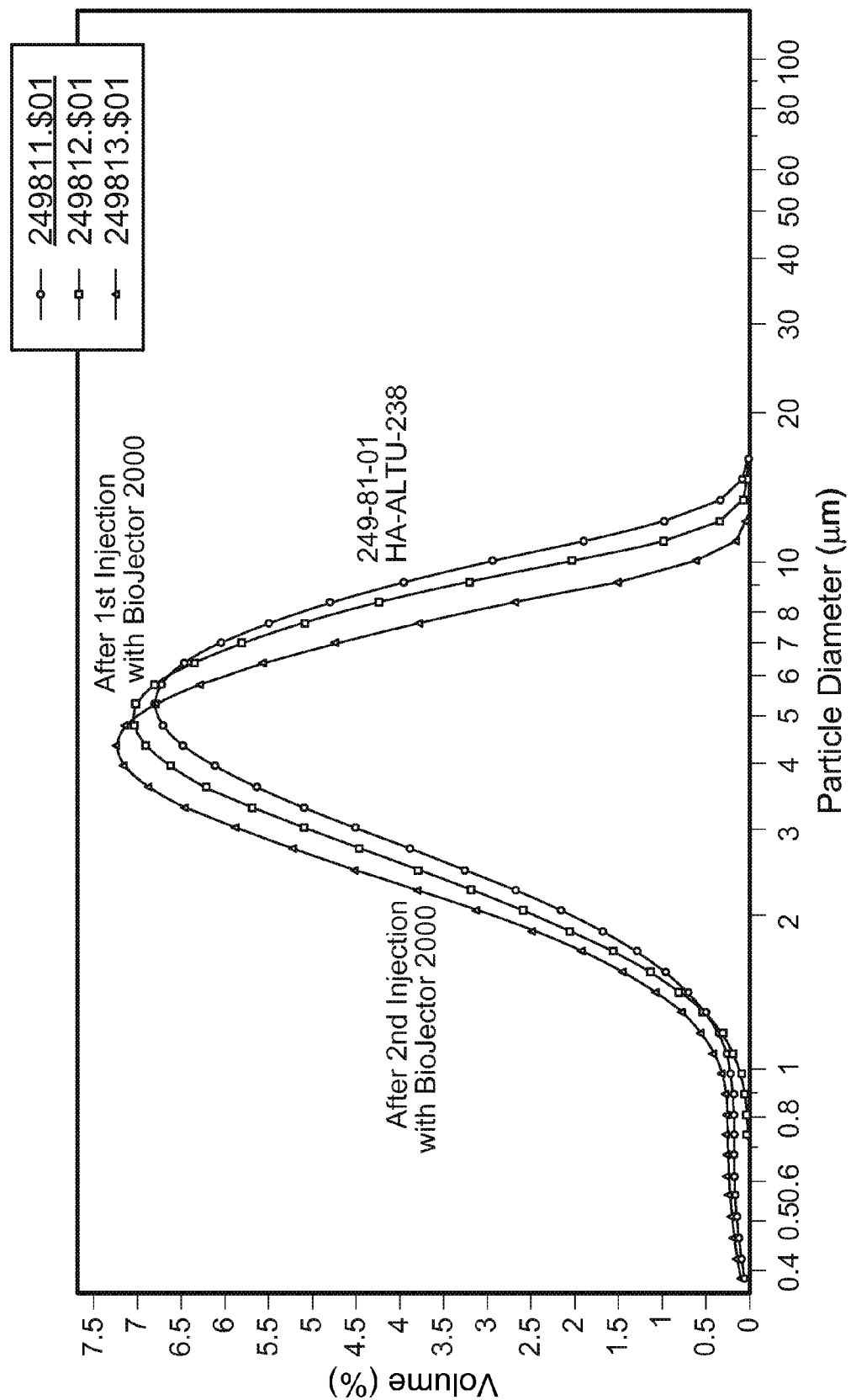
FIG. 10 is a graph showing the overlay of particle size distribution in HA-ALTU-238 sample prior to injection, after first, and after second injections with BioJector 2000 injection system.
Figure 11A:
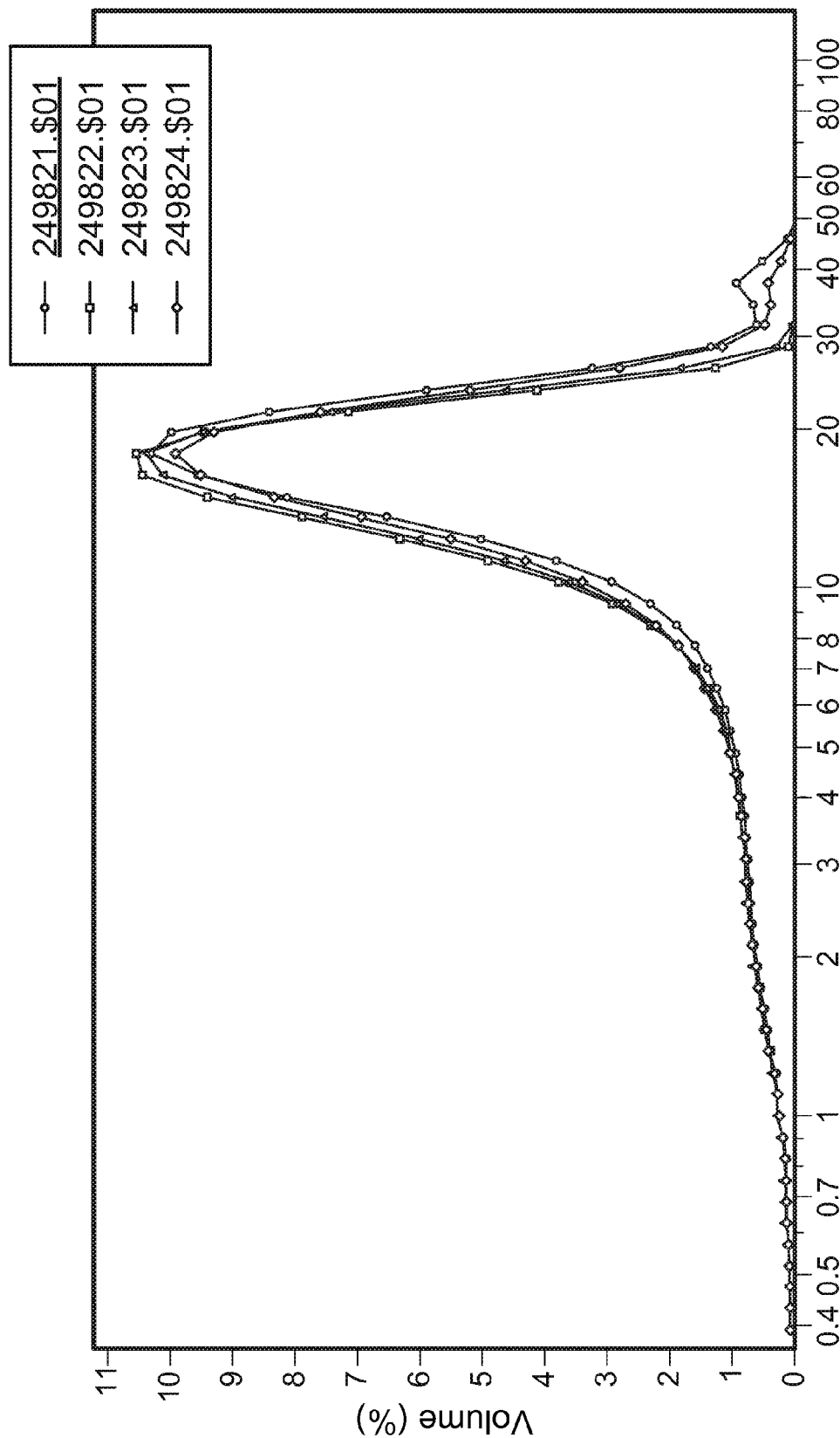
FIGS. 11A and B are graphs showing the overlay of volume—(A) and number—(B) based particle size distribution of BC-Lipase (20 μm) samples before injection and after injections through BD syringe with preattached 30 G×½" needle, BioJector 2000, and VetJet systems.
Figure 11B:
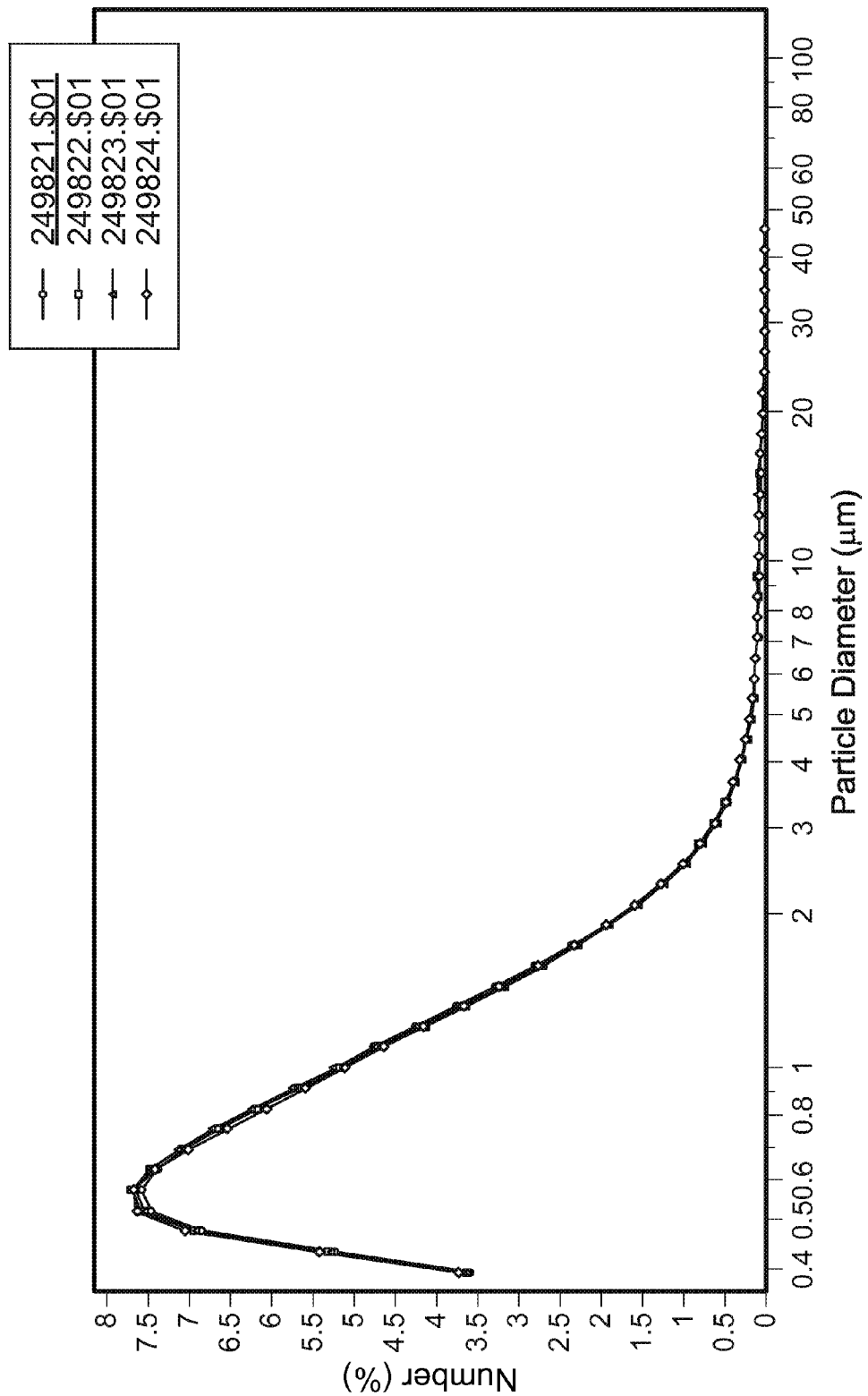
Figure 12A:
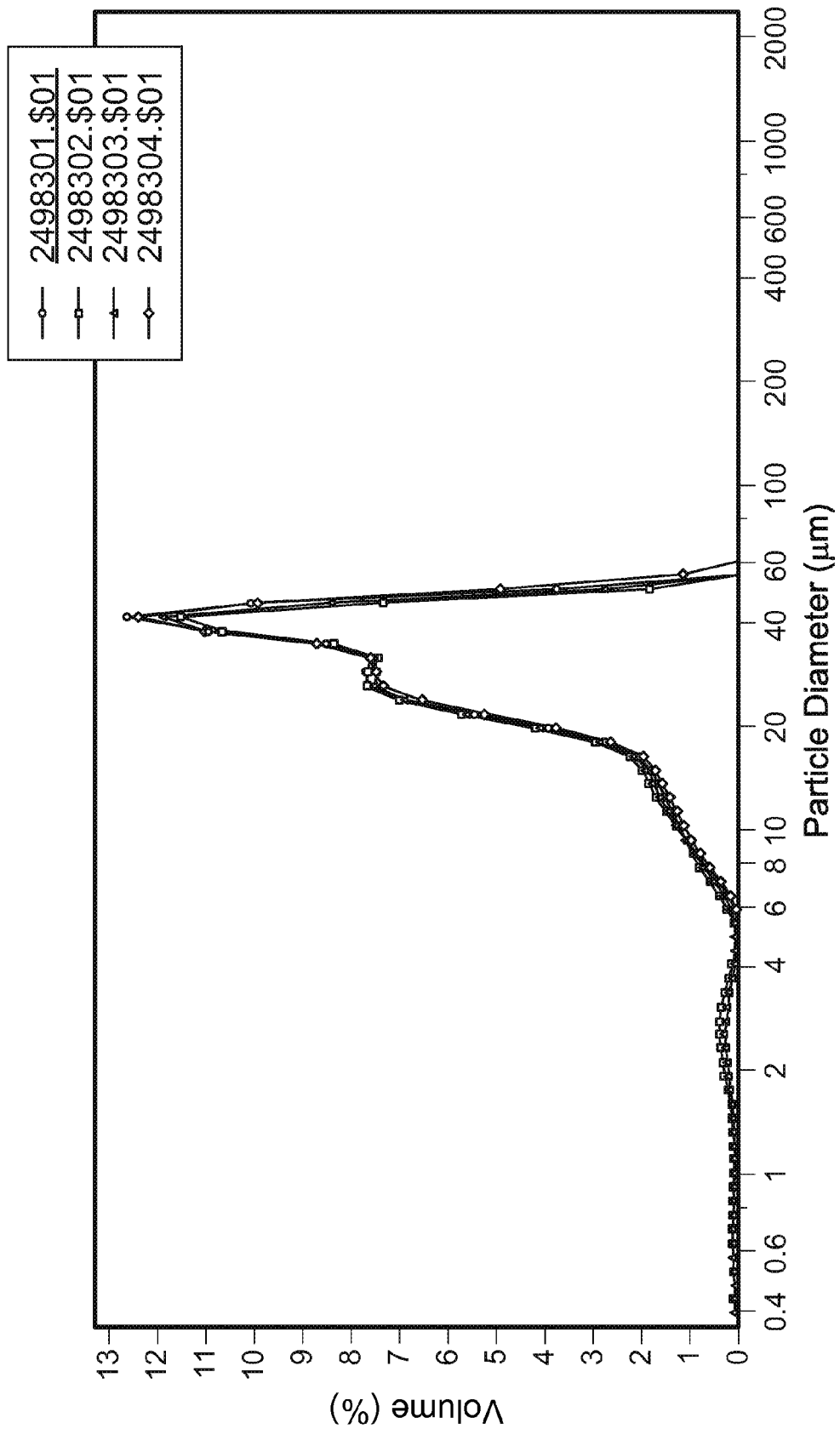
FIGS. 12A and B are graphs showing the overlay of volume—(A) and number—(B) based particle size distribution of BC-Lipase (30 μm) samples before injection, and after injections through BD syringe with preattached 30 G×½" needle, BioJector 2000 and VetJet systems.
Figure 12B:
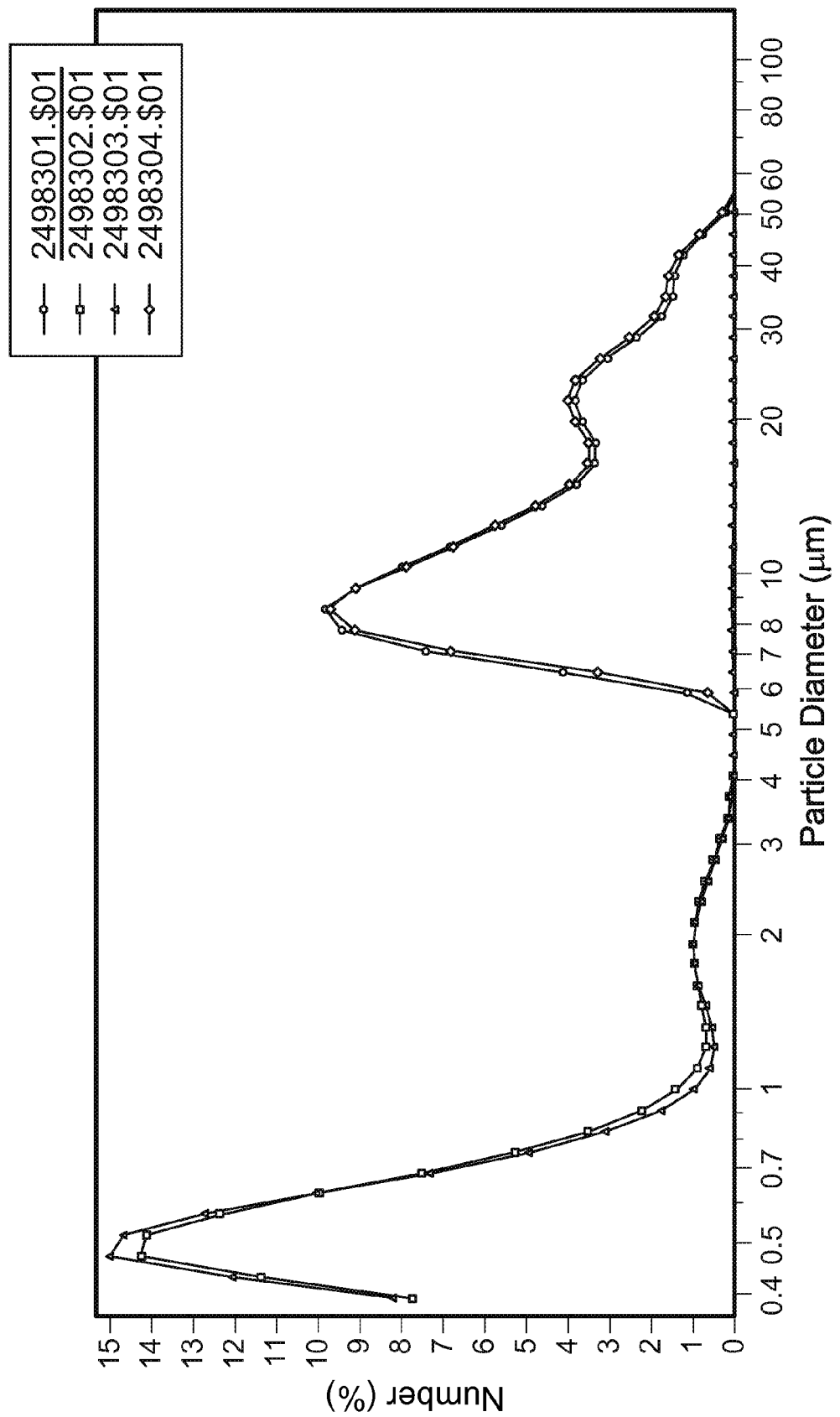
Figure 13A:
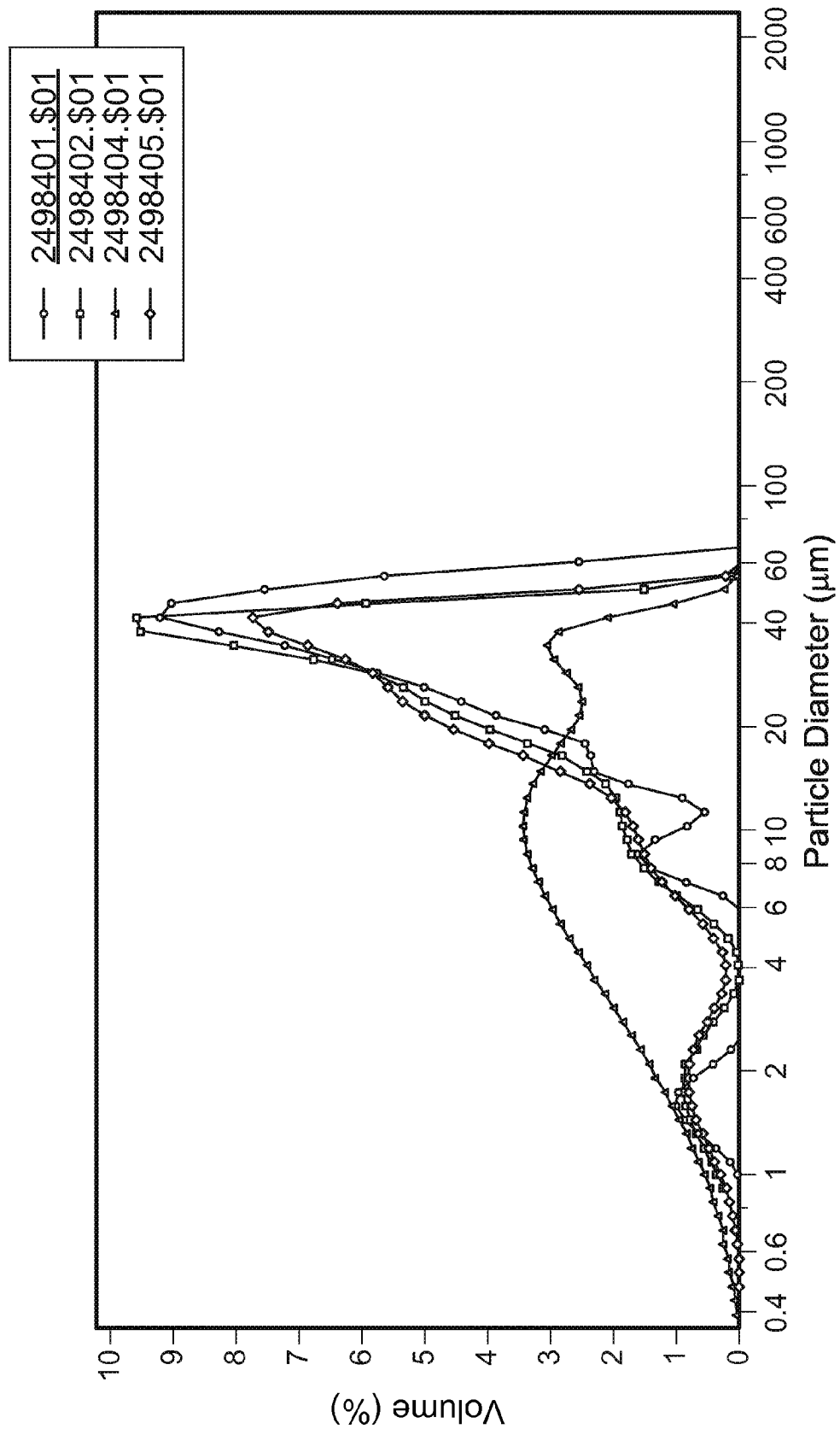
FIGS. 13A and B are graphs showing the overlay of volume—(A) and number—(B) based particle size distribution of BC-Lipase (80 μm) samples before injection, and after injections with BioJector 2000, through BD syringe with preattached 30 G×½" needle, and syringe with 25 G×⅝" needle.
Figure 13B:
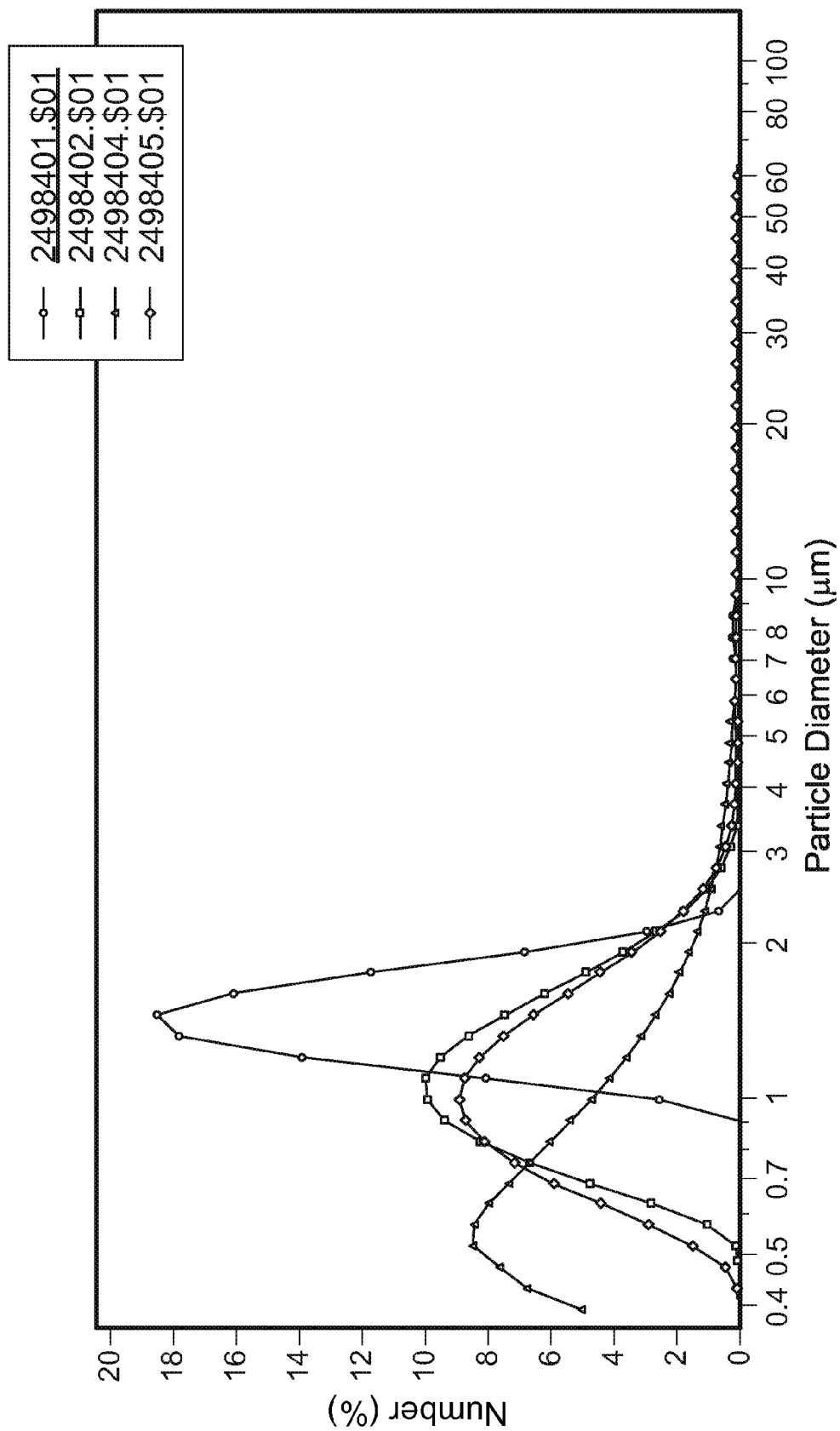

There was no significant change in particle size of sample after first and repeated injection with all of the injection systems used comparing to sample prior injection (Table 41). See also FIG. 10. These numbers are consistent with microscopic observations. Similar observations were made for ALTU-238 formulations.

No reduction in particle size or crystal morphology was observed when an HA-ALTU-238 sample was used for injections. After repeated injections, there was no further reduction in particle size as compared to the particle size observed in the sample originally free of crystalline aggregates. These data indicate feasibility of using needle-free injectors for administration of crystalline protein suspension formulations.

To study the influence of jet injectors on soluble hGH formulations, Nutropin AQ samples were used. No particulate formation was observed in the Nutropin AQ sample before injection or after injection through the 30 G×½ needle. However, after injection with the BioJector 2000 and VetJet injectors, formation of particulate matter in Nutropin AQ sample was observed. This particulate matter likely formed as a result of caused by the use of jet injectors. These data indicate that Nutropin AQ formulation may not be appropriate for needle-free injection systems and corroborate the notion that appropriate formulation development may be required for successful use of the needle free injectors for protein formulations.

ALTU-238 is a suspension of hGH crystals coated with poly-Arginine. The crystals have a needle shape of about 10 to 20 μm length and about 1-2 μm thickness. The suspension itself is stable. In previous studies, no significant sedimentation of crystals over at least a 6 month storage period was observed. However, there is an example of commercial insulin suspension formulations in which crystals tend to settle fast.

To extend the scope of the studies herein, the influence of jet injection systems on properties of other crystalline protein suspensions where crystals had different sizes and/or morphology and/or sedimentation properties was examined. A commercial insulin Humulin Ultra formulation was loaded into the BioJector syringe and injected after a hold period of three minutes in horizontal, vertical upright or upside down position. These hold samples were comparedto a sample that was injected almost immediately after loading the formulation into the jet injector's syringe. After injection, the amount of insulin in the injected part and the amount remaining inside the syringe were determined and expressed as a percentage, considering as 100% the material that was loaded into the syringe.

TABLE 42

Distribution of insulin in injected part and remaining in syringe after immediate injection and after 3 minute hold in different positions

| Sample | Injected, % | Remaining in syringe, % |
| --- | --- | --- |
| Injected immediately | 90 | 10 |
| Hold horizontal | 29 | 71 |
| Hold vertical upright | 61 | 39 |
| Hold vertical upside down | 90 | 10 |

In the sample that was injected immediately, 90% of the dose was delivered. When injection was delayed and the injector was held in the horizontal position, the dose delivered was as low as 29% of that loaded into syringe (Table 42). This could seriously endanger a patient. The use of jet injectors are not recommended for ad ministering this insulin formulation. The insulin suspension formulation is an example of crystalline protein formulations with high crystal sedimentation rate. Jet injectors may be inappropriate for use with crystalline protein suspensions with high sedimentation rates.

The same experiment was performed with an ALTU-238 formulation. The formulation was loaded into the BioJector's syringe and injected after a hold period of one hour in the horizontal, vertical upright or upside down position. These hold samples were compared to a sample that had been injected almost immediately after loading the formulation into the jet injector's syringe. After injection, the amount of hGH in the injected part and the amount remaining inside the syringe were determined and expressed as a percentage, considering as 100% the material that had been loaded into the syringe.

TABLE 43

| Distribution of hGH in injected and remaining in syringe part after immediate injection and after one hour hold in different positions | | |
|---|---|---|
| Sample | Injected, % | Remaining in syringe, % |
| Injected immediately | 95 | 5 |
| Hold horizontal | 95 | 5 |
| Hold vertical upright | 95 | 5 |
| Hold vertical upside down | 95 | 5 |

Unlike with the example testing insulin, there were no differences observed in dose distribution between the ALTU-238 sample that was immediately injected and the samples that were held before injection (Table 43). The hold time used for ALTU-238 was significantly longer.

No adverse influences of jet injection systems on aggregation and chemical purity of crystalline hGH in ALTU-238 formulations were observed. Moreover, particle size, morphology, particle surface charge and release properties did not change as result of using jet injection systems.

To extend the scope of the study, the influence of jet injection systems on the properties of other model crystalline protein suspensions, where crystals had different size, morphology, and sedimentation properties, were explored. In this experiment, the effects of jet injection systems on a suspension of small size hexagonal Burkholderia Cepacia ("BC") Lipase crystals were examined. No visual microscopic changes in crystal size or morphology in suspension were observed for the BC-Lipase crystals before and after injection.

TABLE 44

| Particle size distribution of BC-Lipase suspension | | | |
|---|---|---|---|
| Sample | Size μm % < 10 | Size μm % < 50 | Size μm % < 90 |
| 249-82-01 | 4.35 | 15.89 | 23.93 |
| 249-82-02 after BioJector 2000 injection | 4.05 | 14.62 | 21.44 |
| 249-82-03 after VetJet injection | 3.92 | 14.75 | 21.83 |
| 249-82-04 after BD syringe with 30G × ½" preattached needle | 4.06 | 15.14 | 23.00 |

There did not appear to be an effect on BC-Lipase particle size (Table 44, FIGS. 11A and B) or morphology as result of using any of the tested injection systems. Jet injection systems could be used for injection of crystalline protein suspension formulations when crystals are hexagonal with a median particle size of about 20 micrometers.

The effects of jet injection systems on the properties of other model crystalline protein suspensions, where crystals had a larger size and hexagonal morphology were next explored. In this experiment, the effects of jet injection systems on a suspension of hexagonal BC-Lipase crystals with a medium particle size of about 30 μm were examined. No changes in crystal morphology upon injection were detected, and no significant changes in volume based distribution were detected (Table 45).

TABLE 45

| Particle size distribution | | | |
|---|---|---|---|
| Sample | Size μm % < 10 | Size μm % < 50 | Size μm % < 90 |
| 249-83-01 | 15.32 | 31.38 | 45.27 |
| 249-83-02 after BioJector 2000 injection | 11.69 | 29.03 | 43.37 |
| 249-83-03 after VetJet injection | 13.06 | 30.14 | 44.20 |
| 249-83-04 after BD syringe with 30G × ½" preattached needle | 15.94 | 32.21 | 46.20 |

A significant decrease in number-based particle size distribution as a result of injection of BC-Lipase crystals through a BioJector 2000 or a VetJet needle-free (jet) injection systems was observed (FIGS. 12A and B). This is likely due to the generation of a great number of small particles with the use of jet systems but not with a 30 G needle. Although all samples were easily injected, it should be taken into account that the use of jet injection systems could change release profiles of formulations as a result of the increased amount of small size particles.

The effects of jet injection systems on the properties of other model crystalline protein suspensions, where crystals were even larger and had hexagonal morphology, were examined. In this experiment, the effects of jet injection systems on a suspension of rhomboidal three-dimensional BC-Lipase crystals with large crystals with a medium particle size of about 80 μm were examined.

TABLE 46

| Particle size distribution | | | |
|---|---|---|---|
| Sample | Size μm % < 10 | Size μm % < 50 | Size μm % < 90 |
| 249-84-01 | 9.29 | 32.72 | 51.49 |
| 249-84-02 after BioJector 2000 injection | 5.98 | 26.11 | 42.65 |
| 249-83-04 after BD syringe with 30G × ½" preattached needle | 2.08 | 9.23 | 32.33 |
| 249-83-05 after 25G × ⅝" needle | 5.25 | 24.48 | 43.24 |

Significant filtration was observed when trying to draw samples in injection module. Samples were loaded into the injection modules through the plunger side. It was not possible to load the samples into the VetJet system because of device design specifics.

When particle size is close to the size of the injection device orifice, crystalline samples either can not be loaded into the injection module or undergo destruction due to interaction with the injection device orifice. In the case of the 30 G needle, significant reduction in crystal size was observed because of the filtration effect. The smallest needle gauge the crystalline suspension was able to pass into and out of was a 25 gauge syringe. Even in this case, shear stress caused the formation of small crystalline debris (Table 46, FIGS. 13A and B). Hence, the largest dimension of the crystals in suspension should have at least about 3 times less size than the diameter of the orifice of jet injectors in order to be able used with jet injectors.

In other experiments, the feasibility of using jet injectors with a model suspension of crystalline Glutaryl Alcalase was explored. These elongated bipiramidal crystals have a largest dimension size of about 150 μm with a cross section size of about 30 μm.

TABLE 47

Particle size distribution

| Sample | Size μm % < 10 | Size μm % < 50 | Size μm % < 90 |
|---|---|---|---|
| 249-85-01 | 9.17 | 41.62 | 66.68 |
| 249-85-02 after BioJector 2000 injection | 2.27 | 29.25 | 58.11 |
| 249-85-04 after BD syringe with 30G × ½" preattached needle | 4.97 | 36.98 | 59.21 |
| 249-85-05 after 25G × ⅝" needle | 8.39 | 39.53 | 61.38 |
| 249-85-05 after 18G × 1" needle | 8.72 | 39.00 | 60.71 |

Significant filtration was observed when trying to draw the samples into the injection modules. Sample was drawn freely into the syringe only when an 18 G needle was used. Samples were loaded into the injection module through the plunger side (not including the 18 G needle example). It was not possible to load the sample into the VetJet system because of specifics of the device design. An increase in injection time was observed for the crystalline Glutaryl Alcalase suspension when the BioJector 2000 was used. Accumulation of crystalline debris in samples was observed after using the jet injector and fine gauge needles.

Figure 14A:
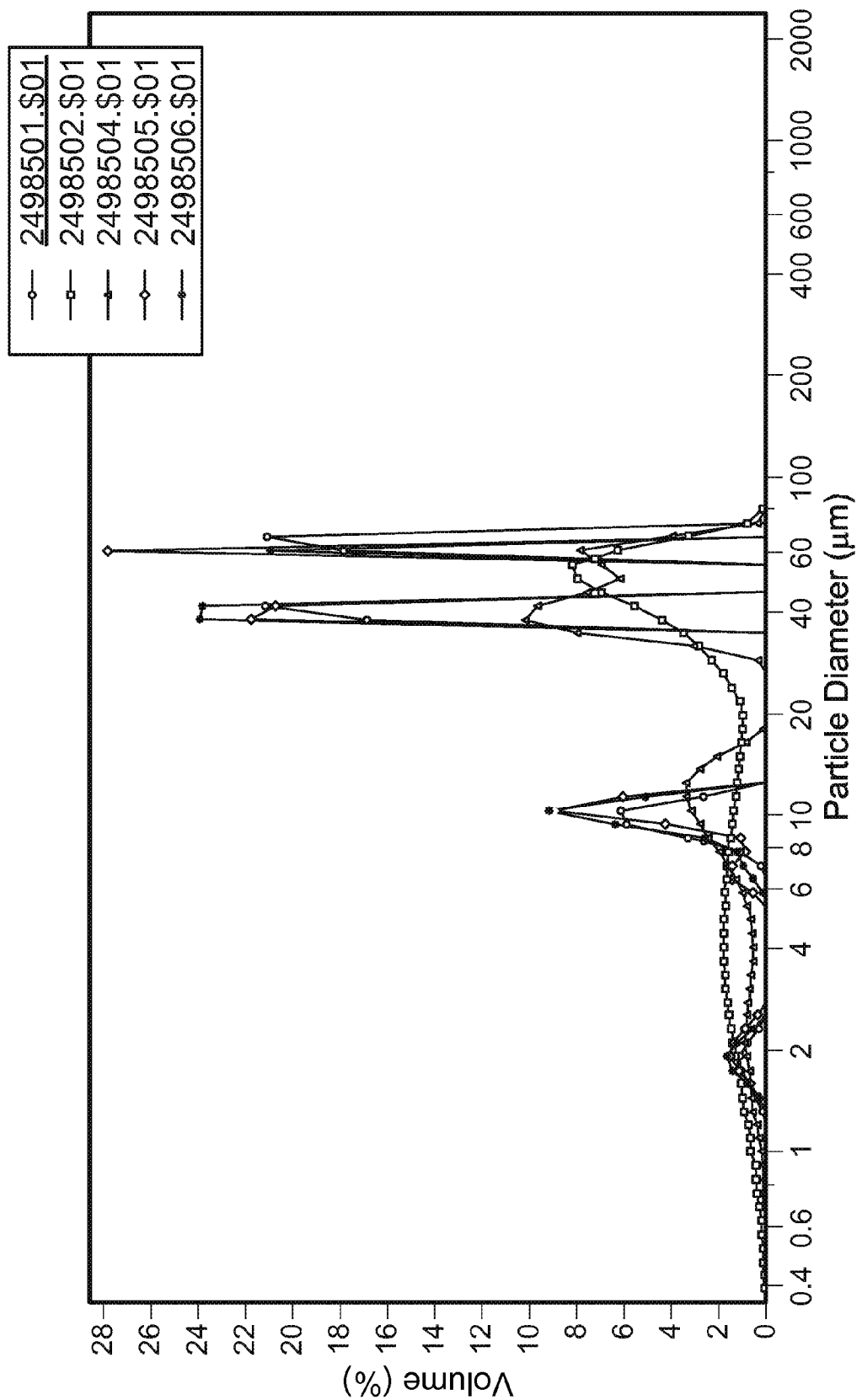
FIGS. 14A and B are graphs showing the overlay of volume—(A) and number—(B) based particle size distribution of Glutaryl Alcalase samples before injection, and after injections with the use of BioJector 2000, through BD syringe with preattached 30 G×½" needle, and 25 G×⅝" and 18 G×1" needles.
Figure 14B:
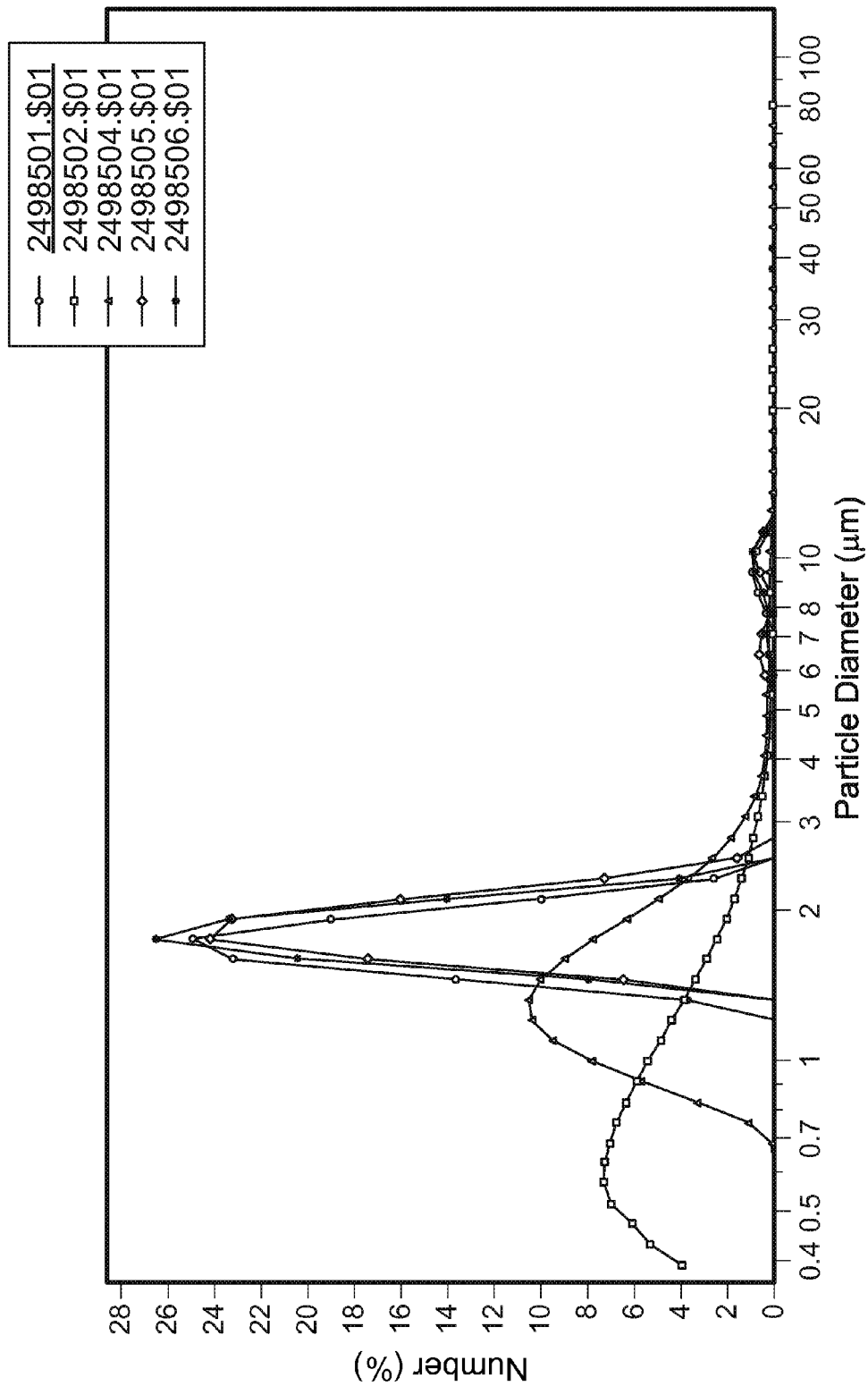

Despite no measured significant changes in particle size, as measured by a Coulter LS230 (Table 47), significant decreases in the number-based particle size distribution (FIGS. 14A and B) were observed as result of injecting Glutaryl Alcalase crystals through the BioJector 2000 needle-free injection system and the 30 G needle. This can be explained by the destruction of crystals when using the jet system or 30 G needle for injection. When particle size is close to the size of the injection device orifice, crystalline samples either can not be loaded into injection module or undergo destruction because of interactions with the injection device wall. As the diameter of needles was increased, less destruction of crystals was observed.

Method Protocols

Injection: crystalline formulations are injected using the BioJector 2000 system with 1S021 syringe and VetJet system with 0.0062" nozzle syringe Ref # K7000, BD 0.5 cc syringe with preattached 30 G×½" needle (BD Part # 328466), through 30 G×½" (BD Part #305106), 25 G×⅝" (BD Part #305122), 18 G×1½" (BD Part #305196) attached with luer-lock to 1 mL syringe (BD Part #309628). 0.25 mL Samples are tested in duplicate. BioJector 2000 and VetJet systems are used according to BioJector's recommendations.

SE-HPLC: To determine purity using the SE-HPLC method, a Phenomenex BioSep SEC-S-2000 column is used. Ten microliters of 2 mg/mL concentration sample is injected into the column. The running buffer is composed of 3% IPA and 60 mM sodium phosphate, pH 7.0. The flow rate is set to 0.6 mL/min and the run time is 30 minutes. Detection is performed at 214 nm. The resulting chromatogram is manually integrated. Percent purity (monomer) is calculated based on peak area.

RP-HPLC: RP-HPLC is used for purity testing. To determine the purity of hGH using the RP-HPLC method, a C5 Supelco Discovery Bio Wide Pore Column, 5 cm×4.6 mm, 3 μm particle size, 30 nm Pore size is used. The column thermostat temperature was set to 37° C. Ten microliters of sample at 2 mg/mL concentration is injected. The elution is carried out at a flow rate of 1.0 mL/min with a gradient system present by mobile phase A (0.1% TFA in water) and mobile phase B (0.8% TFA in MeCN). Gradient system changed from 5% B to 50% B from 0-2.5 min., then 50% to 70% B in 2.5-15.5 min. then, 70% to 90% in 15.5 to 17 min., immediately following this 5% B is re-established. A 3 min post-time is held before the start of the next run. Detection is performed at 214 nm. The resulting chromatogram is manually integrated. Percent purity is calculated based on peak area.

IEX-HPLC (Strong Cation Exchange) Chromatography: SCX-hGH is used as deamidation specific in stability testing. To determine the purity of hGH using the IEX-HPLC method, a PolyLC (NEST Group cat #P054SE0503) column is used. The column thermostat temperature is set to 30° C. Twenty microliters of sample at 2 mg/mL concentration is injected. The elution is carried out at a flow rate of 1 mL/min with a gradient system present by mobile phase A (50 mM Na Acetate, pH 4.6) and mobile phase B (50 mM Na Acetate, pH 4.6 250 mM NaCl). The gradient system is changed from 0% B to 20% B from 0 to 5 min., then 20% to 70% B in 5 to 25 min. then, 70% to 100% in 25 to 25.1 min. 100% B is kept until 27 min. following 27.1 min, 0% B is re-established for a 5 min. post-time. Detection is performed at 214 nm and 280 nm. The resulting chromatogram is manually integrated. Percent purity is calculated based on peak area.

ParticleSize Distribution (PSD): Particle size distribution is determined by laser diffraction using a Coulter LS 230 Particle Size Analyzer (Coulter Corp., Miami, Fla.) with micro volume module. The sample is diluted in Sample buffer (Formulation Vehicle for Crystalline Protein 3) to achieve an operation range of 8% to 12% obscuration. Data analysis is performed using the Fraunhofer optical model. Size in μm of particle fraction representing cumulative volume distribution limits of 10% (dl10), 50% (median) and 90% (dl90) is reported.

3-pH Dissolution Test: A 3-pH dissolution test is used to assess changes in dissolution profiles in ALTU-238 samples.

Particle Surface Charge: Particle surface charge is determined using Zetasizer Nano-Z (Malvern Instruments Ltd. UK). The running buffer is 20 mM Tris, pH 7.5. Zeta Potential Transfer Standard is used to calibrate the instrument (Malvern catalog #DTS1050). For each sample, a 12 μl crystalline aliquot (concentration between 10 to 30 mg/ml) is added to 588 μl running buffer, and three measurements are taken at room temperature.

Microscopic Appearance: The appearance of the crystalline test article is assessed by microscopy to detect any relevant changes in the test article due to injections.

Example 5

ALTU-238 is a long-acting poly-arginine (poly-Arg) coated crystalline human growth hormone (somatropin). As a further development, lyophilized forms and reconstituted lyophilized formulations were developed. The reconstituted lyophilized formulations are predicted to achieve 24 months or longer chemical stability at 2-8° C. after being resuspended.

An exemplary lyophilized formulation of hGH or an hGH derivative contains:

1. About 20 to about 50 mg/mL hGH crystal suspension
2. Tris or a combination buffer of phosphate with either Tris or histidine as the buffer,
3. pH range from 7 to 9
4. Salt: sodium chloride or sodium acetate ranging from 50 mM to 100 mM
5. Polyethylene glycol 6000 or 8000 as the suspending and caking agents, ranging from 2.5% to 10%
6. Siliconized vials or coated vials such as Schott type I plus glass vials, or coated surface container closure 7. Freezing shelf temperature of −50° C. to −60° C., the primary drying shelf temperature of −30° C. to 10° C. and the 2nd drying of 20° C. to 40° C. for the lyo cycle parameter.

These components and amounts are suitable for the formulations prior to lyophiliation and also for the formulations after the lyophilized hGH is reconstituted.

One or more of the test methods listed in Table 48 are used to evaluate the stability of the reconstituted formulations made from the lyophilized forms. Details for carrying out the test methods are known in the art and described herein.

TABLE 48

Test Methods

| TEST METHODS | APPLICATION |
| --- | --- |
| pH | pH maintenance |
| Cake and reconstitution appearance | Suspension description |
| Particle Size Distribution | Physical stability |
| Reconstitution time | Physical stability |
| Crystal Morphology | Physical stability |
| Purity by Reverse Phase Chromatography (RP-HPLC) | Chemical degradation (oxidation) |
| Purity by Size Exclusion Chromatography (SEC) | Soluble aggregates |
| Poly(L-arginine) Total Content by Reverse Phase Chromatography | Facilitate controlled release |
| Free Poly(L-arginine) and hGH Content in Supernatant by Reverse Phase Chromatography | Physical stability |
| Absorbance at 280 nm | Protein Concentration |
| Undissolved crystals/aggregates by Absorbance at 320 nm | Insoluble aggregates |
| Cation Exchange HPLC (CEX) | Chemical degradation (deamidation) |
| Crystal Dissolution | hGH product release profile |

Figure 15:
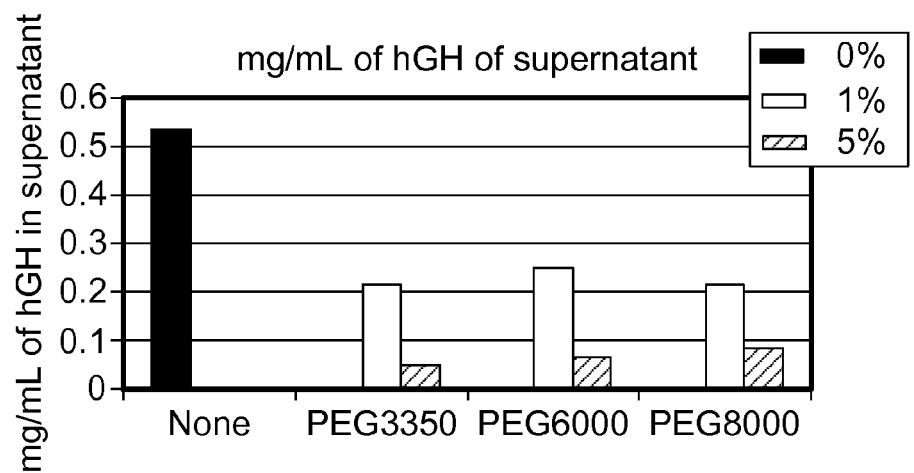
FIG. 15 is a graph showing the effect of PEG concentrations on the amount of dissolved hGH in the supernatant. The base formulation was Tris buffer at pH 7.5

The first lyophilization study evaluated the dissolved hGH in the supernatant and the effect of excipients on the stability upon lyophilization. The base formulation was Tris buffer at pH 7.5. Various concentrations of PEG; carbohydrates (sucrose, mannitol, sorbitol and lactose); and formulations with and without salt were tested. The free hGH in the supernatant is an indication of the crystal integrity. Thus, the amount of dissolved hGH in the supernatant was monitored to assure that the controlled release profiles were unchanged post lyophilization. The result of dissolved hGH concentrations in the supernatant of the pre lyophilization (prelyo) sample as shown in FIG. 15 indicates that the PEG concentration does have an impact on the solubility of the crystal, and the lower the percentage of PEG, the more crystals are dissolved in the supernatant. For the experiments shown in the figure, the base formulation was Tris buffer at pH 7.5. In addition, sample with no PEG have the highest amount of dissolved hGH in the supernatant.

ALTU-238 in water had the appearance of a loose powder, without a cake appearance after lyophilization. Otherwise, all samples exhibited reasonable cake formation with slight shrinkage from the edge of the vial. Upon reconstitution, the poly-Arg complexed crystals without any excipient settled to the bottom of the vials due to lack of suspending agents. The formulation containing a carbohydrate such as mannitol, sucrose, sorbitol or lactose suspended immediately upon reconstitution but settled down within 15 minutes, indicating a difference in sedimentation rate after lyophilization. The starting material or prelyo suspension was mostly small 2 to 20 μm clusters of tiny rod shape crystals. However, the crystal sizes appear to be significantly larger for some formulations post lyophilization. The formulations examined pre and post lyophilization contained 25 mg/mL Altu-238 in Tris, pH 7.5; mg/mL complexed crystals in Tris, 5% lactose, pH 7.5; or 25 mg/mL complexed crystals in Tris, sodium acetate and 5% PEG6000, pH 7.5. The results indicate that the formulation containing 5% PEG maintained the crystal morphology post lyophilization.

The target hGH/pR ratio was 5 to 7.5 for the prelyo suspension. However, the hGH/poly-Arg ratios of the prelyo suspension were much higher (~20) for the formulation containing 1% PEG or carbohydrate, which suggests a loss of poly-Arg coating in these formulations, likely resulting from crystal dissolving. This was confirmed by the fact that the hGH concentrations in the supernatant were also higher for the prelyo suspensions. In addition, the postlyo crystals are clumps for samples containing 1% PEG or carbohydrate more so than those of 5% PEG, which again suggests loss of poly-Arg, resulting in crystals sticking together and thus changing the morphology. Therefore, the concentration of PEG is critical in stabilizing ALTU-238 during the lyo process.

Also, the pH of the reconstituted lyo samples shifts higher after the lyo process, from pH 7.5 to 8.2 for formulations containing Tris. To identify the cause, a freeze/thaw study of these tested formulations was performed in the FTS lyophilizer using the same freezing rate, 1° C./min, as the lyo cycle. Then all samples were thawed at room temperature. The results indicated that the pH shift was only about 0.05 to 0.09 per pH unit. Therefore, it was the drying process that induced the pH changes.

To improve the formulation, the following studies were focused on the selection of buffer species and buffer concentrations. The pH was raised to ~8 for the Tris containing prelyo suspension because Tris has the maximum buffer capacity at this pH; and/or adding phosphate as one of the buffer components because phosphate can buffer at pH 7.5 upon reconstitution. The idea of selecting histidine as the second buffer was to prevent pH shifting too low due to the presence of phosphate during the lyophilization process, resulting in crystal dissolution. Two fill volumes: 0.5 mL and 1.2 mL, to deliver 0.2 mL and 1.0 mL of drug product, were evaluated. The three buffer systems that could achieve our target were formulated in Tris, pH 8.0; histidine with phosphate at pH 7.5. One interesting observation was that the pH dropped to 8.0 for the sample that was formulated in Tris, pH 8.6, which confirmed the theory that optima buffer range for complexed hGH crystals should be around 8. Based on all of these results, the buffer using Tris at pH 8; and combinations of two buffers which contain histidine and phosphate or Tris/phosphate are selected for poly-Arg complexed hGH crystals.

Selected formulations were tested for stability, and pH measurements were obtained after various storage periods. Other than the initial pH shifts, there were no changes of pH during the storage period.

The in-vitro dispersed dissolution rate was tested, and no significant changes are observed upon storage; the dissolution rates were comparable to the clinical trial lots.

The polyethylene glycol concentrations of 2.5%, 5%, and 10% and the range of 2.5% to 10% were also established. All samples could be resuspended within one minute. No differences were observed in oxidation, deamidation, aggregation, or dissolved hGH in these formulations after 3 months at 2-8° C. or 40° C.

In addition, no differences in stability were observed for hGH concentrations ranging from 20 to 50 mg/mL of poly-Arg complexed hGH crystals upon reconstitution. Based on the results, the free hGH in the supernatant and dispersed dissolution profile are comparable for all tested concentrations. In addition, there are no differences in chemical stability profiles.

The lyo cycle was optimized using the formulation containing Tris, sodium acetate, and PEG6000 at pH 7.5. Various lyo parameters were tested. The freezing DSC thermograms of a PEG containing sample indicate a thermo event occurred around −20° C. which is contributed to by PEG. To avoid the complication by PEG, <−20° C. to product temperatures were targeted for the selection of the primary drying temperature for the lyo cycle development. As shown in Table 49, at freezing temperature of −60° C. or −50° C. and the primary drying shelf temperature range from −30° to 10° C., all finished lyo products exhibited reasonable cake formation with a smooth surface, slight shrinkage from the edge of the vial. No differences are observed in the cake appearance of lyo cakes from various lyo cycles. In addition, the measured product temperatures were all less than −20° C., as desired.

TABLE 49

Summary of lyophilization cycle parameters. The vacuum was set at 100 mTorr

| | SET SHELF TEMP (° C.) | FREEZING SHELF TEMP (° C.) | PRIMARY DRYING SHELF TEMP (° C.) | SECONDARY DRYING SHELF TEMP (° C.) | FINAL DEW (° C.) | PRODUCT TEMP. (° C.) |
|---|---|---|---|---|---|---|
| Lyo#6 | −30 | −60 | −30 | 20 | −42.1 | −34 |
| Lyo#8 | −30 | −60 | −30 | 40 | −42.1 | −34 |
| Lyo#9 | −10 | −60 | −10 | 40 | −40.1 | N/A |
| Lyo#11 | 0 | −50 | 0 | 30 | −43.1 | −22 |
| Lyo#10 | 10 | −60 | 10 | 40 | −42.0 | −25 |

Figure 16:
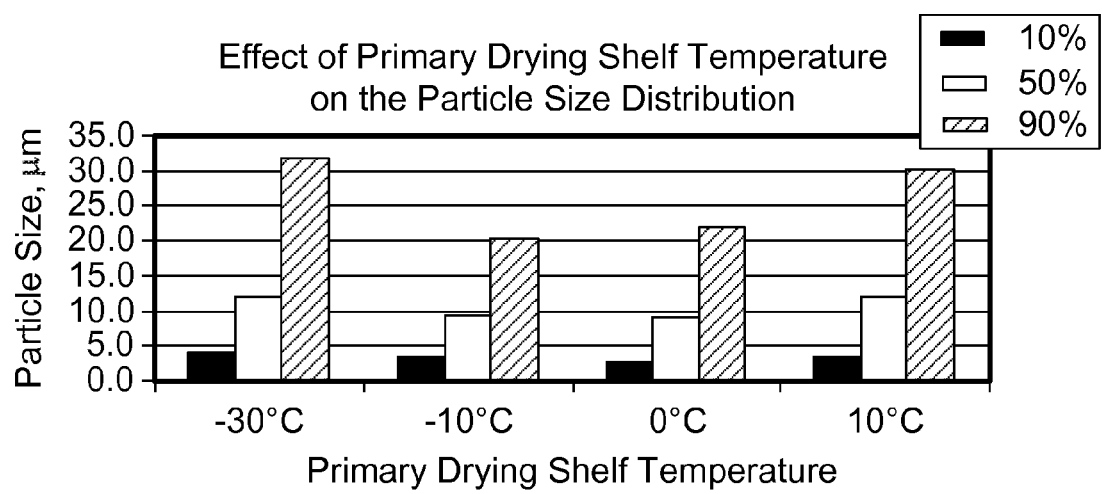
FIG. 16 is a graph showing particle size distributions for samples generated by different lyo cycles.

The particle size distribution was analyzed and the particle size distributions are listed in FIG. 16. There was no difference in particle size distribution for all tested cycles.

In conclusion, the lyo cycles defined for the embodiments herein are:
a. Freezing rate of 1° C./min
b. Frozen at −50° C. to −60° C.
c. Primary drying shelf temperature range from −30° C. to 10° C.
d. Secondary Drying shelf temperature from 20° C. to 40° C.

The stability results of one of the lead formulations were summarized in the table below. All data are comparable when compare the samples that generated with these two cycles.

Various container closures for the lyo products were also compared. The poly-Arg coated crystals quickly and easily stick to glass vials without silicon oil and coated surface. The crystals stick to the non-siliconized vial easily, and this stickiness will be worse for a multi-dose product. Therefore, the container closure for poly-Arg complexed hGH crystals need to be siliconized or vials with coated surface such as type I plus coated vials.

When reconstituted with a diluent containing a preservative, the reconstituted formulation may be used as a multi-dose formulation. The advantage of a multi-dose formulation is that it facilitates ease of use for the patient, reduces waste by allowing full use of the vial contents, thereby resulting significant savings.

Four commonly used preservatives were tested for suitability with complexed hGH crystals: phenol, m-cresol, chlorobutanol, and benzyl alcohol. The lyo formulations containing Tris, sodium acetate, and PEG were reconstituted with water containing one of these preservatives and the stability of the reconstituted samples was analyzed. All vials could be reconstituted/resuspended within 10 seconds and no changes of crystal morphology were seen, except for the sample containing benzyl alcohol which had more clumps.

The stability of these reconstituted suspensions containing preservatives was analyzed. The results indicate that all reconstitution suspensions are stable at 2-8° C. for at least one month. Therefore, m-cresol, phenol or Chlorobutanol can be used as a preservative with the lyo formulations.

A number of embodiments of the invention have been described. Nevertheless, it will be understood that various modifications may be made without departing from the spirit and scope of the invention. Accordingly, other embodiments are within the scope of the following claims.

What is claimed is:

1. An hGH pharmaceutical formulation comprising polyelectrolyte complexed crystallized recombinant hGH;
a biologically compatible buffer in the pH range of 5.4 to 7.0, selected from the group consisting of triethanolamine, imidazole, glycine, histidine, citrate, acetate, phosphate and tris, or a combination thereof, and
one or more additional components selected from the group consisting of a sodium salt having a sodium ion concentration in the range of 60-200 mM, a suspending agent, a chemical stabilizer, a surfactant, and a preservative, wherein the biologically compatible buffer and the one or more additional components are selected from the group consisting of:
10 mM Na Phosphate, 25 mM Tris, 100 mM NaAc, 5% PEG 6000, pH 6.5;
10 mM Na Phosphate, 0.25% Phenol, 150 mM NaCl, 5% PEG 6000, pH 6.0;
10 mM Na Citrate, 0,2% Tween 20, 0.25% Phenol, 150 mM NaCl, pH 6.0;
30 mM Triethanolamine, 100 mM Na Acetate, 5% PEG6000, pH 6.8;
25 mM Triethanolamine, 10 mM Methionine, 100 mM NaCl, 2% PEG3350, pH 6.8;
25 mM imidazole, 100 mM Na Acetate, 5% PEG6000, pH 6.5;
2 mM Na citrate, 8 mM Na phosphate, 120 mM NaCl, 0.3% Phenol, pH 6.0;
10 mM Na Phosphate, 100 mM Glycine, 0.3% phenol, pH 6.0;
10 mM Na Phosphate, 100 mM NaCl, 0.3% phenol, pH 6.0;
10 mM Na Phosphate, 100 mM Na acetate, 5% PEG 6000, pH 6.0;
10 mM Na Phosphate, 100 mM NaCl, 5% PEG 6000, pH 6.0;
10 mM Na Phosphate, 100 mM NaCl, 5% PEG 6000, pH 6.5;

2 mM Na citrate, 8 mM Na phosphate, 120 mM NaCl, 0.3% Phenol pH 5.4;

10 mM Na phosphate, 100 mM NaCl, 10% w/v PEG3350 pH 6.0;

10 mM Na citrate, 80 mM Na Glycine, 10% w/v PEG6000 pH 5.4; and 10 mM Na acetate, 120 mM NaCl, 10% w/v PEG6000 pH 5.6.

2. The hGH pharmaceutical formulation of claim 1, further comprising a preservative.

3. The hGH pharmaceutical formulation of claim 2, wherein the preservative is phenol, m-cresol, chlorobutanol, or benzyl alcohol.

4. The hGH pharmaceutical formulation of claim 1, further comprising hyaluronic acid.

5. The hGH pharmaceutical formulation of claim 1, further comprising an anti-microbial agent.

6. The hGH pharmaceutical formulation of claim 1, further comprising a chemical stabilizer.

* * * * *